（12） United States Patent
Lin et al.

US008080246B2

(10) Patent No.: US 8,080,246 B2
(45) Date of Patent: *Dec. 20, 2011

(54) COLONY STIMULATING FACTOR 1 RECEPTOR (CSF1R) EXTRACELLULAR DOMAIN FUSION MOLECULES

(75) Inventors: Haishan Lin, Moraga, CA (US); Li Long, Lafayette, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/626,598

(22) Filed: Nov. 25, 2009

(65) Prior Publication Data

US 2010/0136007 A1 Jun. 3, 2010

Related U.S. Application Data

(60) Provisional application No. 61/118,423, filed on Nov. 26, 2008, provisional application No. 61/118,425, filed on Nov. 26, 2008.

(51) Int. Cl.
*A61K 38/00* (2006.01)
*C07H 21/02* (2006.01)
(52) U.S. Cl. .................. 424/134.1; 536/23.1; 514/16.6; 514/17.9
(58) Field of Classification Search .................. None
See application file for complete search history.

(56) References Cited

U.S. PATENT DOCUMENTS

| 5,866,114 | A | 2/1999 | Pandit et al. |
|---|---|---|---|
| 6,184,354 | B1 | 2/2001 | Koths et al. |
| 7,108,852 | B2 | 9/2006 | Devalaraja et al. |
| 7,247,618 | B2 | 7/2007 | Rajavashisth |
| 7,455,836 | B2 | 11/2008 | Hamilton et al. |
| 2002/0119494 | A1 | 8/2002 | Jung et al. |
| 2006/0286102 | A1 | 12/2006 | Jin et al. |
| 2007/0148172 | A1 | 6/2007 | Lawson et al. |
| 2007/0166788 | A1 | 7/2007 | Jin et al. |
| 2010/0136006 | A1 | 6/2010 | Lin et al. |

FOREIGN PATENT DOCUMENTS

| CA | 2388298 A1 | 5/2001 |
|---|---|---|
| EP | 2241333 A1 | 10/2010 |
| WO | WO 89/03687 A1 | 5/1989 |
| WO | WO 99/29345 A1 | 6/1999 |
| WO | WO 01/34177 A2 | 5/2001 |
| WO | WO 2004/045532 A2 | 6/2004 |
| WO | WO 2005/070447 A2 | 8/2005 |
| WO | WO 2006/012451 A2 | 2/2006 |
| WO | WO 2007/075933 A2 | 7/2007 |
| WO | WO 2007/081879 * | 7/2007 |
| WO | WO 2007/081879 A2 | 7/2007 |
| WO | WO 2007/120252 A2 | 10/2007 |
| WO | WO 2008/060610 A2 | 5/2008 |
| WO | WO 2008/124858 A2 | 10/2008 |
| WO | WO 2008/150383 A2 | 12/2008 |
| WO | WO 2009/026303 A1 | 2/2009 |
| WO | WO 2009/112245 A1 | 9/2009 |

OTHER PUBLICATIONS

International Search Report and Written Opinion mailed Jun. 9, 2010, for Application No. PCT/US 09/06299, filed Nov. 25, 2009 (17 pages).
International Search Report and Written Opinion mailed May 24, 2010, for Application No. PCT/US 09/06301, filed Nov. 25, 2009 (13 pages).
Aharinejad et al., Colony-stimulating Factor-1 Blockade by Antisense Oligonucleotides and Small Interfering RNAs Suppresses Growth of Human Mammary Tumor Xenografts in Mice, Cancer Research, vol. 64, Aug. 2004, pp. 5378-5384.
Aharinejad et al., Colony-stimulating Factor-1 Antisense Treatment Suppresses Growth of Human Tumor Xenografts in Mice, Cancer Research, vol. 62, Sep. 2002, pp. 5317-5324.
Ando et al., Imatinib Mesylate Inhibits Osteoclastogenesis and Joint Destruction in Rats with Collagen-induced Arthritis, J. Bone Miner. Metab., vol. 24, Jan. 2006, pp. 274-282.
Apollo Cytokine Research, Human hcx-™ M-CSF R, Fc Chimera, Product Information Sheet from http://www.biocompare.com/itemdetails.asp?itemid=837066, printed Feb. 4, 2008 (2 pages).
Birchenall-Roberts, Inhibition of Murine Monocyte Proliferation by a Colony-stimulating Factor-1 Antisense Oligodeoxynucleotide, J. Immunol., vol. 145, Nov. 1990, pp. 3290-3296.
Bischof et al., Exacerbation of Acute Inflammatory Arthritis by the Colony-stimulating Factors CSF-1 and Granulocyte Macrophage (GM)-CSF: Evidence of Macrophage Infiltration and Local Proliferation, Clin. Exp. Immunol., vol. 119, 2000, pp. 361-367.
Campbell et al., The Colony-stimulating Factors and Collagen-induced Arthritis: Exacerbation of Disease by M-CSF and G-CSF and Requirement for Endogenous M-CSF, J. Leukoc. Biol., vol. 68, Jul. 2000, pp. 144-150.
Chaika et al., CSF-1 Receptor/Insulin Receptor Chimera Permits CSF-1-dependent Differentiation of 3T3-L1 Preadipocytes, J. Biol. Chem., vol. 272, No. 18, May 1997, pp. 11968-11974.
Chitu et al, Colony-stimulating Factor-1 in Immunity and Inflammation, Curr. Opin. Immunol., vol. 18, No. 1, Feb. 2006, pp. 39-48.
Conway et al., Inhibition of Colony-stimulating-factor-1 Signaling in vivo with the Orally Bioavailable cFMS Kinase Inhibitor GW2580, PNAS, vol. 102, No. 44, Nov. 2005, pp. 16078-16083.
Conway et al., Effects of the cFMS Kinase Inhibitor 5-(3-Methoxy-4-((4-methoxybenzyl)oxy)benzyl)pyrimidine-2,4-diamine (GW2580) in Normal and Arthritic Rats, J. Pharmacol. Exp. Therapeutics, vol. 326, No. 1, Apr. 2008, pp. 41-50.

(Continued)

*Primary Examiner* — Robert Landsman
*Assistant Examiner* — Ian Dang
(74) *Attorney, Agent, or Firm* — Finnegan, Henderson, Farabow, Garrett & Dunner, LLP

(57) ABSTRACT

The present invention relates to specific CSF1R ECD fusion molecules that exhibit improved therapeutic properties. The invention also relates to polypeptide and polynucleotide sequences, vectors, host cells, and compositions comprising or encoding such molecules. The invention also relates to methods of making and using the CSF1R ECD fusion molecules. The invention further relates to methods of treatment using the CSF1R ECD fusion molecules. For example, certain CSF1R ECDs of the invention may be used to treat rheumatoid arthritis (RA) or multiple sclerosis (MS).

24 Claims, 14 Drawing Sheets

OTHER PUBLICATIONS

Dandekar et al., Comparison of the Signaling Abilities of the Cytoplasmic Domains of the Insulin Receptor and the Insulin Receptor-related Receptor in 3T3-L1 Adipocytes, Endocrinology, vol. 139, No. 8, 1998, pp. 3578-3584.

Dewar et al., Imatinib as a Potential Antiresorptive Therapy for Bone Disease, Blood, vol. 107, No. 11, Jun. 2006, pp. 4334-4337.

Goswami et al., Macrophages Promote the Invasion of Breast Carcinoma Cells via a Colony-stimulating Factor-1/Epidermal Growth Factor Paracrine Loop, Cancer Res., vol. 65, No. 12, Jun. 2005, pp. 5278-5283.

Hamilton, CSF-1 Signal Transduction, J. Leukoc. Biol., vol. 62, Aug. 1997, pp. 145-155.

Hamilton, Colony-stimulating Factors in Inflammation and Autoimmunity, Nature Reviews, vol. 8, Jul. 2008, pp. 533-544.

Hegen et al., Utility of Animal Models for Identification of Potential Therapeutics for Rheumatoid Arthritis, Ann. Rheum. Dis., vol. 67, published online Nov. 2007, pp. 1505-1515.

Ide et al., Expression of Colony-stimulating Factor 1 Receptor During Prostate Development and Prostate Cancer Progression, PNAS, vol. 99, No. 22, Oct. 2002, pp. 14404-14409.

Ide et al., Serum Level of Macrophage Colony-stimulating Factor is Increased in Prostate Cancer Patients with Bone Metastasis, Human Cell, vol. 21, No. 1, Feb. 2008, pp. 1-6.

Irvine et al., A CSF-1 Receptor Kinase Inhibitor Targets Effector Functions and Inhibits Pro-inflammatory Cytokine Production from Murine Macrophage Populations, FASEB, vol. 20, Sep. 2006, pp. E1315-E1326.

Kingsley et al., Molecular Biology of Bone Metastasis, Mol. Cancer Ther., vol. 6, No. 10, Oct. 2007, pp. 2609-2617.

Kitaura et al., M-CSF Mediates TNF-induced Inflammatory Osteolysis, J. Clin. Invest., vol. 115, No. 12, Dec. 2005, pp. 3418-3427.

Kluger et al., Macrophage Colony-stimulating Factor-1 Receptor Expression is Associated with Poor Outcome in Breast Cancer by Large Cohort Tissue Microarray Analysis, Clinical Cancer Res, vol. 10, Jan. 2004, pp. 173-177.

Kubota et al., M-CSF Inhibition Selectively Targets Pathological Angiogenesis and Lymphangiogenesis, J. Exp. Med., vol. 206, No. 5, Apr. 2009, pp. 1089-1102.

Kutza et al., Macrophage Colony-stimulating Factor Antagonists Inhibit Replication of HIV-1 in Human Macrophages, J. Immunol., 2000, vol. 164, pp. 4955-4960.

Lee et al., Functional Dissection of Structural Domains in the Receptor for Colony-stimulating Factor-1, J. Biol. Chem., vol. 267, No. 23, Aug. 1992, pp. 16472-16483.

Li et al., Conditional Deletion of the Colony Stimulating Factor-1 Receptor (c-fms Proto-Oncogene) in Mice, Genesis, vol. 44, May 2006, pp. 328-335.

Li et al., Role of Dimerization and Modification of the CSF-1 Receptor in its Activation and Internalization During the CSF-1 Response, The EMBO Journal, vol. 10, No. 2, 1991, pp. 277-288.

Lin et al., Colony-stimulating Factor 1 Promotes Progression of Mammary Tumors to Malignancy, J. Exp. Med., vol. 193, No. 6, Mar. 2001, pp. 727-739.

Lin et al., The Macrophage Growth Factor CSF-1 in Mammary Gland Development and Tumor Progression, J. Mammary Gland Biology Neoplasia, vol. 7, Apr. 2002, pp. 147-162.

Lin et al., Discovery of a Cytokine and its Receptor by Functional Screening of the Extracellular Proteome, Science, vol. 320, May 2008, pp. 807-811.

Lin et al., Regulation of Myeloid Growth and Differentiation by a Novel Cytokine, Interleukin-34 (IL-34), via the CSF-1 Receptor, poster presented at Cytokines in Health & Disease, Fifteenth Annual Conference of the International Cytokine Society (San Francisco, CA, Oct. 26-30, 2007, 1 page.

Lipton, Future Treatment of Bone Metastases, Clin Cancer Res, vol. 12, 20 Suppl., Oct. 2006, pp. 6305s-6308s.

Lopez-Diego et al., Novel Therapeutic Strategies for Multiple Sclerosis—A Multifaceted Adversary, Nature Reviews Drug Discovery, vol. 7, Nov. 2008, pp. 909-925.

MacDonald et al., An Antibody Against the Colony-stimulating Factor 1 Receptor Depletes the Resident Subset of Monocytes and Tissue- and Tumor-associated Macrophages But Does Not Inhibit Inflammation, Blood, vol. 116, Aug. 2010, pp. 3955-3963.

Mancino et al., Breast Cancer Increases Osteoclastogenesis by Secreting M-CSF and Upregulating RANKL in Stromal Cells, J. Surgical Research, vol. 100, Jul. 2001, pp. 18-24.

Montell, Metastasis Movies, Macrophages, Molecules and More, EMBO Reports, vol. 4, No. 5, Apr. 2003, pp. 458-462.

Mroczko et al., Serum Macrophage-colony Stimulating Factor Levels in Colorectal Cancer Patients Correlate with Lymph Node Metastasis and Poor Prognosis, Clinica Chimica Acta., vol. 380, Feb. 2007, pp. 208-212.

Murray et al., SU11248 Inhibits Tumor Growth and CSF-1R-dependent Osteolysis in an Experimental Breast Cancer Bone Metastasis Model, Clinical & Experimental Metastasis, vol. 20, Aug. 2003, pp. 757-766.

Ohno et al., A c-Fms Tyrosine Kinase Inhibitor, Ki20227, Suppresses Osteoclast Differentiation and Osteolytic Bone Destruction in a Bone Metastasis, Mol. Cancer Ther., vol. 5, Nov. 2006, pp. 2634-2643.

Ohno et al., The Orally-active and Selective c-FMS tyrosine Kinase Inhibitor Ki20227 Inhibits Disease Progression in a Collagen-induced Arthritis Mouse Model, Eur. J. Immunol., vol. 38, 2008, pp. 283-291.

Paniagua et al., c-Fms-mediated Differentiation and Priming of Monocyte Lineage Cells Plays a Central Role in Autoimmune Arthritis, Arthritis Research & Therapy, vol. 12, No. R32, Feb. 2010, pp. 1-45.

Paulus et al., Colony-stimulating Factor-1 Antibody Reverses Chemoresistance in Human MCF-7 Breast Cancer Xenografts, Cancer Res., vol. 66, No. 8, Apr. 2006, pp. 4349-4356.

Pederson et al., Identification of Breast Cancer Cell Line-derived Paracrine Factors that Stimulate Osteoclast Activity, Cancer Research, vol. 59, Nov. 1999, pp. 5849-5855.

Pixley et al., CSF-1 Regulation of the Wandering Macrophage: Complexity in Action, Trends in Cell Biology, vol. 14, No. 11, Nov. 2004, pp. 628-638.

Prince et al., 8: Disorders of bone and mineral other than osteoporosis, MJA, vol. 180, Apr. 2004, pp. 354-359.

Qiu et al., Primary Structure of c-kit: Relationship with the CSF-1/PDGF Receptor Kinase Family—Oncogenic Activation of v-kit Involves Deletion of Extracellular Domain and C Terminus, The EMBO Journal, vol. 7, No. 4, Jan. 1988, pp. 1003-1011.

R&D Systems, Inc., Recombinant Human M-CSF R/Fc Chimera, Specifications and Use, Catalog No. 329-MR, Nov. 2007, 2 pages.

Rahimi et al., Receptor Chimeras Indicate that the Vascular Endothelial Growth Factor Receptor-1 (VEGFR-1) Modulates Mitogenic Activity of VEGFR-2 in Endothelial Cells, J. Biol. Chem., vol. 275, No. 22, Jun. 2000, pp. 16986-16992.

Ross, M-CSF, c-Fms, and Signaling in Osteoclasts and Their Precursors, Ann. NY Acad. Sci., vol. 1068, 2006, pp. 110-116.

Roussel et al., Colony-stimulating Factor 1-mediated Regulation of a Chimeric c-fms / v-fms Receptor Containing the v-fms-encoded Tyrosine Kinase Domain, PNAS USA, vol. 85, Aug. 1988, pp. 5903-5907.

Sapi, The Role of CSF-1 in Normal Physiology of Mammary Gland and Breast Cancer: An Update, Exp. Biol. Med., vol. 229, 2004, pp. 1-11.

Sarma et al., Macrophage Colony-stimulating Factor Induces Substantial Osteoclast Generation and Bone Resorption in Human Bone Marrow Cultures, Blood, vol. 88, No. 7, Oct. 1996, pp. 2531-2540.

Shaposhnik et al., Arterial Colony Stimulating Factor-1 Influences Atherosclerotic Lesions by Regulating Monocyte Migration and Apoptosis, J. Lipid Research, vol. 51, 2010, pp. 1962-1970.

Sherr et al., Inhibition of Colony-Stimulating Factor-1 Activity by Monoclonal Antibodies to the Human CSF-1 Receptor, Blood, vol. 73, No. 7, May 1989, pp. 1786-1793.

Sherr, Colony-Stimulating Factor-1 Receptor, Blood, vol. 75, No. 1, Jan. 1990, pp. 1-12.

Steinman et al., Virtues and Pitfalls of EAE for the Development of Therapies for Multiple Sclerosis, Trends in Immunology, vol. 26, No. 11, Nov. 2005, pp. 565-571.

Suzuki et al., Differences in Bone Responses to Recombinant Human Granulocyte Colony-stimulating Factor Between Mice and Rats, J. Toxicol. Sci., vol. 33, No. 2, 2008, 245-249.

Sweet et al., CSF-1 as a Regulator of Macrophage Activation and Immune Responses, Archivum Immunologiar et Therapiae Experimentalis, vol. 51, 2003, pp. 169-177.

Tamura et al., Tyrosine Kinases as Targets for Anti-inflammatory Therapy, Anti-Inflammatory & Anti-Allergy Agents in Medicinal Chemistry, vol. 6, No. 1, 2007, pp. 47-60.

Tanaka et al., Macrophage Colony-stimulating Factor is Indispensable for Both Proliferation and Differentiation of Osteoclast Progenitors, J. Clin. Invest., vol. 91, Jan. 1993, pp. 257-263.

Teitelbaum, Osteoclasts: What Do They Do and How Do They Do It?, Am. J. Pathol., vol. 170, No. 2, Feb. 2007, pp. 427-435.

Uemura et al., The Selective M-CSF Receptor Tyrosine Kinase Inhibitor Ki20227 Suppresses Experimental Autoimmune Encephalomyelitis, J. Neuroimmunology, vol. 195, Jan. 2008, pp. 73-80.

Usbiological, CD115, Recombinant, Human, Fc Chimera (BSA Free) (c-fms, Fms, CSF-1R, M-CSFR), from Google's cache of http://usbio.net/Product.spx?ProdSku+C2447-52E1, as retrieved on Jan. 16, 2008 (1 page).

Van Daalen Wetters et al., Random Mutagenesis of CSF-1 Receptor (FMS) Reveals Multiple Sites for Activating Mutations within the Extracellular Domain, The EMBO Journal, vol. 11, No. 2, 1992, pp. 551-557.

Virk et al., Tumor metastasis to bone, Arthritis Research & Therapy, vol. 9, Suppl. 1, 2007, S5, pp. 1-10.

Wang et al., Identification of the Ligand-binding Regions in the Macrophage Colony-stimulating Factor Receptor Extracellular Domain, Mol. Cell Biol., Sep. 1993, pp. 5348-5359.

Wu et al., Enhancement of J6-1 Human Leukemic Cell Proliferation by Membrane-bound M-CSF Through a Cell-Cell Contact Mechanism II. Role of an M-CSF Receptor-like Membrane Protein, Leukemia Research, vol. 22, No. 1, 1998, pp. 55-60.

Wyckoff et al., A Paracrine Loop Between Tumor Cells and Macrophages is Required for Tumor Cell Migration in Mammary Tumors, Cancer Research, vol. 64, Oct. 2004, pp. 7022-7029.

Yano et al., Macrophage Colony-stimulating Factor Gene Transduction into Human Lung Cancer Cells Differentially Regulates Metastasis Formulations in Various Organ Microevents of Natural Killer cell-deplete SCID Mice, Cancer Research, vol. 57, Feb. 1997, pp. 784-790.

Yao et al., Tumor Necrosis Factor-α Increases Circulating Osteoclast Precursor Numbers by Promoting Their Proliferation and Differentiation in the Bone Marrow Through Up-regulation of c-Fms Expression, J. Biol. Chem., vol. 281, No. 17, Apr. 2006, pp. 11846-11855.

Zheng et al., Expression of Bioactive Human M-CSF Soluble Receptor in Transgenic Tobacco Plants, Protein Expression and Purification, vol. 46, 2006, pp. 367-373.

Office Action (Restriction/Election Requirement) mailed Mar. 3, 2011, for co-pending U.S. Appl. No. 12/626,583, 8 pages.

Response to Restriction/Election Requirement, filed May 3, 2011, for co-pending U.S. Appl. No. 12/626,583, 3 pages.

Office Action mailed Jun. 21, 2011, for U.S. Appl. No. 12/626,583 (15 pages).

Reply to Office Action, filed Aug. 1, 2011, for U.S. Appl. No. 12/626,583 (15 pages).

G. Walsh et al., "Post-translational modifications in the context of therapeutic proteins," Nature Biotechnology, 24(10): 1241-1252 (2006).

A. Weihofen et al., "Release of Signal Peptide Fragments into to Cytosol Requires Cleavage in the Transmembrane Region by a Protease Activity That is Specifically Blocked by a Novel Cysteine Protease Inhibitor," J. Biol. Chem., 275(40): 30951-30956 (2000).

* cited by examiner

IC$_{50}$, Inhibition of IL34-Induced Monocyte Proliferation: 0.27 nM
IC$_{50}$, Inhibition of CSF1-Induced Monocyte: 1.5 nM

SEQUENCE LISTING

<160> NUMBER OF SEQ ID NOS: 40

<210> SEQ ID NO 1
<211> LENGTH: 493
<212> TYPE: PRT
<213> ORGANISM: Artificial Sequence
<220> FEATURE:
<223> OTHER INFORMATION: hCSF1R-ECD.512

<400> SEQUENCE: 1

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr

```
                130                 135                 140
Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
                180                 185                 190

Leu Val Arg Ile Arg Gly Glu Ala Ala Gln Ile Val Cys Ser Ala Ser
                195                 200                 205

Ser Val Asp Val Asn Phe Asp Val Phe Leu Gln His Asn Asn Thr Lys
                210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
                275                 280                 285

Asn Leu Ile Gln Glu Val Thr Val Gly Glu Gly Leu Asn Leu Lys Val
                290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
                355                 360                 365

Gly Trp Arg Ala Leu Thr Phe Glu Leu Thr Leu Arg Tyr Pro Pro Glu
                370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
                435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Asp Glu
                485                 490

<210> SEQ ID NO 2
<211> LENGTH: 487
<212> TYPE: PRT
<213> ORGANISM: Artificial Sequence
<220> FEATURE:
<223> OTHER INFORMATION: hCSF1R-ECD.506

<400> SEQUENCE: 2

Ile Pro Val Ile Glu Pro Ser Val Pro Glu Leu Val Val Lys Pro Gly
1               5                   10                  15
```

```
Ala Thr Val Thr Leu Arg Cys Val Gly Asn Gly Ser Val Glu Trp Asp
             20                  25                  30

Gly Pro Pro Ser Pro His Trp Thr Leu Tyr Ser Asp Gly Ser Ser Ser
         35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
```

```
                             435                 440                 445
Val Gln Ser Leu Leu Thr Val Glu Thr Leu Glu His Asn Gln Thr Tyr
            450                 455                 460
Glu Cys Arg Ala His Asn Ser Val Gly Ser Gly Ser Trp Ala Phe Ile
465                 470                 475                 480
Pro Ile Ser Ala Gly Ala His
                485

<210> SEQ ID NO 3
<211> LENGTH: 492
<212> TYPE: PRT
<213> ORGANISM: Artificial Sequence
<220> FEATURE:
<223> OTHER INFORMATION: mCSF1R-ECD.511

<400> SEQUENCE: 3

Ala Pro Val Ile Glu Pro Ser Gly Pro Glu Leu Val Val Glu Pro Gly
1               5                   10                  15
Glu Thr Val Thr Leu Arg Cys Val Ser Asn Gly Ser Val Glu Trp Asp
                20                  25                  30
Gly Pro Ile Ser Pro Tyr Trp Thr Leu Asp Pro Glu Ser Pro Gly Ser
            35                  40                  45
Thr Leu Thr Thr Arg Asn Ala Thr Phe Lys Asn Thr Gly Thr Tyr Arg
        50                  55                  60
Cys Thr Glu Leu Glu Asp Pro Met Ala Gly Ser Thr Thr Ile His Leu
65                  70                  75                  80
Tyr Val Lys Asp Pro Ala His Ser Trp Asn Leu Leu Ala Gln Glu Val
                85                  90                  95
Thr Val Val Glu Gly Gln Glu Ala Val Leu Pro Cys Leu Ile Thr Asp
                100                 105                 110
Pro Ala Leu Lys Asp Ser Val Ser Leu Met Arg Glu Gly Gly Arg Gln
            115                 120                 125
Val Leu Arg Lys Thr Val Tyr Phe Phe Ser Pro Trp Arg Gly Phe Ile
        130                 135                 140
Ile Arg Lys Ala Lys Val Leu Asp Ser Asn Thr Tyr Val Cys Lys Thr
145                 150                 155                 160
Met Val Asn Gly Arg Glu Ser Thr Ser Thr Gly Ile Trp Leu Lys Val
                165                 170                 175
Asn Arg Val His Pro Glu Pro Pro Gln Ile Lys Leu Glu Pro Ser Lys
                180                 185                 190
Leu Val Arg Ile Arg Gly Glu Ala Ala Gln Ile Val Cys Ser Ala Thr
            195                 200                 205
Asn Ala Glu Val Gly Phe Asn Val Ile Leu Lys Arg Gly Asp Thr Lys
        210                 215                 220
Leu Glu Ile Pro Leu Asn Ser Asp Phe Gln Asp Asn Tyr Tyr Lys Lys
225                 230                 235                 240
Val Arg Ala Leu Ser Leu Asn Ala Val Asp Phe Gln Asp Ala Gly Ile
                245                 250                 255
Tyr Ser Cys Val Ala Ser Asn Asp Val Gly Thr Arg Thr Ala Thr Met
                260                 265                 270
Asn Phe Gln Val Val Glu Ser Ala Tyr Leu Asn Leu Thr Ser Glu Gln
            275                 280                 285
Ser Leu Leu Gln Glu Val Ser Val Gly Asp Ser Leu Ile Leu Thr Val
        290                 295                 300
His Ala Asp Ala Tyr Pro Ser Ile Gln His Tyr Asn Trp Thr Tyr Leu
305                 310                 315                 320
```

-continued

```
Gly Pro Phe Phe Glu Asp Gln Arg Lys Leu Glu Phe Ile Thr Gln Arg
            325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
            355                 360                 365

Asn Asn Leu Thr Phe Glu Leu Thr Leu Arg Tyr Pro Pro Glu Val Ser
370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
            405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
            435                 440                 445

Ser Gln Leu Pro Ile Gly Thr Leu Lys His Asn Met Thr Tyr Phe Cys
            450                 455                 460

Lys Thr His Asn Ser Val Gly Asn Ser Ser Gln Tyr Phe Arg Ala Val
465                 470                 475                 480

Ser Leu Gly Gln Ser Lys Gln Leu Pro Asp Glu Ser
            485                 490
```

<210> SEQ ID NO 4
<211> LENGTH: 487
<212> TYPE: PRT
<213> ORGANISM: Artificial Sequence
<220> FEATURE:
<223> OTHER INFORMATION: mCSF1R-ECD.506

<400> SEQUENCE: 4

```
Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
            85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
            165                 170                 175

Asn Arg Val His Pro Glu Pro Pro Gln Ile Lys Leu Glu Pro Ser Lys
            180                 185                 190
```

```
Leu Val Arg Ile Arg Gly Glu Ala Ala Gln Ile Val Cys Ser Ala Thr
    195                 200                 205

Asn Ala Glu Val Gly Phe Asn Val Ile Leu Lys Arg Gly Asp Thr Lys
210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285

Ser Leu Leu Gln Glu Val Ser Val Gly Asp Ser Leu Ile Leu Thr Val
    290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
        355                 360                 365

Asn Asn Leu Thr Phe Glu Leu Thr Leu Arg Tyr Pro Pro Glu Val Ser
    370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
        435                 440                 445

Ser Gln Leu Pro Ile Gly Thr Leu Lys His Asn Met Thr Tyr Phe Cys
    450                 455                 460

Lys Thr His Asn Ser Val Gly Asn Ser Ser Gln Tyr Phe Arg Ala Val
465                 470                 475                 480

Ser Leu Gly Gln Ser Lys Gln
                485

<210> SEQ ID NO 5
<211> LENGTH: 725
<212> TYPE: PRT
<213> ORGANISM: Artificial Sequence
<220> FEATURE:
<223> OTHER INFORMATION: hCSF1R-ECD.512-Fc

<400> SEQUENCE: 5

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
```

```
                 65                  70                  75                  80
Tyr Val Lys Asp Pro Ala Arg Pro Trp Asn Val Leu Ala Gln Glu Val
                     85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
        130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Glu Pro Lys
                485                 490                 495
```

```
Ser Ser Asp Lys Thr His Thr Cys Pro Pro Cys Pro Ala Pro Glu Leu
            500                 505                 510
Leu Gly Gly Pro Ser Val Phe Leu Phe Pro Pro Lys Pro Lys Asp Thr
        515                 520                 525
Leu Met Ile Ser Arg Thr Pro Glu Val Thr Cys Val Val Val Asp Val
    530                 535                 540
Ser His Glu Asp Pro Glu Val Lys Phe Asn Trp Tyr Val Asp Gly Val
545                 550                 555                 560
Glu Val His Asn Ala Lys Thr Lys Pro Arg Glu Glu Gln Tyr Asn Ser
                565                 570                 575
Thr Tyr Arg Val Val Ser Val Leu Thr Val Leu His Gln Asp Trp Leu
            580                 585                 590
Asn Gly Lys Glu Tyr Lys Cys Lys Val Ser Asn Lys Ala Leu Pro Ala
        595                 600                 605
Pro Ile Glu Lys Thr Ile Ser Lys Ala Lys Gly Gln Pro Arg Glu Pro
    610                 615                 620
Gln Val Tyr Thr Leu Pro Pro Ser Arg Asp Glu Leu Thr Lys Asn Gln
625                 630                 635                 640
Val Ser Leu Thr Cys Leu Val Lys Gly Phe Tyr Pro Ser Asp Ile Ala
                645                 650                 655
Val Glu Trp Glu Ser Asn Gly Gln Pro Glu Asn Asn Tyr Lys Thr Thr
            660                 665                 670
Pro Pro Val Leu Asp Ser Asp Gly Ser Phe Phe Leu Tyr Ser Lys Leu
        675                 680                 685
Thr Val Asp Lys Ser Arg Trp Gln Gln Gly Asn Val Phe Ser Cys Ser
    690                 695                 700
Val Met His Glu Ala Leu His Asn His Tyr Thr Gln Lys Ser Leu Ser
705                 710                 715                 720
Leu Ser Pro Gly Lys
            725

<210> SEQ ID NO 6
<211> LENGTH: 719
<212> TYPE: PRT
<213> ORGANISM: Artificial Sequence
<220> FEATURE:
<223> OTHER INFORMATION: hCSF1R-ECD.506-Fc

<400> SEQUENCE: 6

Ile Pro Val Ile Glu Pro Ser Val Pro Glu Leu Val Val Lys Pro Gly
1               5                   10                  15
Ala Thr Val Thr Leu Arg Cys Val Gly Asn Gly Ser Val Glu Trp Asp
            20                  25                  30
Gly Pro Pro Ser Pro His Trp Thr Leu Tyr Ser Asp Gly Ser Ser Ser
        35                  40                  45
Ile Leu Ser Thr Asn Asn Ala Thr Phe Gln Asn Thr Gly Thr Tyr Arg
    50                  55                  60
Cys Thr Glu Pro Gly Asp Pro Leu Gly Gly Ser Ala Ala Ile His Leu
65                  70                  75                  80
Tyr Val Lys Asp Pro Ala Arg Pro Trp Asn Val Leu Ala Gln Glu Val
                85                  90                  95
Val Val Phe Glu Asp Gln Asp Ala Leu Leu Pro Cys Leu Leu Thr Asp
            100                 105                 110
Pro Val Leu Glu Ala Gly Val Ser Leu Val Arg Val Arg Gly Arg Pro
        115                 120                 125
Leu Met Arg His Thr Asn Tyr Ser Phe Ser Pro Trp His Gly Phe Thr
```

```
                130             135             140
Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
                180                 185                 190

Leu Val Arg Ile Arg Gly Glu Ala Ala Gln Ile Val Cys Ser Ala Ser
                195                 200                 205

Ser Val Asp Val Asn Phe Asp Val Phe Leu Gln His Asn Asn Thr Lys
                210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
                275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
                355                 360                 365

Gly Trp Arg Ala Leu Thr Phe Glu Leu Thr Leu Arg Tyr Pro Pro Glu
                370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
                435                 440                 445

Val Gln Ser Leu Leu Thr Val Glu Thr Leu Glu His Asn Gln Thr Tyr
                450                 455                 460

Glu Cys Arg Ala His Asn Ser Val Gly Ser Gly Ser Trp Ala Phe Ile
465                 470                 475                 480

Pro Ile Ser Ala Gly Ala His Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
                515                 520                 525

Pro Glu Val Thr Cys Val Val Val Asp Val Ser His Glu Asp Pro Glu
                530                 535                 540

Val Lys Phe Asn Trp Tyr Val Asp Gly Val Glu Val His Asn Ala Lys
545                 550                 555                 560
```

-continued

```
Thr Lys Pro Arg Glu Glu Gln Tyr Asn Ser Thr Tyr Arg Val Val Ser
            565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
            610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
            645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
            690                 695                 700

His Asn His Tyr Thr Gln Lys Ser Leu Ser Leu Ser Pro Gly Lys
705                 710                 715

<210> SEQ ID NO 7
<211> LENGTH: 724
<212> TYPE: PRT
<213> ORGANISM: Artificial Sequence
<220> FEATURE:
<223> OTHER INFORMATION: mCSF1R-ECD.511-Fc

<400> SEQUENCE: 7

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
            35                  40                  45

Thr Leu Thr Thr Arg Asn Ala Thr Phe Lys Asn Thr Gly Thr Tyr Arg
        50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
            85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
            115                 120                 125

Val Leu Arg Lys Thr Val Tyr Phe Phe Ser Pro Trp Arg Gly Phe Ile
        130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
            165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
```

```
               210                 215                 220
Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
                260                 265                 270

Asn Phe Gln Val Val Glu Ser Ala Tyr Leu Asn Leu Thr Ser Glu Gln
                275                 280                 285

Ser Leu Leu Gln Glu Val Ser Val Gly Asp Ser Leu Ile Leu Thr Val
290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
                340                 345                 350

Ser Glu Ala Gly Gln Tyr Phe Leu Met Ala Gln Asn Lys Ala Gly Trp
                355                 360                 365

Asn Asn Leu Thr Phe Glu Leu Thr Leu Arg Tyr Pro Pro Glu Val Ser
370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
                420                 425                 430

His Pro Glu Val Leu Ser Gln Lys Pro Phe Asp Lys Val Ile Ile Gln
                435                 440                 445

Ser Gln Leu Pro Ile Gly Thr Leu Lys His Asn Met Thr Tyr Phe Cys
450                 455                 460

Lys Thr His Asn Ser Val Gly Asn Ser Ser Gln Tyr Phe Arg Ala Val
465                 470                 475                 480

Ser Leu Gly Gln Ser Lys Gln Leu Pro Asp Glu Ser Glu Pro Lys Ser
                485                 490                 495

Ser Asp Lys Thr His Thr Cys Pro Pro Cys Pro Ala Pro Glu Leu Leu
                500                 505                 510

Gly Gly Pro Ser Val Phe Leu Phe Pro Pro Lys Pro Lys Asp Thr Leu
                515                 520                 525

Met Ile Ser Arg Thr Pro Glu Val Thr Cys Val Val Val Asp Val Ser
530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
                565                 570                 575

Tyr Arg Val Val Ser Val Leu Thr Val Leu His Gln Asp Trp Leu Asn
                580                 585                 590

Gly Lys Glu Tyr Lys Cys Lys Val Ser Asn Lys Ala Leu Pro Ala Pro
                595                 600                 605

Ile Glu Lys Thr Ile Ser Lys Ala Lys Gly Gln Pro Arg Glu Pro Gln
                610                 615                 620

Val Tyr Thr Leu Pro Pro Ser Arg Asp Glu Leu Thr Lys Asn Gln Val
625                 630                 635                 640
```

```
Ser Leu Thr Cys Leu Val Lys Gly Phe Tyr Pro Ser Asp Ile Ala Val
            645                 650                 655

Glu Trp Glu Ser Asn Gly Gln Pro Glu Asn Asn Tyr Lys Thr Thr Pro
        660                 665                 670

Pro Val Leu Asp Ser Asp Gly Ser Phe Phe Leu Tyr Ser Lys Leu Thr
            675                 680                 685

Val Asp Lys Ser Arg Trp Gln Gln Gly Asn Val Phe Ser Cys Ser Val
        690                 695                 700

Met His Glu Ala Leu His Asn His Tyr Thr Gln Lys Ser Leu Ser Leu
705                 710                 715                 720

Ser Pro Gly Lys

<210> SEQ ID NO 8
<211> LENGTH: 719
<212> TYPE: PRT
<213> ORGANISM: Artificial Sequence
<220> FEATURE:
<223> OTHER INFORMATION: mCSF1R-ECD.506-Fc

<400> SEQUENCE: 8

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285
```

-continued

Ser Leu Leu Gln Glu Val Ser Val Gly Asp Ser Leu Ile Leu Thr Val
    290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
                340                 345                 350

Ser Glu Ala Gly Gln Tyr Phe Leu Met Ala Gln Asn Lys Ala Gly Trp
                355                 360                 365

Asn Asn Leu Thr Phe Glu Leu Thr Leu Arg Tyr Pro Pro Glu Val Ser
    370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
                420                 425                 430

His Pro Glu Val Leu Ser Gln Lys Pro Phe Asp Lys Val Ile Ile Gln
                435                 440                 445

Ser Gln Leu Pro Ile Gly Thr Leu Lys His Asn Met Thr Tyr Phe Cys
    450                 455                 460

Lys Thr His Asn Ser Val Gly Asn Ser Ser Gln Tyr Phe Arg Ala Val
465                 470                 475                 480

Ser Leu Gly Gln Ser Lys Gln Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
                515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Ala Leu Pro Ala Pro Ile Glu Lys Thr Ile
                595                 600                 605

Ser Lys Ala Lys Gly Gln Pro Arg Glu Pro Gln Val Tyr Thr Leu Pro
    610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
                675                 680                 685

Trp Gln Gln Gly Asn Val Phe Ser Cys Ser Val Met His Glu Ala Leu
    690                 695                 700

His Asn His Tyr Thr Gln Lys Ser Leu Ser Leu Ser Pro Gly Lys

-continued

```
705                 710                 715

<210> SEQ ID NO 9
<211> LENGTH: 19
<212> TYPE: PRT
<213> ORGANISM: Artificial Sequence
<220> FEATURE:
<223> OTHER INFORMATION: hCSF1R signal peptide

<400> SEQUENCE: 9

Met Gly Pro Gly Val Leu Leu Leu Leu Val Ala Thr Ala Trp His
1               5                   10                  15

Gly Gln Gly

<210> SEQ ID NO 10
<211> LENGTH: 19
<212> TYPE: PRT
<213> ORGANISM: Artificial Sequence
<220> FEATURE:
<223> OTHER INFORMATION: mCSF1R signal peptide

<400> SEQUENCE: 10

Met Glu Leu Gly Pro Pro Leu Val Leu Leu Leu Ala Thr Val Trp His
1               5                   10                  15

Gly Gln Gly

<210> SEQ ID NO 11
<211> LENGTH: 512
<212> TYPE: PRT
<213> ORGANISM: Artificial Sequence
<220> FEATURE:
<223> OTHER INFORMATION: hCSF1R-ECD.512 with signal peptide

<400> SEQUENCE: 11

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205
```

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
    435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

<210> SEQ ID NO 12
<211> LENGTH: 506
<212> TYPE: PRT
<213> ORGANISM: Artificial Sequence
<220> FEATURE:
<223> OTHER INFORMATION: hCSF1R-ECD.506 with signal peptide

<400> SEQUENCE: 12

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
                50                  55                  60

-continued

```
Ser Ser Ser Ile Leu Ser Thr Asn Asn Ala Thr Phe Gln Asn Thr Gly
 65                  70                  75                  80

Thr Tyr Arg Cys Thr Glu Pro Gly Asp Pro Leu Gly Gly Ser Ala Ala
                 85                  90                  95

Ile His Leu Tyr Val Lys Asp Pro Ala Arg Pro Trp Asn Val Leu Ala
            100                 105                 110

Gln Glu Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gly Val Leu Gln
        435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495
```

```
Ala Phe Ile Pro Ile Ser Ala Gly Ala His
                500                 505

<210> SEQ ID NO 13
<211> LENGTH: 511
<212> TYPE: PRT
<213> ORGANISM: Artificial Sequence
<220> FEATURE:
<223> OTHER INFORMATION: mCSF1R-ECD.511 with signal peptide

<400> SEQUENCE: 13

Met Glu Leu Gly Pro Leu Val Leu Leu Ala Thr Val Trp His
1               5                   10                  15

Gly Gln Gly Ala Pro Val Ile Glu Pro Ser Gly Pro Glu Leu Val Val
                20                  25                  30

Glu Pro Gly Glu Thr Val Thr Leu Arg Cys Val Ser Asn Gly Ser Val
            35                  40                  45

Glu Trp Asp Gly Pro Ile Ser Pro Tyr Trp Thr Leu Asp Pro Glu Ser
    50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
            100                 105                 110

Gln Glu Val Thr Val Val Glu Gly Gln Glu Ala Val Leu Pro Cys Leu
        115                 120                 125

Ile Thr Asp Pro Ala Leu Lys Asp Ser Val Ser Leu Met Arg Glu Gly
130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
            180                 185                 190

Leu Lys Val Asn Arg Val His Pro Glu Pro Pro Gln Ile Lys Leu Glu
        195                 200                 205

Pro Ser Lys Leu Val Arg Ile Arg Gly Glu Ala Ala Gln Ile Val Cys
210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350
```

```
Thr Gln Arg Ala Ile Tyr Arg Tyr Thr Phe Lys Leu Phe Leu Asn Arg
    355                 360                 365

Val Lys Ala Ser Glu Ala Gly Gln Tyr Phe Leu Met Ala Gln Asn Lys
    370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                    405                 410                 415

Cys Asp Val Ser Gly Tyr Pro Gln Pro Ser Val Thr Trp Met Glu Cys
                420                 425                 430

Arg Gly His Thr Asp Arg Cys Asp Glu Ala Gln Ala Leu Gln Val Trp
            435                 440                 445

Asn Asp Thr His Pro Glu Val Leu Ser Gln Lys Pro Phe Asp Lys Val
        450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Leu Pro Asp Glu Ser
                500                 505                 510

<210> SEQ ID NO 14
<211> LENGTH: 506
<212> TYPE: PRT
<213> ORGANISM: Artificial Sequence
<220> FEATURE:
<223> OTHER INFORMATION: mCSF1R-ECD.506 with signal peptide

<400> SEQUENCE: 14

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
                20                  25                  30

Glu Pro Gly Glu Thr Val Thr Leu Arg Cys Val Ser Asn Gly Ser Val
                35                  40                  45

Glu Trp Asp Gly Pro Ile Ser Pro Tyr Trp Thr Leu Asp Pro Glu Ser
    50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
                100                 105                 110

Gln Glu Val Thr Val Glu Gly Gln Glu Ala Val Leu Pro Cys Leu
                115                 120                 125

Ile Thr Asp Pro Ala Leu Lys Asp Ser Val Ser Leu Met Arg Glu Gly
    130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
                180                 185                 190

Leu Lys Val Asn Arg Val His Pro Glu Pro Pro Gln Ile Lys Leu Glu
            195                 200                 205

Pro Ser Lys Leu Val Arg Ile Arg Gly Glu Ala Ala Gln Ile Val Cys
```

```
            210                 215                 220
Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
    290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350

Thr Gln Arg Ala Ile Tyr Arg Tyr Thr Phe Lys Leu Phe Leu Asn Arg
        355                 360                 365

Val Lys Ala Ser Glu Ala Gly Gln Tyr Phe Leu Met Ala Gln Asn Lys
    370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
        435                 440                 445

Asn Asp Thr His Pro Glu Val Leu Ser Gln Lys Pro Phe Asp Lys Val
    450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln
            500                 505

<210> SEQ ID NO 15
<211> LENGTH: 744
<212> TYPE: PRT
<213> ORGANISM: Artificial Sequence
<220> FEATURE:
<223> OTHER INFORMATION: hCSF1R-ECD.512-Fc with signal peptide

<400> SEQUENCE: 15

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80
```

```
Thr Tyr Arg Cys Thr Glu Pro Gly Asp Pro Leu Gly Ser Ala Ala
                85                  90                  95

Ile His Leu Tyr Val Lys Asp Pro Ala Arg Pro Trp Asn Val Leu Ala
               100                 105                 110

Gln Glu Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
            130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
```

```
                    500                 505                 510
Glu Pro Lys Ser Ser Asp Lys Thr His Thr Cys Pro Pro Cys Pro Ala
            515                 520                 525

Pro Glu Leu Leu Gly Gly Pro Ser Val Phe Leu Phe Pro Pro Lys Pro
        530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
            580                 585                 590

Tyr Asn Ser Thr Tyr Arg Val Val Ser Val Leu Thr Val Leu His Gln
        595                 600                 605

Asp Trp Leu Asn Gly Lys Glu Tyr Lys Cys Lys Val Ser Asn Lys Ala
    610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
                645                 650                 655

Lys Asn Gln Val Ser Leu Thr Cys Leu Val Lys Gly Phe Tyr Pro Ser
            660                 665                 670

Asp Ile Ala Val Glu Trp Glu Ser Asn Gly Gln Pro Glu Asn Asn Tyr
        675                 680                 685

Lys Thr Thr Pro Pro Val Leu Asp Ser Asp Gly Ser Phe Phe Leu Tyr
    690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
            740

<210> SEQ ID NO 16
<211> LENGTH: 738
<212> TYPE: PRT
<213> ORGANISM: Artificial Sequence
<220> FEATURE:
<223> OTHER INFORMATION: hCSF1R-ECD.506-Fc with signal peptide

<400> SEQUENCE: 16

Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125
```

```
Leu Thr Asp Pro Val Leu Glu Ala Gly Val Ser Leu Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Glu Pro Lys Ser Ser Asp
            500                 505                 510

Lys Thr His Thr Cys Pro Pro Cys Pro Ala Pro Glu Leu Leu Gly Gly
        515                 520                 525

Pro Ser Val Phe Leu Phe Pro Pro Lys Pro Lys Asp Thr Leu Met Ile
    530                 535                 540

Ser Arg Thr Pro Glu Val Thr Cys Val Val Asp Val Ser His Glu
```

```
545                 550                 555                 560
Asp Pro Glu Val Lys Phe Asn Trp Tyr Val Asp Gly Val Glu Val His
                565                 570                 575

Asn Ala Lys Thr Lys Pro Arg Glu Glu Gln Tyr Asn Ser Thr Tyr Arg
                580                 585                 590

Val Val Ser Val Leu Thr Val Leu His Gln Asp Trp Leu Asn Gly Lys
                595                 600                 605

Glu Tyr Lys Cys Lys Val Ser Asn Lys Ala Leu Pro Ala Pro Ile Glu
                610                 615                 620

Lys Thr Ile Ser Lys Ala Lys Gly Gln Pro Arg Glu Pro Gln Val Tyr
625                 630                 635                 640

Thr Leu Pro Pro Ser Arg Asp Glu Leu Thr Lys Asn Gln Val Ser Leu
                645                 650                 655

Thr Cys Leu Val Lys Gly Phe Tyr Pro Ser Asp Ile Ala Val Glu Trp
                660                 665                 670

Glu Ser Asn Gly Gln Pro Glu Asn Asn Tyr Lys Thr Thr Pro Pro Val
                675                 680                 685

Leu Asp Ser Asp Gly Ser Phe Phe Leu Tyr Ser Lys Leu Thr Val Asp
690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
                725                 730                 735

Gly Lys

<210> SEQ ID NO 17
<211> LENGTH: 743
<212> TYPE: PRT
<213> ORGANISM: Artificial Sequence
<220> FEATURE:
<223> OTHER INFORMATION: mCSF1R-ECD.511-Fc with signal peptide

<400> SEQUENCE: 17

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
                20                  25                  30

Glu Pro Gly Glu Thr Val Thr Leu Arg Cys Val Ser Asn Gly Ser Val
                35                  40                  45

Glu Trp Asp Gly Pro Ile Ser Pro Tyr Trp Thr Leu Asp Pro Glu Ser
                50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
                100                 105                 110

Gln Glu Val Thr Val Val Glu Gly Gln Glu Ala Val Leu Pro Cys Leu
                115                 120                 125

Ile Thr Asp Pro Ala Leu Lys Asp Ser Val Ser Leu Met Arg Glu Gly
                130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175
```

-continued

Cys Lys Thr Met Val Asn Gly Arg Glu Ser Thr Ser Thr Gly Ile Trp
            180                 185                 190

Leu Lys Val Asn Arg Val His Pro Glu Pro Gln Ile Lys Leu Glu
        195                 200                 205

Pro Ser Lys Leu Val Arg Ile Arg Gly Glu Ala Ala Gln Ile Val Cys
210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
    290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350

Thr Gln Arg Ala Ile Tyr Arg Tyr Thr Phe Lys Leu Phe Leu Asn Arg
        355                 360                 365

Val Lys Ala Ser Glu Ala Gly Gln Tyr Phe Leu Met Ala Gln Asn Lys
    370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
        435                 440                 445

Asn Asp Thr His Pro Glu Val Leu Ser Gln Lys Pro Phe Asp Lys Val
    450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Leu Pro Asp Glu Ser Glu
            500                 505                 510

Pro Lys Ser Ser Asp Lys Thr His Thr Cys Pro Pro Cys Pro Ala Pro
        515                 520                 525

Glu Leu Leu Gly Gly Pro Ser Val Phe Leu Phe Pro Pro Lys Pro Lys
    530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
            580                 585                 590

Asn Ser Thr Tyr Arg Val Val Ser Val Leu Thr Val Leu His Gln Asp
        595                 600                 605

```
Trp Leu Asn Gly Lys Glu Tyr Lys Cys Lys Val Ser Asn Lys Ala Leu
    610                 615                 620
Pro Ala Pro Ile Glu Lys Thr Ile Ser Lys Ala Lys Gly Gln Pro Arg
625                 630                 635                 640
Glu Pro Gln Val Tyr Thr Leu Pro Pro Ser Arg Asp Glu Leu Thr Lys
                645                 650                 655
Asn Gln Val Ser Leu Thr Cys Leu Val Lys Gly Phe Tyr Pro Ser Asp
                660                 665                 670
Ile Ala Val Glu Trp Glu Ser Asn Gly Gln Pro Glu Asn Asn Tyr Lys
            675                 680                 685
Thr Thr Pro Pro Val Leu Asp Ser Asp Gly Ser Phe Phe Leu Tyr Ser
690                 695                 700
Lys Leu Thr Val Asp Lys Ser Arg Trp Gln Gln Gly Asn Val Phe Ser
705                 710                 715                 720
Cys Ser Val Met His Glu Ala Leu His Asn His Tyr Thr Gln Lys Ser
                725                 730                 735
Leu Ser Leu Ser Pro Gly Lys
                740

<210> SEQ ID NO 18
<211> LENGTH: 738
<212> TYPE: PRT
<213> ORGANISM: Artificial Sequence
<220> FEATURE:
<223> OTHER INFORMATION: mCSF1R-ECD.506-Fc with signal peptide

<400> SEQUENCE: 18

Met Glu Leu Gly Pro Pro Leu Val Leu Leu Leu Ala Thr Val Trp His
1               5                   10                  15
Gly Gln Gly Ala Pro Val Ile Glu Pro Ser Gly Pro Glu Leu Val Val
                20                  25                  30
Glu Pro Gly Glu Thr Val Thr Leu Arg Cys Val Ser Asn Gly Ser Val
            35                  40                  45
Glu Trp Asp Gly Pro Ile Ser Pro Tyr Trp Thr Leu Asp Pro Glu Ser
50                  55                  60
Pro Gly Ser Thr Leu Thr Thr Arg Asn Ala Thr Phe Lys Asn Thr Gly
65                  70                  75                  80
Thr Tyr Arg Cys Thr Glu Leu Glu Asp Pro Met Ala Gly Ser Thr Thr
                85                  90                  95
Ile His Leu Tyr Val Lys Asp Pro Ala His Ser Trp Asn Leu Leu Ala
            100                 105                 110
Gln Glu Val Thr Val Val Glu Gly Gln Glu Ala Val Leu Pro Cys Leu
        115                 120                 125
Ile Thr Asp Pro Ala Leu Lys Asp Ser Val Ser Leu Met Arg Glu Gly
    130                 135                 140
Gly Arg Gln Val Leu Arg Lys Thr Val Tyr Phe Phe Ser Pro Trp Arg
145                 150                 155                 160
Gly Phe Ile Ile Arg Lys Ala Lys Val Leu Asp Ser Asn Thr Tyr Val
                165                 170                 175
Cys Lys Thr Met Val Asn Gly Arg Glu Ser Thr Ser Thr Gly Ile Trp
            180                 185                 190
Leu Lys Val Asn Arg Val His Pro Glu Pro Pro Gln Ile Lys Leu Glu
        195                 200                 205
Pro Ser Lys Leu Val Arg Ile Arg Gly Glu Ala Ala Gln Ile Val Cys
    210                 215                 220
```

-continued

```
Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
            245                 250                 255

Tyr Lys Lys Val Arg Ala Leu Ser Leu Asn Ala Val Asp Phe Gln Asp
        260                 265                 270

Ala Gly Ile Tyr Ser Cys Val Ala Ser Asn Asp Val Gly Thr Arg Thr
    275                 280                 285

Ala Thr Met Asn Phe Gln Val Glu Ser Ala Tyr Leu Asn Leu Thr
290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350

Thr Gln Arg Ala Ile Tyr Arg Tyr Thr Phe Lys Leu Phe Leu Asn Arg
        355                 360                 365

Val Lys Ala Ser Glu Ala Gly Gln Tyr Phe Leu Met Ala Gln Asn Lys
    370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
        435                 440                 445

Asn Asp Thr His Pro Glu Val Leu Ser Gln Lys Pro Phe Asp Lys Val
    450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Glu Pro Lys Ser Ser Asp
            500                 505                 510

Lys Thr His Thr Cys Pro Pro Cys Pro Ala Pro Glu Leu Leu Gly Gly
        515                 520                 525

Pro Ser Val Phe Leu Phe Pro Pro Lys Pro Lys Asp Thr Leu Met Ile
    530                 535                 540

Ser Arg Thr Pro Glu Val Thr Cys Val Val Val Asp Val Ser His Glu
545                 550                 555                 560

Asp Pro Glu Val Lys Phe Asn Trp Tyr Val Asp Gly Val Glu Val His
                565                 570                 575

Asn Ala Lys Thr Lys Pro Arg Glu Glu Gln Tyr Asn Ser Thr Tyr Arg
            580                 585                 590

Val Val Ser Val Leu Thr Val Leu His Gln Asp Trp Leu Asn Gly Lys
        595                 600                 605

Glu Tyr Lys Cys Lys Val Ser Asn Lys Ala Leu Pro Ala Pro Ile Glu
    610                 615                 620

Lys Thr Ile Ser Lys Ala Lys Gly Gln Pro Arg Glu Pro Gln Val Tyr
625                 630                 635                 640

Thr Leu Pro Pro Ser Arg Asp Glu Leu Thr Lys Asn Gln Val Ser Leu
                645                 650                 655
```

```
Thr Cys Leu Val Lys Gly Phe Tyr Pro Ser Asp Ile Ala Val Glu Trp
            660                 665                 670

Glu Ser Asn Gly Gln Pro Glu Asn Asn Tyr Lys Thr Thr Pro Pro Val
            675                 680                 685

Leu Asp Ser Asp Gly Ser Phe Phe Leu Tyr Ser Lys Leu Thr Val Asp
            690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
            725                 730                 735

Gly Lys

<210> SEQ ID NO 19
<211> LENGTH: 232
<212> TYPE: PRT
<213> ORGANISM: Artificial Sequence
<220> FEATURE:
<223> OTHER INFORMATION: Fc C237S

<400> SEQUENCE: 19

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 20
<211> LENGTH: 228
<212> TYPE: PRT
<213> ORGANISM: Artificial Sequence
<220> FEATURE:
<223> OTHER INFORMATION: Exemplary Fc #1
```

```
<400> SEQUENCE: 20

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 21
<211> LENGTH: 229
<212> TYPE: PRT
<213> ORGANISM: Artificial Sequence
<220> FEATURE:
<223> OTHER INFORMATION: Exemplary Fc #2

<400> SEQUENCE: 21

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
```

```
              115                 120                 125
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 22
<211> LENGTH: 953
<212> TYPE: PRT
<213> ORGANISM: Artificial Sequence
<220> FEATURE:
<223> OTHER INFORMATION: hCSF1R (full-length, no signal peptide)

<400> SEQUENCE: 22

Ile Pro Val Ile Glu Pro Ser Val Pro Glu Leu Val Val Lys Pro Gly
1               5                  10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255
```

```
Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
            290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
            325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
            370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
            450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
            485                 490                 495

Thr Pro Val Val Val Ala Cys Met Ser Ile Met Ala Leu Leu Leu Leu
            500                 505                 510

Leu Leu Leu Leu Leu Leu Tyr Lys Tyr Lys Gln Lys Pro Lys Tyr Gln
            515                 520                 525

Val Arg Trp Lys Ile Ile Glu Ser Tyr Glu Gly Asn Ser Tyr Thr Phe
            530                 535                 540

Ile Asp Pro Thr Gln Leu Pro Tyr Asn Glu Lys Trp Glu Phe Pro Arg
545                 550                 555                 560

Asn Asn Leu Gln Phe Gly Lys Thr Leu Gly Ala Gly Ala Phe Gly Lys
            565                 570                 575

Val Val Glu Ala Thr Ala Phe Gly Leu Gly Lys Glu Asp Ala Val Leu
            580                 585                 590

Lys Val Ala Val Lys Met Leu Lys Ser Thr Ala His Ala Asp Glu Lys
            595                 600                 605

Glu Ala Leu Met Ser Glu Leu Lys Ile Met Ser His Leu Gly Gln His
            610                 615                 620

Glu Asn Ile Val Asn Leu Leu Gly Ala Cys Thr His Gly Gly Pro Val
625                 630                 635                 640

Leu Val Ile Thr Glu Tyr Cys Cys Tyr Gly Asp Leu Leu Asn Phe Leu
            645                 650                 655

Arg Arg Lys Ala Glu Ala Met Leu Gly Pro Ser Leu Ser Pro Gly Gln
            660                 665                 670

Asp Pro Glu Gly Gly Val Asp Tyr Lys Asn Ile His Leu Glu Lys Lys
```

```
               675                 680                 685
Tyr Val Arg Arg Asp Ser Gly Phe Ser Ser Gln Gly Val Asp Thr Tyr
690                 695                 700

Val Glu Met Arg Pro Val Ser Thr Ser Ser Asn Asp Ser Phe Ser Glu
705                 710                 715                 720

Gln Asp Leu Asp Lys Glu Asp Gly Arg Pro Leu Glu Leu Arg Asp Leu
                725                 730                 735

Leu His Phe Ser Ser Gln Val Ala Gln Gly Met Ala Phe Leu Ala Ser
                740                 745                 750

Lys Asn Cys Ile His Arg Asp Val Ala Ala Arg Asn Val Leu Leu Thr
            755                 760                 765

Asn Gly His Val Ala Lys Ile Gly Asp Phe Gly Leu Ala Arg Asp Ile
        770                 775                 780

Met Asn Asp Ser Asn Tyr Ile Val Lys Gly Asn Ala Arg Leu Pro Val
785                 790                 795                 800

Lys Trp Met Ala Pro Glu Ser Ile Phe Asp Cys Val Tyr Thr Val Gln
                805                 810                 815

Ser Asp Val Trp Ser Tyr Gly Ile Leu Leu Trp Glu Ile Phe Ser Leu
                820                 825                 830

Gly Leu Asn Pro Tyr Pro Gly Ile Leu Val Asn Ser Lys Phe Tyr Lys
                835                 840                 845

Leu Val Lys Asp Gly Tyr Gln Met Ala Gln Pro Ala Phe Ala Pro Lys
            850                 855                 860

Asn Ile Tyr Ser Ile Met Gln Ala Cys Trp Ala Leu Glu Pro Thr His
865                 870                 875                 880

Arg Pro Thr Phe Gln Gln Ile Cys Ser Phe Leu Gln Glu Gln Ala Gln
                885                 890                 895

Glu Asp Arg Arg Glu Arg Asp Tyr Thr Asn Leu Pro Ser Ser Ser Arg
                900                 905                 910

Ser Gly Gly Ser Gly Ser Ser Ser Glu Leu Glu Glu Glu Ser Ser
            915                 920                 925

Ser Glu His Leu Thr Cys Cys Glu Gln Gly Asp Ile Ala Gln Pro Leu
        930                 935                 940

Leu Gln Pro Asn Asn Tyr Gln Phe Cys
945                 950

<210> SEQ ID NO 23
<211> LENGTH: 972
<212> TYPE: PRT
<213> ORGANISM: Artificial Sequence
<220> FEATURE:
<223> OTHER INFORMATION: hCSF1R (full-length, + signal peptide)

<400> SEQUENCE: 23

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95
```

-continued

```
Ile His Leu Tyr Val Lys Asp Pro Ala Arg Pro Trp Asn Val Leu Ala
            100                 105                 110
Gln Glu Val Val Phe Glu Asp Gln Asp Ala Leu Leu Pro Cys Leu
        115                 120                 125
Leu Thr Asp Pro Val Leu Glu Ala Gly Val Ser Leu Val Arg Val Arg
130                 135                 140
Gly Arg Pro Leu Met Arg His Thr Asn Tyr Ser Phe Ser Pro Trp His
145                 150                 155                 160
Gly Phe Thr Ile His Arg Ala Lys Phe Ile Gln Ser Gln Asp Tyr Gln
                165                 170                 175
Cys Ser Ala Leu Met Gly Gly Arg Lys Val Met Ser Ile Ser Ile Arg
            180                 185                 190
Leu Lys Val Gln Lys Val Ile Pro Gly Pro Pro Ala Leu Thr Leu Val
        195                 200                 205
Pro Ala Glu Leu Val Arg Ile Arg Gly Glu Ala Ala Gln Ile Val Cys
210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
            260                 265                 270
Ala Gly Asn Tyr Ser Cys Val Ala Ser Asn Val Gln Gly Lys His Ser
        275                 280                 285
Thr Ser Met Phe Phe Arg Val Val Glu Ser Ala Tyr Leu Asn Leu Ser
290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
            340                 345                 350
Asn Ala Thr Thr Lys Asp Thr Tyr Arg His Thr Phe Thr Leu Ser Leu
        355                 360                 365
Pro Arg Leu Lys Pro Ser Glu Ala Gly Arg Tyr Ser Phe Leu Ala Arg
370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
            420                 425                 430
Gln Cys Ser Gly His Thr Asp Arg Cys Asp Glu Ala Gln Val Leu Gln
        435                 440                 445
Val Trp Asp Asp Pro Tyr Pro Glu Val Leu Ser Gln Glu Pro Phe His
450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
            500                 505                 510
Phe Leu Phe Thr Pro Val Val Val Ala Cys Met Ser Ile Met Ala Leu
```

```
            515                 520                 525
Leu Leu Leu Leu Leu Leu Leu Leu Leu Tyr Lys Tyr Lys Gln Lys Pro
            530                 535                 540
Lys Tyr Gln Val Arg Trp Lys Ile Ile Glu Ser Tyr Glu Gly Asn Ser
545                 550                 555                 560
Tyr Thr Phe Ile Asp Pro Thr Gln Leu Pro Tyr Asn Glu Lys Trp Glu
                565                 570                 575
Phe Pro Arg Asn Asn Leu Gln Phe Gly Lys Thr Leu Gly Ala Gly Ala
                580                 585                 590
Phe Gly Lys Val Val Glu Ala Thr Ala Phe Gly Leu Gly Lys Glu Asp
            595                 600                 605
Ala Val Leu Lys Val Ala Val Lys Met Leu Lys Ser Thr Ala His Ala
            610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
                660                 665                 670
Asn Phe Leu Arg Arg Lys Ala Glu Ala Met Leu Gly Pro Ser Leu Ser
                675                 680                 685
Pro Gly Gln Asp Pro Glu Gly Gly Val Asp Tyr Lys Asn Ile His Leu
            690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
                740                 745                 750
Arg Asp Leu Leu His Phe Ser Ser Gln Val Ala Gln Gly Met Ala Phe
                755                 760                 765
Leu Ala Ser Lys Asn Cys Ile His Arg Asp Val Ala Ala Arg Asn Val
            770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
                820                 825                 830
Thr Val Gln Ser Asp Val Trp Ser Tyr Gly Ile Leu Leu Trp Glu Ile
            835                 840                 845
Phe Ser Leu Gly Leu Asn Pro Tyr Pro Gly Ile Leu Val Asn Ser Lys
850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
                900                 905                 910
Gln Ala Gln Glu Asp Arg Arg Glu Arg Asp Tyr Thr Asn Leu Pro Ser
            915                 920                 925
Ser Ser Arg Ser Gly Gly Ser Gly Ser Ser Ser Ser Glu Leu Glu Glu
            930                 935                 940
```

-continued

```
Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970
```

<210> SEQ ID NO 24
<211> LENGTH: 958
<212> TYPE: PRT
<213> ORGANISM: Artificial Sequence
<220> FEATURE:
<223> OTHER INFORMATION: mCSF1R (full-length, no signal peptide)

<400> SEQUENCE: 24

```
Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
                20                  25                  30

Gly Pro Ile Ser Pro Tyr Trp Thr Leu Asp Pro Glu Ser Pro Gly Ser
            35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
    210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285

Ser Leu Leu Gln Glu Val Ser Val Gly Asp Ser Leu Ile Leu Thr Val
    290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
```

-continued

```
                340                 345                 350
Ser Glu Ala Gly Gln Tyr Phe Leu Met Ala Gln Asn Lys Ala Gly Trp
            355                 360                 365

Asn Asn Leu Thr Phe Glu Leu Thr Leu Arg Tyr Pro Pro Glu Val Ser
        370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
            405                 410                 415

Thr Asp Arg Cys Asp Glu Ala Gln Ala Leu Gln Val Trp Asn Asp Thr
        420                 425                 430

His Pro Glu Val Leu Ser Gln Lys Pro Phe Asp Lys Val Ile Ile Gln
        435                 440                 445

Ser Gln Leu Pro Ile Gly Thr Leu Lys His Asn Met Thr Tyr Phe Cys
        450                 455                 460

Lys Thr His Asn Ser Val Gly Asn Ser Ser Gln Tyr Phe Arg Ala Val
465                 470                 475                 480

Ser Leu Gly Gln Ser Lys Gln Leu Pro Asp Glu Ser Leu Phe Thr Pro
            485                 490                 495

Val Val Val Ala Cys Met Ser Val Met Ser Leu Leu Val Leu Leu Leu
                500                 505                 510

Leu Leu Leu Leu Tyr Lys Tyr Lys Gln Lys Pro Lys Tyr Gln Val Arg
        515                 520                 525

Trp Lys Ile Ile Glu Arg Tyr Glu Gly Asn Ser Tyr Thr Phe Ile Asp
        530                 535                 540

Pro Thr Gln Leu Pro Tyr Asn Glu Lys Trp Glu Phe Pro Arg Asn Asn
545                 550                 555                 560

Leu Gln Phe Gly Lys Thr Leu Gly Ala Gly Ala Phe Gly Lys Val Val
                565                 570                 575

Glu Ala Thr Ala Phe Gly Leu Gly Lys Glu Asp Ala Val Leu Lys Val
            580                 585                 590

Ala Val Lys Met Leu Lys Ser Thr Ala His Ala Asp Glu Lys Glu Ala
        595                 600                 605

Leu Met Ser Glu Leu Lys Ile Met Ser His Leu Gly Gln His Glu Asn
    610                 615                 620

Ile Val Asn Leu Leu Gly Ala Cys Thr His Gly Gly Pro Val Leu Val
625                 630                 635                 640

Ile Thr Glu Tyr Cys Cys Tyr Gly Asp Leu Leu Asn Phe Leu Arg Arg
                645                 650                 655

Lys Ala Glu Ala Met Leu Gly Pro Ser Leu Ser Pro Gly Gln Asp Ser
            660                 665                 670

Glu Gly Asp Ser Ser Tyr Lys Asn Ile His Leu Glu Lys Lys Tyr Val
        675                 680                 685

Arg Arg Asp Ser Gly Phe Ser Ser Gln Gly Val Asp Thr Tyr Val Glu
        690                 695                 700

Met Arg Pro Val Ser Thr Ser Ser Ser Asp Ser Phe Phe Lys Gln Asp
705                 710                 715                 720

Leu Asp Lys Glu Ala Ser Arg Pro Leu Glu Leu Trp Asp Leu Leu His
            725                 730                 735

Phe Ser Ser Gln Val Ala Gln Gly Met Ala Phe Leu Ala Ser Lys Asn
            740                 745                 750

Cys Ile His Arg Asp Val Ala Ala Arg Asn Val Leu Leu Thr Ser Gly
        755                 760                 765
```

```
His Val Ala Lys Ile Gly Asp Phe Gly Leu Ala Arg Asp Ile Met Asn
        770                 775                 780
Asp Ser Asn Tyr Val Val Lys Gly Asn Ala Arg Leu Pro Val Lys Trp
785                 790                 795                 800
Met Ala Pro Glu Ser Ile Phe Asp Cys Val Tyr Thr Val Gln Ser Asp
                805                 810                 815
Val Trp Ser Tyr Gly Ile Leu Leu Trp Glu Ile Phe Ser Leu Gly Leu
                820                 825                 830
Asn Pro Tyr Pro Gly Ile Leu Val Asn Asn Lys Phe Tyr Lys Leu Val
                835                 840                 845
Lys Asp Gly Tyr Gln Met Ala Gln Pro Val Phe Ala Pro Lys Asn Ile
        850                 855                 860
Tyr Ser Ile Met Gln Ser Cys Trp Asp Leu Glu Pro Thr Arg Arg Pro
865                 870                 875                 880
Thr Phe Gln Gln Ile Cys Phe Leu Leu Gln Glu Gln Ala Arg Leu Glu
                885                 890                 895
Arg Arg Asp Gln Asp Tyr Ala Asn Leu Pro Ser Ser Gly Gly Ser Ser
                900                 905                 910
Gly Ser Asp Ser Gly Gly Gly Ser Gly Ser Ser Glu Pro
        915                 920                 925
Glu Glu Glu Ser Ser Ser Glu His Leu Ala Cys Cys Glu Pro Gly Asp
930                 935                 940
Ile Ala Gln Pro Leu Leu Gln Pro Asn Asn Tyr Gln Phe Cys
945                 950                 955

<210> SEQ ID NO 25
<211> LENGTH: 977
<212> TYPE: PRT
<213> ORGANISM: Artificial Sequence
<220> FEATURE:
<223> OTHER INFORMATION: mCSF1R (full-length + signal peptide)

<400> SEQUENCE: 25

Met Glu Leu Gly Pro Pro Leu Val Leu Leu Leu Ala Thr Val Trp His
1               5                   10                  15
Gly Gln Gly Ala Pro Val Ile Glu Pro Ser Gly Pro Glu Leu Val Val
                20                  25                  30
Glu Pro Gly Glu Thr Val Thr Leu Arg Cys Val Ser Asn Gly Ser Val
        35                  40                  45
Glu Trp Asp Gly Pro Ile Ser Pro Tyr Trp Thr Leu Asp Pro Glu Ser
50                  55                  60
Pro Gly Ser Thr Leu Thr Thr Arg Asn Ala Thr Phe Lys Asn Thr Gly
65                  70                  75                  80
Thr Tyr Arg Cys Thr Glu Leu Glu Asp Pro Met Ala Gly Ser Thr Thr
                85                  90                  95
Ile His Leu Tyr Val Lys Asp Pro Ala His Ser Trp Asn Leu Leu Ala
                100                 105                 110
Gln Glu Val Thr Val Val Glu Gly Gln Glu Ala Val Leu Pro Cys Leu
        115                 120                 125
Ile Thr Asp Pro Ala Leu Lys Asp Ser Val Ser Leu Met Arg Glu Gly
130                 135                 140
Gly Arg Gln Val Leu Arg Lys Thr Val Tyr Phe Phe Ser Pro Trp Arg
145                 150                 155                 160
Gly Phe Ile Ile Arg Lys Ala Lys Val Leu Asp Ser Asn Thr Tyr Val
                165                 170                 175
Cys Lys Thr Met Val Asn Gly Arg Glu Ser Thr Ser Thr Gly Ile Trp
```

```
                    180                 185                 190
Leu Lys Val Asn Arg Val His Pro Glu Pro Gln Ile Lys Leu Glu
            195                 200                 205
Pro Ser Lys Leu Val Arg Ile Arg Gly Glu Ala Ala Gln Ile Val Cys
210                 215                 220
Ser Ala Thr Asn Ala Glu Val Gly Phe Asn Val Ile Leu Lys Arg Gly
225                 230                 235                 240
Asp Thr Lys Leu Glu Ile Pro Leu Asn Ser Asp Phe Gln Asp Asn Tyr
            245                 250                 255
Tyr Lys Lys Val Arg Ala Leu Ser Leu Asn Ala Val Asp Phe Gln Asp
            260                 265                 270
Ala Gly Ile Tyr Ser Cys Val Ala Ser Asn Asp Val Gly Thr Arg Thr
            275                 280                 285
Ala Thr Met Asn Phe Gln Val Val Glu Ser Ala Tyr Leu Asn Leu Thr
            290                 295                 300
Ser Glu Gln Ser Leu Leu Gln Glu Val Ser Val Gly Asp Ser Leu Ile
305                 310                 315                 320
Leu Thr Val His Ala Asp Ala Tyr Pro Ser Ile Gln His Tyr Asn Trp
            325                 330                 335
Thr Tyr Leu Gly Pro Phe Phe Glu Asp Gln Arg Lys Leu Glu Phe Ile
            340                 345                 350
Thr Gln Arg Ala Ile Tyr Arg Tyr Thr Phe Lys Leu Phe Leu Asn Arg
            355                 360                 365
Val Lys Ala Ser Glu Ala Gly Gln Tyr Phe Leu Met Ala Gln Asn Lys
            370                 375                 380
Ala Gly Trp Asn Asn Leu Thr Phe Glu Leu Thr Leu Arg Tyr Pro Pro
385                 390                 395                 400
Glu Val Ser Val Thr Trp Met Pro Val Asn Gly Ser Asp Val Leu Phe
            405                 410                 415
Cys Asp Val Ser Gly Tyr Pro Gln Pro Ser Val Thr Trp Met Glu Cys
            420                 425                 430
Arg Gly His Thr Asp Arg Cys Asp Glu Ala Gln Ala Leu Gln Val Trp
            435                 440                 445
Asn Asp Thr His Pro Glu Val Leu Ser Gln Lys Pro Phe Asp Lys Val
450                 455                 460
Ile Ile Gln Ser Gln Leu Pro Ile Gly Thr Leu Lys His Asn Met Thr
465                 470                 475                 480
Tyr Phe Cys Lys Thr His Asn Ser Val Gly Asn Ser Ser Gln Tyr Phe
            485                 490                 495
Arg Ala Val Ser Leu Gly Gln Ser Lys Gln Leu Pro Asp Glu Ser Leu
            500                 505                 510
Phe Thr Pro Val Val Val Ala Cys Met Ser Val Met Ser Leu Leu Val
            515                 520                 525
Leu Leu Leu Leu Leu Leu Leu Tyr Lys Tyr Lys Gln Lys Pro Lys Tyr
            530                 535                 540
Gln Val Arg Trp Lys Ile Ile Glu Arg Tyr Glu Gly Asn Ser Tyr Thr
545                 550                 555                 560
Phe Ile Asp Pro Thr Gln Leu Pro Tyr Asn Glu Lys Trp Glu Phe Pro
            565                 570                 575
Arg Asn Asn Leu Gln Phe Gly Lys Thr Leu Gly Ala Gly Ala Phe Gly
            580                 585                 590
Lys Val Val Glu Ala Thr Ala Phe Gly Leu Gly Lys Glu Asp Ala Val
            595                 600                 605
```

-continued

Leu Lys Val Ala Val Lys Met Leu Lys Ser Thr Ala His Ala Asp Glu
610                 615                 620

Lys Glu Ala Leu Met Ser Glu Leu Lys Ile Met Ser His Leu Gly Gln
625                 630                 635                 640

His Glu Asn Ile Val Asn Leu Leu Gly Ala Cys Thr His Gly Gly Pro
            645                 650                 655

Val Leu Val Ile Thr Glu Tyr Cys Cys Tyr Gly Asp Leu Leu Asn Phe
        660                 665                 670

Leu Arg Arg Lys Ala Glu Ala Met Leu Gly Pro Ser Leu Ser Pro Gly
    675                 680                 685

Gln Asp Ser Glu Gly Asp Ser Ser Tyr Lys Asn Ile His Leu Glu Lys
690                 695                 700

Lys Tyr Val Arg Arg Asp Ser Gly Phe Ser Ser Gln Gly Val Asp Thr
705                 710                 715                 720

Tyr Val Glu Met Arg Pro Val Ser Thr Ser Ser Ser Asp Ser Phe Phe
                725                 730                 735

Lys Gln Asp Leu Asp Lys Glu Ala Ser Arg Pro Leu Glu Leu Trp Asp
            740                 745                 750

Leu Leu His Phe Ser Ser Gln Val Ala Gln Gly Met Ala Phe Leu Ala
        755                 760                 765

Ser Lys Asn Cys Ile His Arg Asp Val Ala Ala Arg Asn Val Leu Leu
770                 775                 780

Thr Ser Gly His Val Ala Lys Ile Gly Asp Phe Gly Leu Ala Arg Asp
785                 790                 795                 800

Ile Met Asn Asp Ser Asn Tyr Val Val Lys Gly Asn Ala Arg Leu Pro
                805                 810                 815

Val Lys Trp Met Ala Pro Glu Ser Ile Phe Asp Cys Val Tyr Thr Val
            820                 825                 830

Gln Ser Asp Val Trp Ser Tyr Gly Ile Leu Leu Trp Glu Ile Phe Ser
        835                 840                 845

Leu Gly Leu Asn Pro Tyr Pro Gly Ile Leu Val Asn Asn Lys Phe Tyr
850                 855                 860

Lys Leu Val Lys Asp Gly Tyr Gln Met Ala Gln Pro Val Phe Ala Pro
865                 870                 875                 880

Lys Asn Ile Tyr Ser Ile Met Gln Ser Cys Trp Asp Leu Glu Pro Thr
                885                 890                 895

Arg Arg Pro Thr Phe Gln Gln Ile Cys Phe Leu Leu Gln Glu Gln Ala
            900                 905                 910

Arg Leu Glu Arg Arg Asp Gln Asp Tyr Ala Asn Leu Pro Ser Ser Gly
        915                 920                 925

Gly Ser Ser Gly Ser Asp Ser Gly Gly Ser Ser Gly Gly Ser Ser Ser
930                 935                 940

Ser Glu Pro Glu Glu Glu Ser Ser Ser Glu His Leu Ala Cys Cys Glu
945                 950                 955                 960

Pro Gly Asp Ile Ala Gln Pro Leu Leu Gln Pro Asn Asn Tyr Gln Phe
                965                 970                 975

Cys

<210> SEQ ID NO 26
<211> LENGTH: 492
<212> TYPE: PRT
<213> ORGANISM: Artificial Sequence
<220> FEATURE:
<223> OTHER INFORMATION: hCSF1R-ECD.511

<400> SEQUENCE: 26

```
Ile Pro Val Ile Glu Pro Ser Val Pro Glu Leu Val Val Lys Pro Gly
 1               5                  10                  15

Ala Thr Val Thr Leu Arg Cys Val Gly Asn Gly Ser Val Glu Trp Asp
                 20                  25                  30

Gly Pro Pro Ser Pro His Trp Thr Leu Tyr Ser Asp Gly Ser Ser Ser
             35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65              70                  75                      80

Tyr Val Lys Asp Pro Ala Arg Pro Trp Asn Val Leu Ala Gln Glu Val
             85                  90                  95

Val Val Phe Glu Asp Gln Asp Ala Leu Leu Pro Cys Leu Leu Thr Asp
             100                 105                 110

Pro Val Leu Glu Ala Gly Val Ser Leu Val Arg Val Arg Gly Arg Pro
             115                 120                 125

Leu Met Arg His Thr Asn Tyr Ser Phe Ser Pro Trp His Gly Phe Thr
         130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                 165                 170                 175

Gln Lys Val Ile Pro Gly Pro Pro Ala Leu Thr Leu Val Pro Ala Glu
             180                 185                 190

Leu Val Arg Ile Arg Gly Glu Ala Ala Gln Ile Val Cys Ser Ala Ser
         195                 200                 205

Ser Val Asp Val Asn Phe Asp Val Phe Leu Gln His Asn Asn Thr Lys
         210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                 245                 250                 255

Tyr Ser Cys Val Ala Ser Asn Val Gln Gly Lys His Ser Thr Ser Met
                 260                 265                 270

Phe Phe Arg Val Val Glu Ser Ala Tyr Leu Asn Leu Ser Ser Glu Gln
             275                 280                 285

Asn Leu Ile Gln Glu Val Thr Val Gly Glu Gly Leu Asn Leu Lys Val
         290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                 325                 330                 335

Thr Lys Asp Thr Tyr Arg His Thr Phe Thr Leu Ser Leu Pro Arg Leu
             340                 345                 350

Lys Pro Ser Glu Ala Gly Arg Tyr Ser Phe Leu Ala Arg Asn Pro Gly
         355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                 405                 410                 415

Gly His Thr Asp Arg Cys Asp Glu Ala Gln Val Leu Gln Val Trp Asp
```

-continued

```
                420             425             430
Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp
                485                 490

<210> SEQ ID NO 27
<211> LENGTH: 511
<212> TYPE: PRT
<213> ORGANISM: Artificial Sequence
<220> FEATURE:
<223> OTHER INFORMATION: hCSF1R-ECD.511 with signal peptide

<400> SEQUENCE: 27

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300
```

```
Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp
            500                 505                 510

<210> SEQ ID NO 28
<211> LENGTH: 724
<212> TYPE: PRT
<213> ORGANISM: Artificial Sequence
<220> FEATURE:
<223> OTHER INFORMATION: hCSF1R-ECD.511-Fc

<400> SEQUENCE: 28

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
        130                 135                 140

Ile His Arg Ala Lys Phe Ile Gln Ser Gln Asp Tyr Gln Cys Ser Ala
145                 150                 155                 160
```

```
Leu Met Gly Gly Arg Lys Val Met Ser Ile Ser Ile Arg Leu Lys Val
                165                 170                 175
Gln Lys Val Ile Pro Gly Pro Pro Ala Leu Thr Leu Val Pro Ala Glu
            180                 185                 190
Leu Val Arg Ile Arg Gly Glu Ala Ala Gln Ile Val Cys Ser Ala Ser
        195                 200                 205
Ser Val Asp Val Asn Phe Asp Val Phe Leu Gln His Asn Asn Thr Lys
    210                 215                 220
Leu Ala Ile Pro Gln Gln Ser Asp Phe His Asn Asn Arg Tyr Gln Lys
225                 230                 235                 240
Val Leu Thr Leu Asn Leu Asp Gln Val Asp Phe Gln His Ala Gly Asn
                245                 250                 255
Tyr Ser Cys Val Ala Ser Asn Val Gln Gly Lys His Ser Thr Ser Met
            260                 265                 270
Phe Phe Arg Val Val Glu Ser Ala Tyr Leu Asn Leu Ser Ser Glu Gln
        275                 280                 285
Asn Leu Ile Gln Glu Val Thr Val Gly Glu Gly Leu Asn Leu Lys Val
    290                 295                 300
Met Val Glu Ala Tyr Pro Gly Leu Gln Gly Phe Asn Trp Thr Tyr Leu
305                 310                 315                 320
Gly Pro Phe Ser Asp His Gln Pro Glu Pro Lys Leu Ala Asn Ala Thr
                325                 330                 335
Thr Lys Asp Thr Tyr Arg His Thr Phe Thr Leu Ser Leu Pro Arg Leu
            340                 345                 350
Lys Pro Ser Glu Ala Gly Arg Tyr Ser Phe Leu Ala Arg Asn Pro Gly
        355                 360                 365
Gly Trp Arg Ala Leu Thr Phe Glu Leu Thr Leu Arg Tyr Pro Pro Glu
    370                 375                 380
Val Ser Val Ile Trp Thr Phe Ile Asn Gly Ser Gly Thr Leu Leu Cys
385                 390                 395                 400
Ala Ala Ser Gly Tyr Pro Gln Pro Asn Val Thr Trp Leu Gln Cys Ser
                405                 410                 415
Gly His Thr Asp Arg Cys Asp Glu Ala Gln Val Leu Gln Val Trp Asp
            420                 425                 430
Asp Pro Tyr Pro Glu Val Leu Ser Gln Glu Pro Phe His Lys Val Thr
        435                 440                 445
Val Gln Ser Leu Leu Thr Val Glu Thr Leu Glu His Asn Gln Thr Tyr
    450                 455                 460
Glu Cys Arg Ala His Asn Ser Val Gly Ser Gly Ser Trp Ala Phe Ile
465                 470                 475                 480
Pro Ile Ser Ala Gly Ala His Thr His Pro Pro Asp Glu Pro Lys Ser
                485                 490                 495
Ser Asp Lys Thr His Thr Cys Pro Pro Cys Pro Ala Pro Glu Leu Leu
            500                 505                 510
Gly Gly Pro Ser Val Phe Leu Phe Pro Pro Lys Pro Lys Asp Thr Leu
        515                 520                 525
Met Ile Ser Arg Thr Pro Glu Val Thr Cys Val Val Val Asp Val Ser
    530                 535                 540
His Glu Asp Pro Glu Val Lys Phe Asn Trp Tyr Val Asp Gly Val Glu
545                 550                 555                 560
Val His Asn Ala Lys Thr Lys Pro Arg Glu Glu Gln Tyr Asn Ser Thr
                565                 570                 575
Tyr Arg Val Val Ser Val Leu Thr Val Leu His Gln Asp Trp Leu Asn
            580                 585                 590
```

-continued

```
Gly Lys Glu Tyr Lys Cys Lys Val Ser Asn Lys Ala Leu Pro Ala Pro
            595                 600                 605

Ile Glu Lys Thr Ile Ser Lys Ala Lys Gly Gln Pro Arg Glu Pro Gln
    610                 615                 620

Val Tyr Thr Leu Pro Pro Ser Arg Asp Glu Leu Thr Lys Asn Gln Val
625                 630                 635                 640

Ser Leu Thr Cys Leu Val Lys Gly Phe Tyr Pro Ser Asp Ile Ala Val
            645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
            675                 680                 685

Val Asp Lys Ser Arg Trp Gln Gln Gly Asn Val Phe Ser Cys Ser Val
            690                 695                 700

Met His Glu Ala Leu His Asn His Tyr Thr Gln Lys Ser Leu Ser Leu
705                 710                 715                 720

Ser Pro Gly Lys

<210> SEQ ID NO 29
<211> LENGTH: 743
<212> TYPE: PRT
<213> ORGANISM: Artificial Sequence
<220> FEATURE:
<223> OTHER INFORMATION: hCSF1R-ECD.511-Fc with signal peptide

<400> SEQUENCE: 29

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
```

-continued

```
            225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
                260                 265                 270
Ala Gly Asn Tyr Ser Cys Val Ala Ser Asn Val Gln Gly Lys His Ser
                275                 280                 285
Thr Ser Met Phe Phe Arg Val Val Glu Ser Ala Tyr Leu Asn Leu Ser
            290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
                340                 345                 350
Asn Ala Thr Thr Lys Asp Thr Tyr Arg His Thr Phe Thr Leu Ser Leu
                355                 360                 365
Pro Arg Leu Lys Pro Ser Glu Ala Gly Arg Tyr Ser Phe Leu Ala Arg
            370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
            420                 425                 430
Gln Cys Ser Gly His Thr Asp Arg Cys Asp Glu Ala Gln Val Leu Gln
            435                 440                 445
Val Trp Asp Asp Pro Tyr Pro Glu Val Leu Ser Gln Glu Pro Phe His
            450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
                500                 505                 510
Pro Lys Ser Ser Asp Lys Thr His Thr Cys Pro Pro Cys Pro Ala Pro
                515                 520                 525
Glu Leu Leu Gly Gly Pro Ser Val Phe Leu Phe Pro Pro Lys Pro Lys
            530                 535                 540
Asp Thr Leu Met Ile Ser Arg Thr Pro Glu Val Thr Cys Val Val Val
545                 550                 555                 560
Asp Val Ser His Glu Asp Pro Glu Val Lys Phe Asn Trp Tyr Val Asp
                565                 570                 575
Gly Val Glu Val His Asn Ala Lys Thr Lys Pro Arg Glu Glu Gln Tyr
                580                 585                 590
Asn Ser Thr Tyr Arg Val Val Ser Val Leu Thr Val Leu His Gln Asp
            595                 600                 605
Trp Leu Asn Gly Lys Glu Tyr Lys Cys Lys Val Ser Asn Lys Ala Leu
            610                 615                 620
Pro Ala Pro Ile Glu Lys Thr Ile Ser Lys Ala Lys Gly Gln Pro Arg
625                 630                 635                 640
Glu Pro Gln Val Tyr Thr Leu Pro Pro Ser Arg Asp Glu Leu Thr Lys
                645                 650                 655
```

```
Asn Gln Val Ser Leu Thr Cys Leu Val Lys Gly Phe Tyr Pro Ser Asp
            660                 665                 670
Ile Ala Val Glu Trp Glu Ser Asn Gly Gln Pro Glu Asn Asn Tyr Lys
            675                 680                 685
Thr Thr Pro Pro Val Leu Asp Ser Asp Gly Ser Phe Phe Leu Tyr Ser
            690                 695                 700
Lys Leu Thr Val Asp Lys Ser Arg Trp Gln Gln Gly Asn Val Phe Ser
705                 710                 715                 720
Cys Ser Val Met His Glu Ala Leu His Asn His Tyr Thr Gln Lys Ser
                725                 730                 735
Leu Ser Leu Ser Pro Gly Lys
            740

<210> SEQ ID NO 30
<211> LENGTH: 233
<212> TYPE: PRT
<213> ORGANISM: Artificial Sequence
<220> FEATURE:
<223> OTHER INFORMATION: Fc C237S with N-terminal GS linker

<400> SEQUENCE: 30

Gly Ser Glu Pro Lys Ser Ser Asp Lys Thr His Thr Cys Pro Pro Cys
1               5                   10                  15
Pro Ala Pro Glu Leu Leu Gly Gly Pro Ser Val Phe Leu Phe Pro Pro
            20                  25                  30
Lys Pro Lys Asp Thr Leu Met Ile Ser Arg Thr Pro Glu Val Thr Cys
        35                  40                  45
Val Val Val Asp Val Ser His Glu Asp Pro Glu Val Lys Phe Asn Trp
    50                  55                  60
Tyr Val Asp Gly Val Glu Val His Asn Ala Lys Thr Lys Pro Arg Glu
65                  70                  75                  80
Glu Gln Tyr Asn Ser Thr Tyr Arg Val Val Ser Val Leu Thr Val Leu
                85                  90                  95
His Gln Asp Trp Leu Asn Gly Lys Glu Tyr Lys Cys Lys Val Ser Asn
            100                 105                 110
Lys Ala Leu Pro Ala Pro Ile Glu Lys Thr Ile Ser Lys Ala Lys Gly
        115                 120                 125
Gln Pro Arg Glu Pro Gln Val Tyr Thr Leu Pro Pro Ser Arg Asp Glu
    130                 135                 140
Leu Thr Lys Asn Gln Val Leu Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Ser Lys Leu Thr Val Asp Lys Ser Arg Trp Gln Gln Gly Asn Val
        195                 200                 205
Phe Ser Cys Ser Val Met His Glu Ala Leu His Asn His Tyr Thr Gln
    210                 215                 220
Lys Ser Leu Ser Leu Ser Pro Gly Lys
225                 230

<210> SEQ ID NO 31
<211> LENGTH: 727
<212> TYPE: PRT
<213> ORGANISM: Artificial Sequence
<220> FEATURE:
<223> OTHER INFORMATION: hCSF1R-ECD.512-Fc with GS linker
```

<400> SEQUENCE: 31

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
        210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
            290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415
```

```
Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Gly Phe Glu
            485                 490                 495

Pro Lys Ser Ser Asp Lys Thr His Thr Cys Pro Pro Cys Pro Ala Pro
            500                 505                 510

Glu Leu Leu Gly Gly Pro Ser Val Phe Leu Phe Pro Pro Lys Pro Lys
            515                 520                 525

Asp Thr Leu Met Ile Ser Arg Thr Pro Glu Val Thr Cys Val Val Val
            530                 535                 540

Asp Val Ser His Glu Asp Pro Glu Val Lys Phe Asn Trp Tyr Val Asp
545                 550                 555                 560

Gly Val Glu Val His Asn Ala Lys Thr Lys Pro Arg Glu Glu Gln Tyr
            565                 570                 575

Asn Ser Thr Tyr Arg Val Val Ser Val Leu Thr Val Leu His Gln Asp
            580                 585                 590

Trp Leu Asn Gly Lys Glu Tyr Lys Cys Lys Val Ser Asn Lys Ala Leu
            595                 600                 605

Pro Ala Pro Ile Glu Lys Thr Ile Ser Lys Ala Lys Gly Gln Pro Arg
            610                 615                 620

Glu Pro Gln Val Tyr Thr Leu Pro Pro Ser Arg Asp Glu Leu Thr Lys
625                 630                 635                 640

Asn Gln Val Ser Leu Thr Cys Leu Val Lys Gly Phe Tyr Pro Ser Asp
            645                 650                 655

Ile Ala Val Glu Trp Glu Ser Asn Gly Gln Pro Glu Asn Asn Tyr Lys
            660                 665                 670

Thr Thr Pro Pro Val Leu Asp Ser Asp Gly Ser Phe Phe Leu Tyr Ser
            675                 680                 685

Lys Leu Thr Val Asp Lys Ser Arg Trp Gln Gln Gly Asn Val Phe Ser
            690                 695                 700

Cys Ser Val Met His Glu Ala Leu His Asn His Tyr Thr Gln Lys Ser
705                 710                 715                 720

Leu Ser Leu Ser Pro Gly Lys
            725

<210> SEQ ID NO 32
<211> LENGTH: 721
<212> TYPE: PRT
<213> ORGANISM: Artificial Sequence
<220> FEATURE:
<223> OTHER INFORMATION: hCSF1R-ECD.506-Fc with GS linker

<400> SEQUENCE: 32

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
            35                  40                  45
```

```
Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
    450                 455                 460

Glu Cys Arg Ala His Asn Ser Val Gly Ser Gly Ser Trp Ala Phe Ile
465                 470                 475                 480
```

```
Pro Ile Ser Ala Gly Ala His Gly Phe Glu Pro Lys Ser Ser Asp Lys
                485                 490                 495

Thr His Thr Cys Pro Pro Cys Pro Ala Pro Glu Leu Leu Gly Gly Pro
            500                 505                 510

Ser Val Phe Leu Phe Pro Pro Lys Pro Lys Asp Thr Leu Met Ile Ser
        515                 520                 525

Arg Thr Pro Glu Val Thr Cys Val Val Val Asp Val Ser His Glu Asp
    530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
                565                 570                 575

Val Ser Val Leu Thr Val Leu His Gln Asp Trp Leu Asn Gly Lys Glu
            580                 585                 590

Tyr Lys Cys Lys Val Ser Asn Lys Ala Leu Pro Ala Pro Ile Glu Lys
        595                 600                 605

Thr Ile Ser Lys Ala Lys Gly Gln Pro Arg Glu Pro Gln Val Tyr Thr
    610                 615                 620

Leu Pro Pro Ser Arg Asp Glu Leu Thr Lys Asn Gln Val Ser Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
            660                 665                 670

Asp Ser Asp Gly Ser Phe Phe Leu Tyr Ser Lys Leu Thr Val Asp Lys
        675                 680                 685

Ser Arg Trp Gln Gln Gly Asn Val Phe Ser Cys Ser Val Met His Glu
    690                 695                 700

Ala Leu His Asn His Tyr Thr Gln Lys Ser Leu Ser Leu Ser Pro Gly
705                 710                 715                 720

Lys

<210> SEQ ID NO 33
<211> LENGTH: 726
<212> TYPE: PRT
<213> ORGANISM: Artificial Sequence
<220> FEATURE:
<223> OTHER INFORMATION: mCSF1R-ECD.511-Fc with GS linker

<400> SEQUENCE: 33

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
                20                  25                  30

Gly Pro Ile Ser Pro Tyr Trp Thr Leu Asp Pro Glu Ser Pro Gly Ser
            35                  40                  45

Thr Leu Thr Thr Arg Asn Ala Thr Phe Lys Asn Thr Gly Thr Tyr Arg
        50                  55                  60

Cys Thr Glu Leu Glu Asp Pro Met Ala Gly Ser Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
```

-continued

```
            115                 120                 125
Val Leu Arg Lys Thr Val Tyr Phe Phe Ser Pro Trp Arg Gly Phe Ile
130                 135                 140
Ile Arg Lys Ala Lys Val Leu Asp Ser Asn Thr Tyr Val Cys Lys Thr
145                 150                 155                 160
Met Val Asn Gly Arg Glu Ser Thr Ser Thr Gly Ile Trp Leu Lys Val
                165                 170                 175
Asn Arg Val His Pro Glu Pro Pro Gln Ile Lys Leu Glu Pro Ser Lys
                180                 185                 190
Leu Val Arg Ile Arg Gly Glu Ala Ala Gln Ile Val Cys Ser Ala Thr
                195                 200                 205
Asn Ala Glu Val Gly Phe Asn Val Ile Leu Lys Arg Gly Asp Thr Lys
210                 215                 220
Leu Glu Ile Pro Leu Asn Ser Asp Phe Gln Asp Asn Tyr Tyr Lys Lys
225                 230                 235                 240
Val Arg Ala Leu Ser Leu Asn Ala Val Asp Phe Gln Asp Ala Gly Ile
                245                 250                 255
Tyr Ser Cys Val Ala Ser Asn Asp Val Gly Thr Arg Thr Ala Thr Met
                260                 265                 270
Asn Phe Gln Val Val Glu Ser Ala Tyr Leu Asn Leu Thr Ser Glu Gln
                275                 280                 285
Ser Leu Leu Gln Glu Val Ser Val Gly Asp Ser Leu Ile Leu Thr Val
                290                 295                 300
His Ala Asp Ala Tyr Pro Ser Ile Gln His Tyr Asn Trp Thr Tyr Leu
305                 310                 315                 320
Gly Pro Phe Phe Glu Asp Gln Arg Lys Leu Glu Phe Ile Thr Gln Arg
                325                 330                 335
Ala Ile Tyr Arg Tyr Thr Phe Lys Leu Phe Leu Asn Arg Val Lys Ala
                340                 345                 350
Ser Glu Ala Gly Gln Tyr Phe Leu Met Ala Gln Asn Lys Ala Gly Trp
                355                 360                 365
Asn Asn Leu Thr Phe Glu Leu Thr Leu Arg Tyr Pro Pro Glu Val Ser
370                 375                 380
Val Thr Trp Met Pro Val Asn Gly Ser Asp Val Leu Phe Cys Asp Val
385                 390                 395                 400
Ser Gly Tyr Pro Gln Pro Ser Val Thr Trp Met Glu Cys Arg Gly His
                405                 410                 415
Thr Asp Arg Cys Asp Glu Ala Gln Ala Leu Gln Val Trp Asn Asp Thr
                420                 425                 430
His Pro Glu Val Leu Ser Gln Lys Pro Phe Asp Lys Val Ile Ile Gln
                435                 440                 445
Ser Gln Leu Pro Ile Gly Thr Leu Lys His Asn Met Thr Tyr Phe Cys
                450                 455                 460
Lys Thr His Asn Ser Val Gly Asn Ser Ser Gln Tyr Phe Arg Ala Val
465                 470                 475                 480
Ser Leu Gly Gln Ser Lys Gln Leu Pro Asp Glu Ser Gly Phe Glu Pro
                485                 490                 495
Lys Ser Ser Asp Lys Thr His Thr Cys Pro Pro Cys Pro Ala Pro Glu
                500                 505                 510
Leu Leu Gly Gly Pro Ser Val Phe Leu Phe Pro Pro Lys Pro Lys Asp
                515                 520                 525
Thr Leu Met Ile Ser Arg Thr Pro Glu Val Thr Cys Val Val Val Asp
530                 535                 540
```

Val Ser His Glu Asp Pro Glu Val Lys Phe Asn Trp Tyr Val Asp Gly
545                 550                 555                 560

Val Glu Val His Asn Ala Lys Thr Lys Pro Arg Glu Glu Gln Tyr Asn
                565                 570                 575

Ser Thr Tyr Arg Val Val Ser Val Leu Thr Val Leu His Gln Asp Trp
            580                 585                 590

Leu Asn Gly Lys Glu Tyr Lys Cys Lys Val Ser Asn Lys Ala Leu Pro
        595                 600                 605

Ala Pro Ile Glu Lys Thr Ile Ser Lys Ala Lys Gly Gln Pro Arg Glu
610                 615                 620

Pro Gln Val Tyr Thr Leu Pro Pro Ser Arg Asp Glu Leu Thr Lys Asn
625                 630                 635                 640

Gln Val Ser Leu Thr Cys Leu Val Lys Gly Phe Tyr Pro Ser Asp Ile
                645                 650                 655

Ala Val Glu Trp Glu Ser Asn Gly Gln Pro Glu Asn Asn Tyr Lys Thr
            660                 665                 670

Thr Pro Pro Val Leu Asp Ser Asp Gly Ser Phe Phe Leu Tyr Ser Lys
        675                 680                 685

Leu Thr Val Asp Lys Ser Arg Trp Gln Gln Gly Asn Val Phe Ser Cys
690                 695                 700

Ser Val Met His Glu Ala Leu His Asn His Tyr Thr Gln Lys Ser Leu
705                 710                 715                 720

Ser Leu Ser Pro Gly Lys
                725

<210> SEQ ID NO 34
<211> LENGTH: 721
<212> TYPE: PRT
<213> ORGANISM: Artificial Sequence
<220> FEATURE:
<223> OTHER INFORMATION: mCSF1R-ECD.506-Fc with GS linker

<400> SEQUENCE: 34

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
                20                  25                  30

Gly Pro Ile Ser Pro Tyr Trp Thr Leu Asp Pro Glu Ser Pro Gly Ser
            35                  40                  45

Thr Leu Thr Thr Arg Asn Ala Thr Phe Lys Asn Thr Gly Thr Tyr Arg
        50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
                100                 105                 110

Pro Ala Leu Lys Asp Ser Val Ser Leu Met Arg Glu Gly Gly Arg Gln
            115                 120                 125

Val Leu Arg Lys Thr Val Tyr Phe Phe Ser Pro Trp Arg Gly Phe Ile
130                 135                 140

Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys

```
                    180                 185                 190
Leu Val Arg Ile Arg Gly Glu Ala Ala Gln Ile Val Cys Ser Ala Thr
                195                 200                 205

Asn Ala Glu Val Gly Phe Asn Val Ile Leu Lys Arg Gly Asp Thr Lys
            210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
            260                 265                 270

Asn Phe Gln Val Val Glu Ser Ala Tyr Leu Asn Leu Thr Ser Glu Gln
        275                 280                 285

Ser Leu Leu Gln Glu Val Ser Val Gly Asp Ser Leu Ile Leu Thr Val
    290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
            340                 345                 350

Ser Glu Ala Gly Gln Tyr Phe Leu Met Ala Gln Asn Lys Ala Gly Trp
        355                 360                 365

Asn Asn Leu Thr Phe Glu Leu Thr Leu Arg Tyr Pro Pro Glu Val Ser
    370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
            420                 425                 430

His Pro Glu Val Leu Ser Gln Lys Pro Phe Asp Lys Val Ile Ile Gln
        435                 440                 445

Ser Gln Leu Pro Ile Gly Thr Leu Lys His Asn Met Thr Tyr Phe Cys
    450                 455                 460

Lys Thr His Asn Ser Val Gly Asn Ser Ser Gln Tyr Phe Arg Ala Val
465                 470                 475                 480

Ser Leu Gly Gln Ser Lys Gln Gly Phe Glu Pro Lys Ser Ser Asp Lys
                485                 490                 495

Thr His Thr Cys Pro Pro Cys Pro Ala Pro Glu Leu Leu Gly Gly Pro
            500                 505                 510

Ser Val Phe Leu Phe Pro Pro Lys Pro Lys Asp Thr Leu Met Ile Ser
        515                 520                 525

Arg Thr Pro Glu Val Thr Cys Val Val Val Asp Val Ser His Glu Asp
    530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
                565                 570                 575

Val Ser Val Leu Thr Val Leu His Gln Asp Trp Leu Asn Gly Lys Glu
            580                 585                 590

Tyr Lys Cys Lys Val Ser Asn Lys Ala Leu Pro Ala Pro Ile Glu Lys
        595                 600                 605
```

```
Thr Ile Ser Lys Ala Lys Gly Gln Pro Arg Glu Pro Gln Val Tyr Thr
610                 615                 620

Leu Pro Pro Ser Arg Asp Glu Leu Thr Lys Asn Gln Val Ser Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
                660                 665                 670

Asp Ser Asp Gly Ser Phe Phe Leu Tyr Ser Lys Leu Thr Val Asp Lys
            675                 680                 685

Ser Arg Trp Gln Gln Gly Asn Val Phe Ser Cys Ser Val Met His Glu
690                 695                 700

Ala Leu His Asn His Tyr Thr Gln Lys Ser Leu Ser Leu Ser Pro Gly
705                 710                 715                 720

Lys

<210> SEQ ID NO 35
<211> LENGTH: 746
<212> TYPE: PRT
<213> ORGANISM: Artificial Sequence
<220> FEATURE:
<223> OTHER INFORMATION: hCSF1R-ECD.512-Fc with signal peptide and GS
      linker

<400> SEQUENCE: 35

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
```

-continued

```
                245                 250                 255
Tyr Gln Lys Val Leu Thr Leu Asn Leu Asp Gln Val Asp Phe Gln His
            260                 265                 270
Ala Gly Asn Tyr Ser Cys Val Ala Ser Asn Val Gln Gly Lys His Ser
            275                 280                 285
Thr Ser Met Phe Phe Arg Val Glu Ser Ala Tyr Leu Asn Leu Ser
            290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
            340                 345                 350
Asn Ala Thr Thr Lys Asp Thr Tyr Arg His Thr Phe Thr Leu Ser Leu
            355                 360                 365
Pro Arg Leu Lys Pro Ser Glu Ala Gly Arg Tyr Ser Phe Leu Ala Arg
            370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
            420                 425                 430
Gln Cys Ser Gly His Thr Asp Arg Cys Asp Glu Ala Gln Val Leu Gln
            435                 440                 445
Val Trp Asp Asp Pro Tyr Pro Glu Val Leu Ser Gln Glu Pro Phe His
            450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
            500                 505                 510
Gly Phe Glu Pro Lys Ser Ser Asp Lys Thr His Thr Cys Pro Pro Cys
            515                 520                 525
Pro Ala Pro Glu Leu Leu Gly Gly Pro Ser Val Phe Leu Phe Pro Pro
            530                 535                 540
Lys Pro Lys Asp Thr Leu Met Ile Ser Arg Thr Pro Glu Val Thr Cys
545                 550                 555                 560
Val Val Val Asp Val Ser His Glu Asp Pro Glu Val Lys Phe Asn Trp
                565                 570                 575
Tyr Val Asp Gly Val Glu Val His Asn Ala Lys Thr Lys Pro Arg Glu
            580                 585                 590
Glu Gln Tyr Asn Ser Thr Tyr Arg Val Val Ser Val Leu Thr Val Leu
            595                 600                 605
His Gln Asp Trp Leu Asn Gly Lys Glu Tyr Lys Cys Lys Val Ser Asn
            610                 615                 620
Lys Ala Leu Pro Ala Pro Ile Glu Lys Thr Ile Ser Lys Ala Lys Gly
625                 630                 635                 640
Gln Pro Arg Glu Pro Gln Val Tyr Thr Leu Pro Pro Ser Arg Asp Glu
                645                 650                 655
Leu Thr Lys Asn Gln Val Ser Leu Thr Cys Leu Val Lys Gly Phe Tyr
            660                 665                 670
```

-continued

```
Pro Ser Asp Ile Ala Val Glu Trp Glu Ser Asn Gly Gln Pro Glu Asn
    675                 680                 685
Asn Tyr Lys Thr Thr Pro Val Leu Asp Ser Asp Gly Ser Phe Phe
    690                 695                 700
Leu Tyr Ser Lys Leu Thr Val Asp Lys Ser Arg Trp Gln Gln Gly Asn
705                 710                 715                 720
Val Phe Ser Cys Ser Val Met His Glu Ala Leu His Asn His Tyr Thr
                725                 730                 735
Gln Lys Ser Leu Ser Leu Ser Pro Gly Lys
            740                 745

<210> SEQ ID NO 36
<211> LENGTH: 740
<212> TYPE: PRT
<213> ORGANISM: Artificial Sequence
<220> FEATURE:
<223> OTHER INFORMATION: hCSF1R-ECD.506-Fc with signal peptide and GS
      linker

<400> SEQUENCE: 36

Met Gly Pro Gly Val Leu Leu Leu Leu Val Ala Thr Ala Trp His
1               5                   10                  15
Gly Gln Gly Ile Pro Val Ile Glu Pro Ser Val Pro Glu Leu Val Val
                20                  25                  30
Lys Pro Gly Ala Thr Val Thr Leu Arg Cys Val Gly Asn Gly Ser Val
            35                  40                  45
Glu Trp Asp Gly Pro Pro Ser Pro His Trp Thr Leu Tyr Ser Asp Gly
        50                  55                  60
Ser Ser Ser Ile Leu Ser Thr Asn Asn Ala Thr Phe Gln Asn Thr Gly
65                  70                  75                  80
Thr Tyr Arg Cys Thr Glu Pro Gly Asp Pro Leu Gly Gly Ser Ala Ala
                85                  90                  95
Ile His Leu Tyr Val Lys Asp Pro Ala Arg Pro Trp Asn Val Leu Ala
                100                 105                 110
Gln Glu Val Val Val Phe Glu Asp Gln Asp Ala Leu Leu Pro Cys Leu
            115                 120                 125
Leu Thr Asp Pro Val Leu Glu Ala Gly Val Ser Leu Val Arg Val Arg
        130                 135                 140
Gly Arg Pro Leu Met Arg His Thr Asn Tyr Ser Phe Ser Pro Trp His
145                 150                 155                 160
Gly Phe Thr Ile His Arg Ala Lys Phe Ile Gln Ser Gln Asp Tyr Gln
                165                 170                 175
Cys Ser Ala Leu Met Gly Gly Arg Lys Val Met Ser Ile Ser Ile Arg
            180                 185                 190
Leu Lys Val Gln Lys Val Ile Pro Gly Pro Pro Ala Leu Thr Leu Val
        195                 200                 205
Pro Ala Glu Leu Val Arg Ile Arg Gly Glu Ala Ala Gln Ile Val Cys
    210                 215                 220
Ser Ala Ser Ser Val Asp Val Asn Phe Asp Val Phe Leu Gln His Asn
225                 230                 235                 240
Asn Thr Lys Leu Ala Ile Pro Gln Gln Ser Asp Phe His Asn Asn Arg
                245                 250                 255
Tyr Gln Lys Val Leu Thr Leu Asn Leu Asp Gln Val Asp Phe Gln His
            260                 265                 270
Ala Gly Asn Tyr Ser Cys Val Ala Ser Asn Val Gln Gly Lys His Ser
        275                 280                 285
```

```
Thr Ser Met Phe Phe Arg Val Val Glu Ser Ala Tyr Leu Asn Leu Ser
    290             295             300

Ser Glu Gln Asn Leu Ile Gln Glu Val Thr Val Gly Glu Gly Leu Asn
305             310             315                 320

Leu Lys Val Met Val Glu Ala Tyr Pro Gly Leu Gln Gly Phe Asn Trp
                325             330             335

Thr Tyr Leu Gly Pro Phe Ser Asp His Gln Pro Glu Pro Lys Leu Ala
            340             345             350

Asn Ala Thr Thr Lys Asp Thr Tyr Arg His Thr Phe Thr Leu Ser Leu
        355             360             365

Pro Arg Leu Lys Pro Ser Glu Ala Gly Arg Tyr Ser Phe Leu Ala Arg
    370             375             380

Asn Pro Gly Gly Trp Arg Ala Leu Thr Phe Glu Leu Thr Leu Arg Tyr
385             390             395                 400

Pro Pro Glu Val Ser Val Ile Trp Thr Phe Ile Asn Gly Ser Gly Thr
                405             410             415

Leu Leu Cys Ala Ala Ser Gly Tyr Pro Gln Pro Asn Val Thr Trp Leu
            420             425             430

Gln Cys Ser Gly His Thr Asp Arg Cys Asp Glu Ala Gln Val Leu Gln
        435             440             445

Val Trp Asp Asp Pro Tyr Pro Glu Val Leu Ser Gln Glu Pro Phe His
    450             455             460

Lys Val Thr Val Gln Ser Leu Leu Thr Val Glu Thr Leu Glu His Asn
465             470             475                 480

Gln Thr Tyr Glu Cys Arg Ala His Asn Ser Val Gly Ser Gly Ser Trp
                485             490             495

Ala Phe Ile Pro Ile Ser Ala Gly Ala His Gly Phe Glu Pro Lys Ser
            500             505             510

Ser Asp Lys Thr His Thr Cys Pro Pro Cys Pro Ala Pro Glu Leu Leu
        515             520             525

Gly Gly Pro Ser Val Phe Leu Phe Pro Pro Lys Pro Lys Asp Thr Leu
    530             535             540

Met Ile Ser Arg Thr Pro Glu Val Thr Cys Val Val Val Asp Val Ser
545             550             555                 560

His Glu Asp Pro Glu Val Lys Phe Asn Trp Tyr Val Asp Gly Val Glu
                565             570             575

Val His Asn Ala Lys Thr Lys Pro Arg Glu Glu Gln Tyr Asn Ser Thr
            580             585             590

Tyr Arg Val Val Ser Val Leu Thr Val Leu His Gln Asp Trp Leu Asn
        595             600             605

Gly Lys Glu Tyr Lys Cys Lys Val Ser Asn Lys Ala Leu Pro Ala Pro
    610             615             620

Ile Glu Lys Thr Ile Ser Lys Ala Lys Gly Gln Pro Arg Glu Pro Gln
625             630             635                 640

Val Tyr Thr Leu Pro Pro Ser Arg Asp Glu Leu Thr Lys Asn Gln Val
                645             650             655

Ser Leu Thr Cys Leu Val Lys Gly Phe Tyr Pro Ser Asp Ile Ala Val
            660             665             670

Glu Trp Glu Ser Asn Gly Gln Pro Glu Asn Asn Tyr Lys Thr Thr Pro
        675             680             685

Pro Val Leu Asp Ser Asp Gly Ser Phe Phe Leu Tyr Ser Lys Leu Thr
    690             695             700

Val Asp Lys Ser Arg Trp Gln Gln Gly Asn Val Phe Ser Cys Ser Val
705             710             715                 720
```

```
Met His Glu Ala Leu His Asn His Tyr Thr Gln Lys Ser Leu Ser Leu
                725                 730                 735

Ser Pro Gly Lys
            740

<210> SEQ ID NO 37
<211> LENGTH: 745
<212> TYPE: PRT
<213> ORGANISM: Artificial Sequence
<220> FEATURE:
<223> OTHER INFORMATION: mCSF1R-ECD.511-Fc with signal peptide

<400> SEQUENCE: 37

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
                20                  25                  30

Glu Pro Gly Glu Thr Val Thr Leu Arg Cys Val Ser Asn Gly Ser Val
            35                  40                  45

Glu Trp Asp Gly Pro Ile Ser Pro Tyr Trp Thr Leu Asp Pro Glu Ser
    50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
            100                 105                 110

Gln Glu Val Thr Val Val Glu Gly Gln Glu Ala Val Leu Pro Cys Leu
        115                 120                 125

Ile Thr Asp Pro Ala Leu Lys Asp Ser Val Ser Leu Met Arg Glu Gly
130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
            180                 185                 190

Leu Lys Val Asn Arg Val His Pro Glu Pro Pro Gln Ile Lys Leu Glu
        195                 200                 205

Pro Ser Lys Leu Val Arg Ile Arg Gly Glu Ala Ala Gln Ile Val Cys
210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335
```

```
Thr Tyr Leu Gly Pro Phe Phe Glu Asp Gln Arg Lys Leu Glu Phe Ile
        340                 345                 350

Thr Gln Arg Ala Ile Tyr Arg Tyr Thr Phe Lys Leu Phe Leu Asn Arg
            355                 360                 365

Val Lys Ala Ser Glu Ala Gly Gln Tyr Phe Leu Met Ala Gln Asn Lys
370                 375                 380

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
                405                 410                 415

Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
            435                 440                 445

Asn Asp Thr His Pro Glu Val Leu Ser Gln Lys Pro Phe Asp Lys Val
        450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
                485                 490                 495

Arg Ala Val Ser Leu Gly Gln Ser Lys Gln Leu Pro Asp Glu Ser Gly
            500                 505                 510

Phe Glu Pro Lys Ser Ser Asp Lys Thr His Thr Cys Pro Pro Cys Pro
        515                 520                 525

Ala Pro Glu Leu Leu Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 38
```

```
<211> LENGTH: 740
<212> TYPE: PRT
<213> ORGANISM: Artificial Sequence
<220> FEATURE:
<223> OTHER INFORMATION: mCSF1R-ECD.506-Fc with signal peptide and GS
      linker

<400> SEQUENCE: 38

Met Glu Leu Gly Pro Pro Leu Val Leu Leu Leu Ala Thr Val Trp His
1               5                   10                  15

Gly Gln Gly Ala Pro Val Ile Glu Pro Ser Gly Pro Glu Leu Val Val
            20                  25                  30

Glu Pro Gly Glu Thr Val Thr Leu Arg Cys Val Ser Asn Gly Ser Val
        35                  40                  45

Glu Trp Asp Gly Pro Ile Ser Pro Tyr Trp Thr Leu Asp Pro Glu Ser
    50                  55                  60

Pro Gly Ser Thr Leu Thr Thr Arg Asn Ala Thr Phe Lys Asn Thr Gly
65                  70                  75                  80

Thr Tyr Arg Cys Thr Glu Leu Glu Asp Pro Met Ala Gly Ser Thr Thr
                85                  90                  95

Ile His Leu Tyr Val Lys Asp Pro Ala His Ser Trp Asn Leu Leu Ala
            100                 105                 110

Gln Glu Val Thr Val Val Glu Gly Gln Glu Ala Val Leu Pro Cys Leu
        115                 120                 125

Ile Thr Asp Pro Ala Leu Lys Asp Ser Val Ser Leu Met Arg Glu Gly
    130                 135                 140

Gly Arg Gln Val Leu Arg Lys Thr Val Tyr Phe Phe Ser Pro Trp Arg
145                 150                 155                 160

Gly Phe Ile Ile Arg Lys Ala Lys Val Leu Asp Ser Asn Thr Tyr Val
                165                 170                 175

Cys Lys Thr Met Val Asn Gly Arg Glu Ser Thr Ser Thr Gly Ile Trp
            180                 185                 190

Leu Lys Val Asn Arg Val His Pro Glu Pro Pro Gln Ile Lys Leu Glu
        195                 200                 205

Pro Ser Lys Leu Val Arg Ile Arg Gly Glu Ala Ala Gln Ile Val Cys
    210                 215                 220

Ser Ala Thr Asn Ala Glu Val Gly Phe Asn Val Ile Leu Lys Arg Gly
225                 230                 235                 240

Asp Thr Lys Leu Glu Ile Pro Leu Asn Ser Asp Phe Gln Asp Asn Tyr
                245                 250                 255

Tyr Lys Lys Val Arg Ala Leu Ser Leu Asn Ala Val Asp Phe Gln Asp
            260                 265                 270

Ala Gly Ile Tyr Ser Cys Val Ala Ser Asn Asp Val Gly Thr Arg Thr
        275                 280                 285

Ala Thr Met Asn Phe Gln Val Val Glu Ser Ala Tyr Leu Asn Leu Thr
    290                 295                 300

Ser Glu Gln Ser Leu Leu Gln Glu Val Ser Val Gly Asp Ser Leu Ile
305                 310                 315                 320

Leu Thr Val His Ala Asp Ala Tyr Pro Ser Ile Gln His Tyr Asn Trp
                325                 330                 335

Thr Tyr Leu Gly Pro Phe Phe Glu Asp Gln Arg Lys Leu Glu Phe Ile
            340                 345                 350

Thr Gln Arg Ala Ile Tyr Arg Tyr Thr Phe Lys Leu Phe Leu Asn Arg
        355                 360                 365

Val Lys Ala Ser Glu Ala Gly Gln Tyr Phe Leu Met Ala Gln Asn Lys
    370                 375                 380
```

Ala Gly Trp Asn Asn Leu Thr Phe Glu Leu Thr Leu Arg Tyr Pro Pro
385                 390                 395                 400

Glu Val Ser Val Thr Trp Met Pro Val Asn Gly Ser Asp Val Leu Phe
            405                 410                 415

Cys Asp Val Ser Gly Tyr Pro Gln Pro Ser Val Thr Trp Met Glu Cys
            420                 425                 430

Arg Gly His Thr Asp Arg Cys Asp Glu Ala Gln Ala Leu Gln Val Trp
            435                 440                 445

Asn Asp Thr His Pro Glu Val Leu Ser Gln Lys Pro Phe Asp Lys Val
        450                 455                 460

Ile Ile Gln Ser Gln Leu Pro Ile Gly Thr Leu Lys His Asn Met Thr
465                 470                 475                 480

Tyr Phe Cys Lys Thr His Asn Ser Val Gly Asn Ser Ser Gln Tyr Phe
            485                 490                 495

Arg Ala Val Ser Leu Gly Gln Ser Lys Gln Gly Phe Glu Pro Lys Ser
            500                 505                 510

Ser Asp Lys Thr His Thr Cys Pro Pro Cys Pro Ala Pro Glu Leu Leu
        515                 520                 525

Gly Gly Pro Ser Val Phe Leu Phe Pro Pro Lys Pro Lys Asp Thr Leu
        530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
            565                 570                 575

Val His Asn Ala Lys Thr Lys Pro Arg Glu Glu Gln Tyr Asn Ser Thr
            580                 585                 590

Tyr Arg Val Val Ser Val Leu Thr Val Leu His Gln Asp Trp Leu Asn
            595                 600                 605

Gly Lys Glu Tyr Lys Cys Lys Val Ser Asn Lys Ala Leu Pro Ala Pro
        610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Asp Glu Leu Thr Lys Asn Gln Val
            645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
        690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
            725                 730                 735

Ser Pro Gly Lys
            740

<210> SEQ ID NO 39
<211> LENGTH: 2214
<212> TYPE: DNA
<213> ORGANISM: Artificial Sequence
<220> FEATURE:
<223> OTHER INFORMATION: hCSF1R-ECD.506-Fc with signal sequence

<400> SEQUENCE: 39

```
atgggcccag gagttctgct gctcctgctg gtggccacag cttggcatgg tcagggaatc    60
ccagtgatag agcccagtgt ccctgagctg gtcgtgaagc caggagcaac ggtgaccttg   120
cgatgtgtgg gcaatggcag cgtggaatgg gatggccccc catcacctca ctggaccctg   180
tactctgatg gctccagcag catcctcagc accaacaacg ctaccttcca aaacacgggg   240
acctatcgct gcactgagcc tggagacccc ctgggaggca gcgccgccat ccacctctat   300
gtcaaagacc ctgcccggcc ctgaacgtg ctagcacagg aggtggtcgt gttcgaggac    360
caggacgcac tactgccctg tctgctcaca gacccggtgc tggaagcagg cgtctcgctg   420
gtgcgtgtgc gtggccggcc cctcatgcgc cacaccaact actccttctc gccctggcat   480
ggcttcacca tccacagggc caagttcatt cagagccagg actatcaatg cagtgccctg   540
atgggtggca ggaaggtgat gtccatcagc atccggctga agtgcagaa agtcatccca    600 gggcccccag ccttgacact ggtgcctgca gagctggtgc ggattcgagg ggaggctgcc   660
cagatcgtgt gctcagccag cagcgttgat gttaactttg atgtcttcct ccaacacaac   720
aacaccaagc tcgcaatccc tcaacaatct gactttcata ataaccgtta ccaaaaagtc   780
ctgaccctca acctcgatca agtagatttc caacatgccg gcaactactc ctgcgtggcc   840
agcaacgtgc agggcaagca ctccacctcc atgttcttcc gggtggtaga gagtgcctac   900
ttgaacttga gctctgagca gaacctcatc caggaggtga ccgtgggga ggggctcaac   960 ctcaaagtca tggtggaggc ctacccaggc ctgcaaggtt taactggac ctacctggga    1020 cccttttctg accaccagcc tgagcccaag cttgctaatg ctaccaccaa ggacacatac   1080
aggcacacct tcaccctctc tctgcccgc ctgaagccct ctgaggctgg ccgctactcc   1140
ttcctggcca gaaacccagg aggctggaga gctctgacgt ttgagctcac ccttcgatac   1200
cccccagagg taagcgtcat atggacattc atcaacggct ctggcaccct tttgtgtgct   1260
gcctctgggt accccagcc caacgtgaca tggctgcagt gcagtggcca cactgatagg   1320
tgtgatgagg cccaagtgct gcaggtctgg gatgacccat accctgaggt cctgagccag   1380
gagcccttcc acaaggtgac ggtgcagagc ctgctgactg ttgagacctt agagcacaac   1440
caaacctacg agtgcagggc ccacaacagc gtggggagtg gctcctgggc cttcataccc   1500
atctctgcag gagcccacga gcccaaatct tctgacaaaa ctcacacatg cccaccgtgc   1560
ccagcacctg aactcctggg gggaccgtca gtcttcctct tccccccaaa acccaaggac   1620
accctcatga tctcccggac ccctgaggtc acatgcgtgg tggtggacgt gagccacgaa   1680
gaccctgagg tcaagttcaa ctggtacgtg gacggcgtgg aggtgcataa tgccaagaca   1740
aagccgcggg aggagcagta caacagcacg taccgtgtgg tcagcgtcct caccgtcctg   1800
caccaggact ggctgaatgg caaggagtac aagtgcaagg tctccaacaa agccctccca   1860
gcccccatcg agaaaaccat ctccaaagcc aaagggcagc cccgagaacc acaggtgtac   1920
accctgcccc catcccggga tgagctgacc aagaaccagg tcagcctgac ctgcctggtc   1980
aaaggcttct atcccagcga catcgccgtg gagtgggaga gcaatgggca gccggagaac   2040
aactacaaga ccacgcctcc cgtgctggac tccgacggct ccttcttcct ctacagcaag   2100
ctcaccgtgg acaagagcag gtggcagcag gggaacgtct tctcatgctc cgtgatgcat   2160
gaggctctgc acaaccacta cacgcagaag agcctctccc tgtctccggg taaa         2214
```

<210> SEQ ID NO 40
<211> LENGTH: 2157
<212> TYPE: DNA
<213> ORGANISM: Artificial Sequence
<220> FEATURE:

<223> OTHER INFORMATION: hCSF1R-ECD.506-Fc

<400> SEQUENCE: 40

```
atcccagtga tagagcccag tgtccctgag ctggtcgtga agccaggagc aacggtgacc      60
ttgcgatgtg tgggcaatgg cagcgtggaa tgggatggcc ccccatcacc tcactggacc     120
ctgtactctg atggctccag cagcatcctc agcaccaaca cgctaccttt ccaaaacacg     180
gggacctatc gctgcactga gcctggagac ccctgggag cagcgccgc catccacctc      240
tatgtcaaag accctgcccg gcctggaac gtgctagcac aggaggtggt cgtgttcgag     300
gaccaggacg cactactgcc ctgtctgctc acagacccgg tgctggaagc aggcgtctcg     360
ctggtgcgtg tgcgtggccg gcccctcatg cgccacacca actactcctt ctcgccctgg     420
catggcttca ccatccacag ggccaagttc attcagagcc aggactatca atgcagtgcc     480
ctgatgggtg gcaggaaggt gatgtccatc agcatccggc tgaaagtgca gaaagtcatc     540
ccagggcccc cagccttgac actggtgcct gcagagctgg tgcggattcg aggggaggct     600
gcccagatcg tgtgctcagc cagcagcgtt gatgttaact ttgatgtctt cctccaacac     660
aacaacacca agctcgcaat ccctcaacaa tctgactttc ataataaccg ttaccaaaaa     720
gtcctgaccc tcaacctcga tcaagtagat ttccaacatg ccggcaacta ctcctgcgtg     780
gccagcaacg tgcagggcaa gcactccacc tccatgttct ccgggtggt agagagtgcc     840
tacttgaact tgagctctga gcagaacctc atccaggagg tgaccgtggg ggaggggctc     900
aacctcaaag tcatggtgga ggcctaccca ggcctgcaag gttttaactg gacctacctg     960
ggacccttt ctgaccacca gcctgagccc aagcttgcta atgctaccac caaggacaca    1020
tacaggcaca ccttcacccct ctctctgccc cgcctgaagc cctctgaggc tggccgctac    1080
tccttcctgg ccagaaaccc aggaggctgg agagctctga cgtttgagct caccccttcga    1140
tacccccag aggtaagcgt catatggaca ttcatcaacg gctctggcac ccttttgtgt    1200
gctgcctctg ggtacccca gcccaacgtg acatggctgc agtgcagtgg ccacactgat    1260
aggtgtgatg aggcccaagt gctgcaggtc tgggatgacc cataccctga ggtcctgagc    1320
caggagccct tccacaaggt gacggtgcag agcctgctga ctgttgagac cttagagcac    1380
aaccaaacct acgagtgcag ggcccacaac agcgtgggga gtggctcctg gccttcata    1440
cccatctctg caggagccca cgagcccaaa tcttctgaca aaactcacac atgcccaccg    1500
tgcccagcac ctgaactcct ggggggaccg tcagtcttcc tcttcccccc aaaacccaag    1560
gacaccctca tgatctcccg gacccctgag gtcacatgcg tggtggtgga cgtgagccac    1620
gaagaccctg aggtcaagtt caactggtac gtggacggcg tggaggtgca taatgccaag    1680
acaaagccgc gggaggagca gtacaacagc acgtaccgtg tggtcagcgt cctcaccgtc    1740
ctgcaccagg actggctgaa tggcaaggag tacaagtgca aggtctccaa caaagccctc    1800
ccagccccca tcgagaaaac catctccaaa gccaagggc agccccgaga accacaggtg    1860
tacaccctgc ccccatcccg ggatgagctg accaagaacc aggtcagcct gacctgcctg    1920
gtcaaaggct tctatcccag cgacatcgcc gtggagtggg agagcaatgg gcagccggag    1980
aacaactaca agaccacgcc tcccgtgctg gactccgacg gctccttctt cctctacagc    2040
aagctcaccg tggacaagag caggtggcag caggggaacg tcttctcatg ctccgtgatg    2100
catgaggctc tgcacaacca ctacacgcag aagagcctct ccctgtctcc gggtaaa       2157
```

COLONY STIMULATING FACTOR 1 RECEPTOR (CSF1R) EXTRACELLULAR DOMAIN FUSION MOLECULES

This application claims priority to U.S. Provisional Patent Application Nos. 61/118,423 and 61/118,425, each filed on Nov. 26, 2008, and which are incorporated herein by reference in their entirety.

TECHNICAL FIELD

The present invention relates to specific CSF1R ECD fusion molecules that exhibit improved therapeutic properties. The invention also relates to polypeptide and polynucleotide sequences, vectors, host cells, and compositions comprising or encoding such molecules. The invention also relates to methods of making and using the CSF1R ECD fusion molecules. The invention further relates to methods of treatment using the CSF1R ECD fusion molecules. For example, certain CSF1R ECDs of the invention may be used to treat rheumatoid arthritis (RA) or multiple sclerosis (MS).

BACKGROUND AND SUMMARY OF THE INVENTION

Rheumatoid arthritis (RA) is a chronic disease, characterized primarily by inflammation of the lining (synovium), of the joints, which can lead to long-term joint damage, resulting in chronic pain, loss of function, and disability. RA is an autoimmune disease that affects 1% of the U.S. population (2.1 million Americans), with a significantly higher occurrence among women than men. In RA, the membranes or tissues (synovial membranes) lining the joints become inflamed (synovitis). Over time, the inflammation may destroy the joint tissues, leading to disability. Because RA can affect multiple organs of the body, rheumatoid arthritis is referred to as a systemic illness. The onset of RA is usually in middle age, but frequently occurs in one's 20s and 30s.

RA progresses in three stages. The first stage involves the swelling of the lining of the joints, causing pain, warmth, stiffness, redness, and swelling around the joint. The second stage involves the thickening of the lining of the joints. During the third stage, the inflamed cells release enzymes that may digest bone and cartilage, often causing the involved joint to lose its shape and alignment, and leading to increased pain and loss of movement. Rheumatoid arthritis can start in any joint, but it most commonly begins in the smaller joints of the fingers, hands and wrists. Joint involvement is usually symmetrical, meaning that if a joint hurts on the left hand, the same joint will hurt on the right hand. In general, more joint erosion indicates more severe disease activity.

Other RA-associated symptoms include fatigue, stiffness, weakness, flu-like symptoms, including a low-grade fever, pain associated with prolonged sitting, the occurrence of flares of disease activity followed by remission or disease inactivity, rheumatoid nodules (lumps of tissue under the skin), muscle pain, loss of appetite, depression, weight loss, anemia, cold or sweaty hands and feet, and involvement of the glands around the eyes and mouth leading to decreased production of tears and saliva (Sjögren's syndrome). Advanced changes include damage to cartilage, tendons, ligaments and bone, which causes deformity and instability in the joints. The damage can lead to limited range of motion, resulting in daily tasks (grasping a fork, combing hair, buttoning a shirt) becoming more difficult. Skin ulcers and a general decline in health may also occur.

At present, RA is a chronic disease that can be controlled, but not cured. The goal of treatments is relief of symptoms and preventing the disease from worsening. Current methods of treatment of RA are focused on relieving pain, reducing inflammation, stopping or slowing joint damage, and improving a person's ability to function.

Nonsteroidal anti-inflammatory drugs (NSAIDs), including aspirin, ibuprofen, indomethacin, and COX-2 inhibitors such as valdecoxib and celecoxib, can be used to reduce inflammation and relieve pain. However, NSAIDs do not control the disease or inhibit disease progression. Analgesic drugs, including acetaminophen, propoxyphene, meperidine, and morphine, may be used to relieve pain, but they do not reduce inflammation, control the disease, or inhibit disease progression. Glucocorticoids or prednisone may be used at low maintenance doses to slow joint damage due to inflammation, but long-term use is not recommended. Disease-modifying anti-rheumatic drugs (DMARDs) are used to control the progression of RA and to try to prevent joint deterioration and disability. These anti-rheumatic drugs are often given in combination with other anti-rheumatic drugs or with other medications, such as NSAIDs or prednisone. Examples of DMARDs prescribed for rheumatoid arthritis include antimalarial medications, such as hydroxychloroquine or chloroquine, methotrexate, sulfasalazine, and oral gold. Biologic response modifiers, which directly modify the immune system by inhibiting cytokines, are also used to inhibit inflammation and RA progression. Examples of biologic response modifiers include etanercept, infliximab, adalimumab and anakinra. Some of the DMARDs and biologic response modifiers can take up to six months to work, and many have serious side effects. Protein-A immunoadsorption therapy is also used to inhibit inflammation by filtering the blood to remove antibodies and immune complexes that promote inflammation; however, this therapy offers only temporary relief of RA-associated inflammation.

Multiple sclerosis (MS) is also a chronic and potentially debilitating disease. MS affects the central nervous system (CNS), which is made up of the brain and spinal cord. MS is widely believed to be an autoimmune disease in which the body generates antibodies and white blood cells against cells that produce the myelin sheath. The myelin sheath is the fatty substance that insulates nerve fibers in the CNS, and an onslaught of the myelin sheath by such antibodies or white blood cells leads to inflammation, injury, and detachment of the myelin sheath from the nerve fiber (called demyelination). Demyelination can ultimately lead to injury of the nerves that the myelin sheath originally surrounded. Demyelination can lead to multiple areas of scarring (called sclerosis) in the CNS. Eventually, the damage induced by demyelination can slow or block nerve signals that control muscle coordination, strength, sensation, and vision. MS affects an estimated 300,000 people in the U.S. and is predicted to affect more than 1 million people worldwide. Most people first experience MS symptoms between the ages of 20 and 40 years.

MS symptoms vary depending on the location of the sclerosis and the affected nerve fibers. MS-associated symptoms may include: numbness in one or more limbs (typically occurring on one side of the body at a time, or on the bottom half of the body), partial or complete loss of vision (usually in one eye at a time, and often accompanied by pain during eye movement), double vision or blurring of vision, electric shock sensations that occur with certain head movements, tremors, lack of coordination or unsteady gait, fatigue, dizziness, muscle stiffness or spasticity, slurred speech, paralysis, problems with bladder, bowel, or sexual function, and mental changes, such as forgetfulness or difficulties with concentration.

Current treatments for MS include beta interferons (interferon beta-1b and interferon beta-1a, which help fight viral infection and regulate the immune system; these medications reduce but do not eliminate flare-ups. Beta interferons do not reverse damage, and have not been proven to significantly alter the long-term development of permanent disability. Furthermore, some individuals develop antibodies against beta interferons, which may make them less effective. Glatiramer is an alternative to beta interferons used to treat MS and it is believed to block the immune system's attack on myelin. Natalizumab is an antibody drug that blocks the attachment of immune cells to brain blood vessels, which is required for immune cells to enter the brain, thereby reducing the inflammatory action of immune cells on the nerve cells of the brain. However, natalizumab has been associated with a rare, often fatal, brain disorder called progressive multifocal leukoencephalopathy and is thus considered a high risk treatment option. The chemotherapy drug mitoxantrone has been approved for the treatment of certain aggressive forms of MS. However, due to serious side effects, such as heart damage, mitoxantrone is not used for long-term MS treatment, and it is reserved for individuals with severe attacks or rapidly advancing disease who fail to respond to other treatments.

Thus, a need exists for new, therapeutically effective drugs for the treatment of RA. Furthermore, none of the available MS therapies provide an ideal MS treatment option. Thus, there also remains a need in the art for the identification of additional agents with a demonstrated ability to treat MS in vivo. The colony stimulating factor 1 receptor (referred to herein as CSF1R; also referred to in the art as FMS, FIM2, C-FMS, and CD115) is a single-pass transmembrane receptor with an N-terminal extracellular domain (ECD) and a C-terminal intracellular domain with tyrosine kinase activity. Ligand binding of the colony stimulating factor 1 ligand (referred to herein as CSF1; also referred to in the art as MCSF and MGC31930); or the interleukin 34 ligand (referred to herein as IL34; also referred to in the art as C16orf77 and MGC34647) to CSF1R leads to receptor dimerization, upregulation of CSF1R protein tyrosine kinase activity, phosphorylation of CSF1R tyrosine residues, and downstream signaling events. Both CSF1 and IL34 stimulate monocyte survival, proliferation, and differentiation into macrophages. However, IL34 was discovered recently, and its overall functions have not been fully established.

Disregulation of CSF1R activity may result in an imbalance in the levels and/or activities of macrophage cell populations, which may lead to autoimmune disease and RA-associated pathology. Based on their known and suspected contributions to human autoimmune disease, both CSF1R and CSF1 have been identified as potential therapeutic targets for RA. Indeed, CSF1R and CSF1 antagonists, such as antibodies directed against CSF1R or CSF1 (see e.g., Kitaura et al., *The Journal of Clinical Investigation* 115(12):3418-3427 (2005), and WO 2007/081879), antisense- and siRNA-mediated silencing of CSF1R or CSF1 expression (see e.g., WO 2007/081879), soluble forms of the CSF1R ECD (see e.g., WO 2007/081879), and small molecule inhibitors of CSF1R tyrosine kinase activity (see e.g., Irvine et al., *The FASEB Journal* 20: 1315-1326 (2006), and Ohno et al., *Clinical Immunology* 38: 283-291 (2008)) and inhibitors of CSF1 (see e.g., WO 2007/081879), have been proposed for targeting RA. Despite the proposed utility of such CSF1R and CSF1 antagonists, there remains a need in the art for the identification of additional agents with a demonstrated ability to treat RA in vivo.

The inventors have also found that certain of the CSF1R ECD fusion molecules exhibit improved properties, including improvements to therapeutically relevant properties. For example, the inventors have found that expression of CSF1R ECD fusion molecules in CHO cells results in more highly sialylated CSF1R ECD fusion molecules, which are more stable than such fusion molecules produced in 293-6E cells. Also, the inventors have found that a CSF1R ECD fusion molecule wherein the CSF1R ECD has the amino acid sequence of SEQ ID NO.:2 (amino acids 20-506 of the human CSF1R protein) binds the CSF1R ligands CSF1 and IL34 more tightly and more effectively inhibits monocyte growth in an in vitro assay than a full-length CSF1R ECD fusion molecule wherein the CSF1R ECD has the amino acid sequence of SEQ ID NO.:1 (amino acids 20-512 of the human CSF1R protein). Thus, this CSF1R ECD fusion molecule provides a particularly attractive therapeutic molecule.

The inventors have also found that CSF1R ECD fusion molecules are effective in treating MS and RA in in vivo models (See Examples 8, 9, and 13). Furthermore, CSF1R ECD fusion molecules are also effective to deplete particular classes of monocytes from peripheral blood and spleen, respectively, as shown in Examples 7 and 14. Accordingly, some embodiments of the application include methods and compositions for treating RA or MS. Other embodiments of the invention further include methods and compositions for depleting peripheral blood monocytes, inhibiting monocyte viability, and inhibiting CSF1- and/or IL34-stimulated monocyte proliferation. Furthermore, in certain embodiments, CSF1R ECD fusion proteins of the invention may be used for treating other inflammatory conditions such as psoriasis, SLE (lupus), COPD, atopic dermatitis, and atherosclerosis, as well as macrophage activation syndrome and histiocytosis X.

CSF1R ECD fusion molecule of the invention include, for example, a CSF1R ECD fusion molecule and one or more fusion partners, wherein the amino acid sequence of the CSF1R ECD fusion molecule comprises SEQ ID NO.:2 (corresponding to human CSF1R ECD residues 1-506) and excludes the last six C-terminal amino acid residues of SEQ ID NO.:1 (corresponding to human CSF1R ECD residues 507-512). In such fusion molecules, any amino acid residues that follow the C-terminal residue of SEQ ID NO:2 do not begin with the amino acid sequence of residues 507-512 of SEQ ID NO:1 (THPPDE). Such fusion molecules may of course include the amino acid sequence THPPDE anywhere else in the amino acid sequence. In some such embodiments, the CSF1R ECD consists of SEQ ID NO:2.

A CSF1R ECD fusion molecule wherein the amino acid sequence of the CSF1R ECD corresponds to SEQ ID NO.:2 showed higher affinity for CSF1 and IL34 ligands than the CSF1R ECD fusion molecule wherein the amino acid sequence of the CSF1R ECD corresponds to SEQ ID NO.:1. A CSF1R ECD fusion molecule wherein the amino acid sequence of the CSF1R ECD corresponds to SEQ ID NO.:2 also inhibited monocyte viability and CSF1- and IL34-stimulated proliferation of human monocytes better than the CSF1R ECD fusion molecule wherein the amino acid sequence of the CSF1R ECD corresponds to SEQ ID NO.:1. Thus, in another aspect of the invention, the amino acid sequence of the CSF1R ECD fusion molecule comprises or consists of the hCSF1R.506-Fc fusion molecule described above (SEQ ID NO.:6).

The one or more fusion partners in any of the embodiments described previously includes, but is not limited to, an Fc, albumin, or polyethylene glycol, or both an FC and polyethylene glycol. In some embodiments, the fusion molecule comprises a linker between the CSF1R ECD and one or more fusion partners. In some such embodiments, the linker is a peptide consisting of the amino acid sequence glycine-serine. For example, in some embodiments, the CSF1R ECD fusion molecule comprises a CSF1R ECD, an Fc, and polyethylene glycol, wherein the amino acid sequence of the CSF1R ECD fusion molecule comprises or consists of SEQ ID NO.:6.

In some embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells. The present invention also provides pharmaceutical compositions comprising the CSF1R ECD fusion molecules of the invention and a pharmaceutically acceptable carrier.

The present invention further provides a polynucleotide comprising a nucleic acid sequence that encodes any one of the above described CSF1R ECD fusion molecules of the invention. In some embodiments, the amino acid sequence encoded by the polynucleotide of the invention comprises a signal peptide amino acid sequence. In some embodiments, the polynucleotide encodes an amino acid sequence comprising SEQ ID NO:2, wherein the amino acid sequence excludes the six C-terminal residues of SEQ ID NO:1. In other embodiments, the polynucleotide encodes an amino acid sequence comprising SEQ ID NO:6 plus a signal peptide amino acid sequence, such as, for example, SEQ ID NO:16. In some embodiments, the polynucleotide comprises the sequence of SEQ ID NO: 39. In some embodiments, the polynucleotide comprises the sequence of SEQ ID NO: 40. Another aspect of the invention provides an expression vector comprising the polynucleotide described above.

It has also been found that the CSF1R ECD fusion molecule is more highly sialylated when produced from CHO cells compared to the fusion molecule produced from other cells, such as 293-6E cells. Thus, the present invention also provides a CHO cell comprising an expression vector encoding the CSF1R ECD fusion molecule and a method of producing the CSF1R ECD fusion molecule of the invention from a CHO cell. For example, in some embodiments, the method comprises: (a) culturing a CHO cell comprising the polynucleotide of any one of the above described CSF1R ECD fusion molecules in conditions such that the CSF1R ECD fusion molecule is expressed; and (b) recovering the CSF1R ECD fusion molecule. The invention further includes this method with the step of fusing polyethylene glycol to the CSF1R ECD fusion molecule. The present invention further provides a method for producing glycosylated and sialylated CSF1R ECD fusion molecules. For example, in some embodiments, the CHO cell comprises a vector comprising a polynucleotide sequence that encodes the amino acid sequence of SEQ ID NO:6 plus a signal peptide amino acid sequence, such as, for example, SEQ ID NO:16. In some embodiments, the CHO cell comprises a vector comprising a polynucleotide sequence that comprises the sequence of SEQ ID NO: 39. In some embodiments, the CHO cell comprises a vector comprising a polynucleotide sequence that comprises the sequence of SEQ ID NO: 40.

Methods of the invention also comprise administering to a patient a therapeutically effective amount of a CSF1R ECD fusion molecule, wherein the fusion molecule comprises a CSF1R ECD and one or more fusion partners. The invention provides, for example, a method of treating multiple sclerosis, a method of treating rheumatoid arthritis, or a method of depleting peripheral blood monocytes in a patient comprising administering to the patient a therapeutically effective amount of a CSF1R ECD fusion molecule. In some embodiments of those methods, the CSF1R ECD of the CSF1R ECD fusion molecule comprises the full-length human CSF1R ECD (hCSF1R.512; SEQ ID NO.:1). In other embodiments, the CSF1R ECD fusion molecule comprises SEQ ID NO.:2 (corresponding to human CSF1R ECD residues 1-506) and excludes the last six C-terminal amino acid residues of SEQ ID NO.:1 (corresponding to human CSF1R ECD residues 507-512). In some such embodiments, the CSF1R ECD consists of SEQ ID NO:2. In a further aspect, the CSF1R ECD of the CSF1R ECD fusion molecule comprises the full-length CSF1R ECD of SEQ ID NO.:1, but excludes the last C-terminal amino acid residue of SEQ ID NO.:1 (referred to herein as CSF1R.511; SEQ ID NO.:26). In some such embodiments, the CSF1R ECD consists of SEQ ID NO:26 or SEQ ID NO:1.

The one or more fusion partners in any of the embodiments described previously includes, but is not limited to, an Fc, albumin, or polyethylene glycol, or both an FC and polyethylene glycol. In some embodiments, the fusion molecule comprises a linker between the CSF1R ECD and the fusion partner. In some such embodiments, the linker is a peptide consisting of the amino acid sequence glycine-serine. For example, in some embodiments, the CSF1R ECD fusion molecule comprises a CSF1R ECD, an Fc, and polyethylene glycol, wherein the amino acid sequence of the CSF1R ECD fusion molecule comprises or consists of SEQ ID NO.:6.

In some embodiments, the CSF1R ECD comprises a signal peptide. In some embodiments, the fusion molecule is glycosylated and/or sialylated. In some embodiments, the polypeptide portion of the fusion molecule is expressed in Chinese hamster ovary (CHO) cells.

DETAILED DESCRIPTION OF CERTAIN EMBODIMENTS

Figure 1:
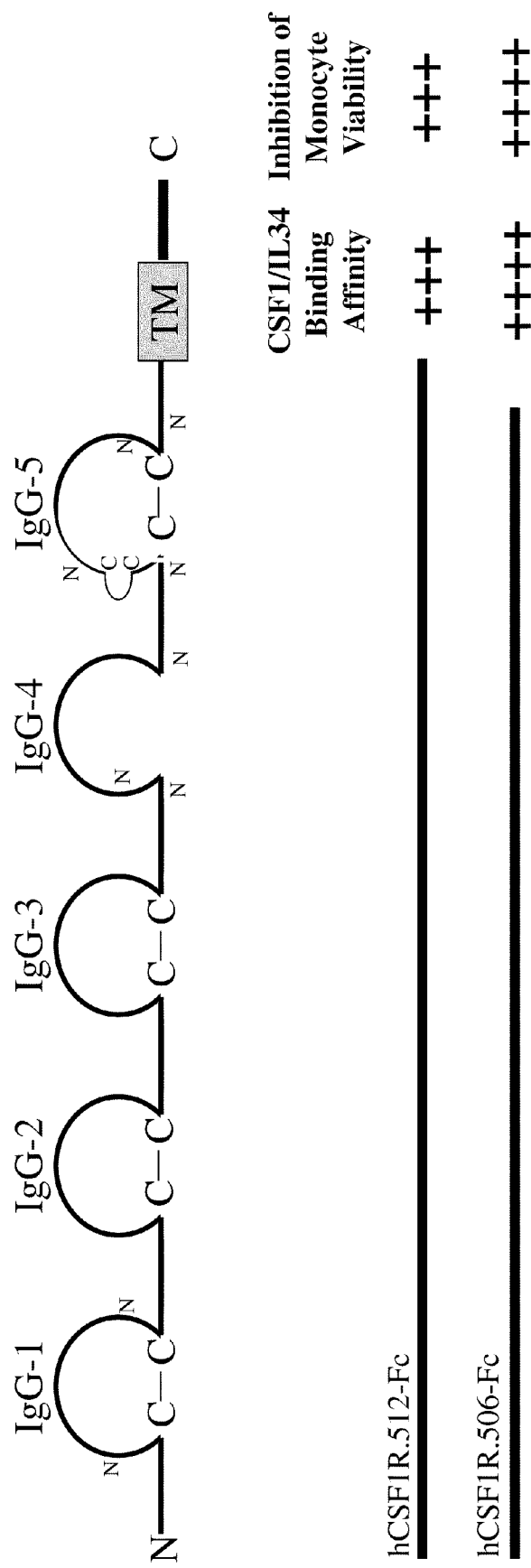
FIG. 1 shows the domain structure of the full-length human CSF1R ECD, which consists of 512 amino acid residues. The five IgG domains are denoted from N terminus to C terminus as IgG-1, IgG-2, IgG-3, IgG-4, and IgG-5. Also shown is the relative ability of the human CSF1R ECD fusion molecules, hCSF1R.512-Fc and hCSF1R.506-Fc, to bind to the CSF1 and IL34 ligands and to inhibit monocyte viability.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "CSF1R" refers herein to the full-length CSF1R, which includes the N-terminal ECD, the transmembrane domain, and the intracellular tyrosine kinase domain, with or without an N-terminal signal peptide. In one embodiment, the CSF1R is a human CSF1R having an amino acid sequence corresponding to SEQ ID NO.:22 or to SEQ ID NO.:23. In another embodiment, the CSF1R is a mouse CSF1R having an amino acid sequence corresponding to SEQ ID NO.:24 or to SEQ ID NO.:25.

The term "CSF1R extracellular domain" ("CSF1R ECD") includes full-length CSF1R ECDs, CSF1R ECD fragments, and CSF1R ECD variants. As used herein, the term "CSF1R ECD" refers to a CSF1R polypeptide that lacks the intracellular and transmembrane domains. In one embodiment, the CSF1R ECD is a human full-length CSF1R ECD having an amino acid sequence corresponding to SEQ ID NO.:1. The term "full-length CSF1R ECD", as used herein, refers to a CSF1R ECD that extends to the last amino acid of the extracellular domain, and may or may not include an N-terminal signal peptide. For example, the last amino acid of the full-length CSF1R ECD is at position 512 for the human ECD and at position 511 for the mouse ECD. Thus, a mouse full-length CSF1R ECD may consist of the amino acid sequence corresponding to SEQ ID NO.:3 (mature form) or to SEQ ID NO.:11 (with the signal peptide), and a human full-length CSF1R ECD may consist of the amino acid sequence corresponding to SEQ ID NO.:1 (mature form) or to SEQ ID NO.:13 (with the signal peptide). As used herein, the term "CSF1R ECD fragment" refers to a CSF1R ECD having one or more residues deleted from the N or C terminus of the full-length ECD and that retains the ability to bind to the CSF1 or IL34 ligand. The CSF1R ECD fragment may or may not include an N-terminal signal peptide. In one embodiment, the CSF1R ECD fragment is a human CSF1R ECD fragment having an amino acid sequence corresponding to SEQ ID NO.:2 (mature form) or to SEQ ID NO.:12 (with the signal peptide). In another embodiment, the CSF1R ECD fragment is a mouse CSF1R ECD fragment having an amino acid sequence corresponding to SEQ ID NO.:4 (mature form) or to SEQ ID NO.:14 (with the signal peptide). As used herein, the term "CSF1R ECD variants" refers to CSF1R ECDs that contain amino acid additions, deletions, and substitutions and that remain capable of binding to CSF1 or IL34. Such variants may be at least 70%, 80%, 90%, 95%, 97%, 98%, or 99% identical to the parent ECD. The % identity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences.

A polypeptide having an amino acid sequence at least, for example, 95% identical to a reference amino acid sequence of a CSF1R ECD polypeptide is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence. These alterations of the reference sequence may occur at the N- or C-terminal positions of the reference amino acid sequence or anywhere between those terminal positions, interspersed either individually among residues in the reference sequence, or in one or more contiguous groups within the reference sequence.

As a practical matter, whether any particular polypeptide is at least 70%, 80%, 90%, or 95% identical to, for instance, an amino acid sequence or to a polypeptide sequence encoded by a nucleic acid sequence set forth in the Sequence Listing can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

As used herein, the terms "hCSF1R-ECD.512" and "hCSF1R.512" may be used interchangeably to refer to the full-length human CSF1R ECD corresponding to SEQ ID NO.:1.

As used herein, the terms "hCSF1R-ECD.506" and "hCSF1R.506" may be used interchangeably to refer to the human CSF1R ECD corresponding to SEQ ID NO.:2.

As used herein, the terms "mCSF1R-ECD.511" and "mCSF1R.511" may be used interchangeably to refer to the full-length mouse CSF1R ECD corresponding to SEQ ID NO.:3.

As used herein, the terms "mCSF1R-ECD.506" and "mCSF1R.506" may be used interchangeably to refer to the mouse CSF1R ECD corresponding to SEQ ID NO.:4.

As used herein, the terms "hCSF1R-ECD.511" and "hCSF1R.511" may be used interchangeably to refer to the human CSF1R ECD corresponding to SEQ ID NO.:26.

As used herein, the term "CSF1R IgG domain" refers to one of five IgG domains that comprise the CSF1R ECD. As used herein, the five IgG domains of the CSF1R ECD include from the N terminus to C terminus, "IgG-1," "IgG-2," "IgG-3," "IgG-4," and "IgG-5."

The term "CSF1R ECD fusion molecule" refers to a molecule comprising a CSF1R ECD, and one or more "fusion partners." In certain embodiments, the CSF1R ECD and the fusion partner are covalently linked ("fused"). If the fusion partner is also a polypeptide ("the fusion partner polypeptide"), the CSF1R ECD and the fusion partner polypeptide may be part of a continuous amino acid sequence, and the fusion partner polypeptide may be linked to either the N terminus or the C terminus of the CSF1R ECD. In such cases, the CSF1R ECD and the fusion partner polypeptide may be translated as a single polypeptide from a coding sequence that encodes both the CSF1R ECD and the fusion partner polypeptide (the "CSF1R ECD fusion protein"). In certain embodiments, the CSF1R ECD and the fusion partner are covalently linked through other means, such as, for example, a chemical linkage other than a peptide bond. Many known methods of covalently linking polypeptides to other molecules (for example, fusion partners) may be used. In other embodiments, the CSF1R ECD and the fusion partner may be fused through a "linker," which is comprised of at least one amino acid or chemical moiety.

In certain embodiments, the CSF1R polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

Certain exemplary fusion partners include, but are not limited to, an immunoglobulin Fc domain, albumin, and polyethylene glycol. The amino acid sequences of certain exemplary Fc domains are shown in SEQ ID NOs.:19 to 21. In certain embodiments, there is a two amino acid residue linker consisting of an N-terminal glycine residue followed by a serine residue (GS) located between the CSF1R ECD and the Fc. The amino acid sequence of a certain exemplary N-terminal GS linker followed by an Fc is shown in SEQ ID NO.:30.

The term "signal peptide" refers to a sequence of amino acid residues located at the N terminus of a polypeptide that facilitates secretion of a polypeptide from a mammalian cell. A signal peptide may be cleaved upon export of the polypeptide from the mammalian cell, forming a mature protein. Signal peptides may be natural or synthetic, and they may be heterologous or homologous to the protein to which they are attached. Certain exemplary signal peptides include, but are not limited to, the signal peptides of CSF1R, such as, for example, the amino acid sequence of SEQ ID NOs.:9 and 10, which correspond to the human and mouse CSF1R signal peptides, respectively. Certain exemplary signal peptides may also include signal peptides from heterologous proteins. A "signal sequence" refers to a polynucleotide sequence that encodes a signal peptide. In certain embodiments, a CSF1R ECD lacks a signal peptide. In certain embodiments, a CSF1R ECD includes at least one signal peptide, which may be selected from a native CSF1R signal peptide or a heterologous signal peptide.

In certain embodiments, the CSF1R ECD amino acid sequence is derived from that of a non-human mammal. In such embodiments, the CSF1R ECD amino acid sequence may be derived from mammals including, but not limited to, rodents, simians, felines, canines, equines, bovines, porcines, ovines, caprines, mammalian laboratory animals, mammalian farm animals, mammalian sport animals, and mammalian pets. CSF1R ECD fusion molecules incorporating a non-human CSF1R ECD are termed "non-human CSF1R ECD fusion molecules." Similar to the human CSF1R ECD fusion molecules, non-human fusion molecules may comprise a fusion partner, optional linker, and a CSF1R ECD. Such non-human fusion molecules may also include a signal peptide. Examples of non-human CSF1R ECDs are SEQ ID NOs:3 and 13, which correspond to the mouse CSF1R ECD.511 sequence with and without a signal peptide, and SEQ ID NOs:4 and 14, which correspond to the mouse CSF1R ECD.506 sequence without and with a signal peptide. Examples of non-human fusion molecules are SEQ ID NOs: 7, 8, 33, and 34. A "non-human CSF1R ECD fragment" refers to a non-human CSF1R ECD having one or more residues deleted from the N or C terminus of the full-length ECD and that retains the ability to bind to the CSF1 or IL34 ligands of the non-human animal from which the sequence was derived.

See, e.g., SEQ ID NOs:4 and 14. A "non-human CSF1R ECD variant" refers to CSF1R ECDs that contain amino acid additions, deletions, and substitutions and that remain capable of binding to CSF1 or IL34 from the animal from which the sequence was derived. In some embodiments, the last five or the last six C-terminal amino acid residues of the non-human full length CSF1R ECD may be deleted, for example. See, e.g., SEQ ID NOs:4 and 14.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., (β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Certain exemplary mammalian cells include, but are not limited to, 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

The term "rheumatoid arthritis" ("RA") refers to a chronic autoimmune disease characterized primarily by inflammation of the lining (synovium) of the joints, which can lead to joint damage, resulting in chronic pain, loss of function, and disability. Because RA can affect multiple organs of the body, including skin, lungs, and eyes, it is referred to as a systemic illness.

The term "multiple sclerosis" ("MS") refers to the chronic, autoimmune, demyelinating disease of the CNS in which the body generates antibodies and white blood cells against the cells that produce the myelin sheath. "Demyelination" occurs when the myelin sheath becomes inflamed, injured, and detaches from the nerve fiber.

"Treatment," as used herein, covers any administration or application of a therapeutic for disease in a mammal, including a human, and includes inhibiting the disease or progression of the disease, partially inhibiting or slowing the disease or its progression, arresting its development, partially or fully relieving the disease, or curing the disease, for example, by causing regression, or restoring or repairing a lost, missing, or defective function; or stimulating an inefficient process.

The terms "inhibition" or "inhibit" refer to a decrease or cessation of any phenotypic characteristic or to the decrease or cessation in the incidence, degree, or likelihood of that characteristic.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

CSF1R Extracellular Domains

Certain exemplary CSF1R ECDs include full-length CSF1R ECDs, CSF1R ECD fragments, and CSF1R ECD variants. CSF1R ECDs may include or lack a signal peptide. Exemplary CSF1R ECDs include, but are not limited to, CSF1R ECDs having amino acid sequences selected from SEQ ID NOs.:1, 2, 11, 12, 26, and 27 for human CSF1R, and SEQ ID NOs.:3, 4, 13, and 14 for mouse CSF1R. In certain embodiments, a CSF1R ECD is isolated.

The inventors have discovered that a human CSF1R ECD fusion molecule wherein the CSF1R ECD has the amino acid sequence corresponding to SEQ ID NO.:2 exhibits properties that will be particularly useful with respect to the treatment of disease, including treatment of inflammatory diseases, rheumatoid arthritis and multiple sclerosis. The inventors have found that this fusion molecule binds more tightly to the CSF1R ligands, CSF1 and IL34, compared to the full-length human CSF1R ECD fusion molecule wherein the CSF1R ECD has the amino acid sequence corresponding to SEQ ID NO.:1. Furthermore, the CSF1R ECD fusion molecule wherein the CSF1R ECD has the amino acid sequence corresponding to SEQ ID NO.:2 more effectively inhibits monocyte growth compared to the full-length human CSF1R ECD fusion molecule wherein the CSF1R ECD has the amino acid sequence corresponding to SEQ ID NO.:1.

CSF1R ECD Fragments

Non-limiting exemplary CSF1R ECD fragments include the human CSF1R ECD in which the last six C-terminal amino acid residues of the full-length CSF1R ECD are removed, but in which all five IgG domains are maintained (hCSF1R.506), the human CSF1R ECD in which the last C-terminal amino acid residue of the full-length CSF1R ECD is removed, but in which all five IgG domains are maintained (hCSF1R.511), and the mouse CSF1R ECD in which the last five C-terminal amino acid residues of the full-length CSF1R ECD are removed, but in which all five IgG domains are maintained (mCSF1R.506).

CSF1R ECD fragments may include or lack a signal peptide. Exemplary CSF1R ECD fragments include, but are not limited to, CSF1R ECD fragments having amino acid sequences selected from SEQ ID NOs.:2, 12, 26, and 27 for human CSF1R, and SEQ ID NOs.:4 and 14 for mouse CSF1R.

Fusion Partners and Conjugates As discussed, the CSF1R ECD of the present invention may be combined with a fusion partner polypeptide, resulting in a CSF1R ECD fusion protein. These fusion partner polypeptides may facilitate purification, and the CSF1R ECD fusion proteins may show an increased half-life in vivo. Fusion partner polypeptides that have a disulfide-linked dimeric structure due to the IgG portion may also be more efficient in binding and neutralizing other molecules than the monomeric CSF1R ECD fusion protein or the CSF1R ECD alone. Suitable fusion partners of a CSF1R ECD include, for example, polymers, such as water soluble polymers, the constant domain of immunoglobulins; all or part of human serum albumin (HSA); fetuin A; fetuin B; a leucine zipper domain; a tetranectin trimerization domain; mannose binding protein (also known as mannose binding lectin), for example, mannose binding protein 1; and an Fc region, as described herein and further described in U.S. Pat. No. 6,686,179.

A CSF1R ECD fusion molecule of the invention may be prepared by attaching polyaminoacids or branch point amino acids to the CSF1R ECD. For example, the polyaminoacid may be a carrier protein that serves to increase the circulation half life of the CSF1R ECD (in addition to the advantages achieved via a fusion molecule). For the therapeutic purpose of the present invention, such polyaminoacids should ideally be those that have or do not create neutralizing antigenic response, or other adverse responses. Such polyaminoacids may be chosen from serum album (such as HSA), an additional antibody or portion thereof, for example the Fc region, fetuin A, fetuin B, leucine zipper nuclear factor erythroid derivative-2 (NFE2), neuroretinal leucine zipper, tetranectin, or other polyaminoacids, for example, lysines. As described herein, the location of attachment of the polyaminoacid may be at the N terminus or C terminus, or other places in between, and also may be connected by a chemical linker moiety to the selected molecule.

Polymers

Polymers, for example, water soluble polymers, are useful in the present invention as the CSF1R ECD to which the polymer is attached will not precipitate in an aqueous environment, such as typically found in a physiological environment. Polymers employed in the invention will be pharmaceutically acceptable for the preparation of a therapeutic product or composition.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3,6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyalkylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

Polymers used herein, for example water soluble polymers, may be of any molecular weight and may be branched or unbranched. In certain embodiments, the polymers each typically have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a CSF1R ECD of the invention.

Polymers employed in the present invention are typically attached to a CSF1R ECD with consideration of effects on functional or antigenic domains of the polypeptide. In general, chemical derivatization may be performed under any suitable condition used to react a protein with an activated polymer molecule. Activating groups which can be used to link the polymer to the active moieties include sulfone, maleimide, sulfhydryl, thiol, triflate, tresylate, azidirine, oxirane, and 5-pyridyl.

Polymers of the invention are typically attached to a heterologous polypeptide at the alpha (α) or epsilon (ε) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to a CSF1R ECD via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting a CSF1R ECD with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-, tri-, etc.), the molecular weight of the polymer selected, whether the polymer is branched or unbranched and the reaction conditions used. The ratio of polymer (for example, PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified CSF1R ECD. One may select a polymer by molecular weight, branching, etc., the proportion of polymers to CSF1R ECD molecules in the reaction mix, the type of reaction to be performed, and the method of obtaining the selected N-terminal chemically modified CSF1R ECD. The method of obtaining the N-terminal chemically modified CSF1R ECD preparation (separating this moiety from other monoderivatized moieties if necessary) may be by purification of the N-terminal chemically modified CSF1R ECD material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N terminus with a carbonyl group-containing polymer is achieved. For example, one may selectively attach a polymer to the N terminus of the protein by performing the reaction at a pH that allows one to take advantage of the pKa differences between the ε-amino group of the lysine residues and that of the α-amino group of the N-terminal residue of the protein. By such selective derivatization, attachment of a polymer to a protein is controlled: the conjugation with the polymer takes place predominantly at the N terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized CSF1R ECD to include mono- or poly- (e.g., 2-4) PEG moieties. Pegylation may be carried out by any of the pegylation reactions available. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions will be determined case by case based on known parameters and the desired result.

There are a number of PEG attachment methods available to those skilled in the art. See, for example, EP 0 401 384; Malik et al., *Exp. Hematol.,* 20:1028-1035 (1992); Francis, *Focus on Growth Factors,* 3(2):4-10 (1992); EP 0 154 316; EP 0 401 384; WO 92/16221; WO 95/34326; and the other publications cited herein that relate to pegylation.

The step of pegylation as described herein may be carried out via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (for example, those containing 2-6 or 2-5 PEG groups). The PEG groups are generally attached to the protein at the α- or ε-amino groups of amino acids, but it is also contemplated that the PEG groups could be attached to any amino group attached to the protein that is sufficiently reactive to become attached to a PEG group under suitable reaction conditions.

Pegylation by acylation generally involves reacting an active ester derivative of polyethylene glycol (PEG) with a CSF1R ECD of the invention. For acylation reactions, the polymer(s) selected typically have a single reactive ester group. Any known or subsequently discovered reactive PEG molecule may be used to carry out the pegylation reaction. An example of a suitable activated PEG ester is PEG esterified to N-hydroxysuccinimide (NHS). As used herein, acylation is contemplated to include, without limitation, the following types of linkages between the therapeutic protein and a polymer such as PEG: amide, carbamate, urethane, and the like, see for example, Chamow, *Bioconjugate Chem.,* 5:133-140 (1994). Reaction conditions may be selected from any of those currently known or those subsequently developed, but should avoid conditions such as temperature, solvent, and pH that would inactivate the polypeptide to be modified.

Pegylation by acylation will generally result in a poly-pegylated protein. The connecting linkage may be an amide. The resulting product may be substantially only (e.g., >95%) mono-, di-, or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography, and electrophoresis.

Pegylation by alkylation generally involves reacting a terminal aldehyde derivative of PEG with a polypeptide in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1-C10 alkoxy or aryloxy derivatives thereof, see for example, U.S. Pat. No. 5,252,714.

Markers

Moreover, CSF1R ECDs of the present invention may be fused to marker sequences, such as a peptide that facilitates purification of the fused polypeptide. The marker amino acid sequence may be a hexa-histidine peptide such as the tag provided in a pQE vector (Qiagen, Mississauga, Ontario, Canada), among others, many of which are commercially available. As described in Gentz et al., *Proc. Natl. Acad. Sci.* 86:821-824 (1989), for instance, hexa-histidine provides for convenient purification of the fusion protein. Another peptide tag useful for purification, the hemagglutinin (HA) tag, corresponds to an epitope derived from the influenza HA protein. (Wilson et al., *Cell* 37:767 (1984)). Any of these above fusions may be engineered using the CSF1R ECDs of the present invention.

Oligomerization Domain Fusion Partners

In various embodiments, oligomerization offers certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains; and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that may be used as fusion partners are known in the art. In certain embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Certain additional Fc fusion partners include, but are not limited to, human IgA and IgM. In certain embodiments, an Fc fusion partner comprises a C237S mutation. In certain embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs.:19 to 21.

Albumin Fusion Partners and Albumin-binding Molecule Fusion Partners

In certain embodiments, a fusion partner is an albumin. Certain exemplary albumins include, but are not limited to, human serum album (HSA) and fragments of HSA that are capable of increasing the serum half-life or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

Exemplary Attachment of Fusion Partners

The fusion partner may be attached, either covalently or non-covalently, to the N terminus or the C terminus of the CSF1R ECD. The attachment may also occur at a location within the CSF1R ECD other than the N terminus or the C terminus, for example, through an amino acid side chain (such as, for example, the side chain of cysteine, lysine, serine, or threonine).

In either covalent or non-covalent attachment embodiments, a linker may be included between the fusion partner and the CSF1R ECD. Such linkers may be comprised of at least one amino acid or chemical moiety. Exemplary methods of covalently attaching a fusion partner to a CSF1R ECD include, but are not limited to, translation of the fusion partner and the CSF1R ECD as a single amino acid sequence and chemical attachment of the fusion partner to the CSF1R ECD. When the fusion partner and a CSF1R ECD are translated as single amino acid sequence, additional amino acids may be included between the fusion partner and the CSF1R ECD as a linker. In certain embodiments, the linker is glycine-serine ("GS"). In certain embodiments, the linker is selected based on the polynucleotide sequence that encodes it, to facilitate cloning the fusion partner and/or CSF1R ECD into a single expression construct (for example, a polynucleotide containing a particular restriction site may be placed between the polynucleotide encoding the fusion partner and the polynucleotide encoding the CSF1R ECD, wherein the polynucleotide containing the restriction site encodes a short amino acid linker sequence). When the fusion partner and the CSF1R ECD are covalently coupled by chemical means, linkers of various sizes may typically be included during the coupling reaction.

Exemplary methods of non-covalently attaching a fusion partner to a CSF1R ECD include, but are not limited to, attachment through a binding pair. Exemplary binding pairs include, but are not limited to, biotin and avidin or streptavidin, an antibody and its antigen, etc.

In embodiments wherein the FGFR1 ECD sequence comprises SEQ ID NO:2 (i.e. amino acids 1-506 of the human full length FGFR1 ECD), the FGFR1 ECD fusion molecule amino acid sequence excludes the last six C-terminal residues of SEQ ID NO:1 (the full length amino acid sequence of residues 1-512). This phrase means that any additional amino acid residues that immediately follow the C-terminal amino acid residue of SEQ ID NO:2, such as from a polypeptide fusion partner or peptide linker, do not begin with the amino acid sequence of 507-512 of the human FGFR1 ECD, which is THPPDE. Although, of course, the amino acid sequence THPPDE may appear elsewhere in the amino acid sequence of the inventive proteins.

Signal Peptide

In order for some secreted proteins to express and secrete in large quantities, a signal peptide from a heterologous protein may be desirable. Employing heterologous signal peptides may be advantageous in that a resulting mature polypeptide may remain unaltered as the signal peptide is removed in the ER during the secretion process. The addition of a heterologous signal peptide may be required to express and secrete some proteins.

Certain exemplary signal peptide sequences are described, e.g., in the online Signal Peptide Database maintained by the Department of Biochemistry, National University of Singapore. See Choo et al., *BMC Bioinformatics,* 6: 249 (2005); and PCT Publication No. WO 2006/081430.

Co-Translational and Post-Translational Modifications

The invention encompasses CSF1R ECDs and CSF1R ECD fusion molecules that are differentially modified during or after translation, for example by glycosylation, acetylation, phosphorylation, amidation, derivatization by known protecting/blocking groups, proteolytic cleavage, or linkage to an antibody molecule or other cellular ligand. Any of numerous chemical modifications may be carried out by known techniques, including, but not limited to, specific chemical cleavage by cyanogen bromide, trypsin, chymotrypsin, papain, V8 protease; $NABH_4$; acetylation; formylation; oxidation; reduction; and/or metabolic synthesis in the presence of tunicamycin.

Additional post-translational modifications encompassed by the invention include, for example, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression Nucleic Acid Molecules Encoding CSF1R ECDs and Nucleic Acid Molecules Encoding CSF1R ECD Fusion Molecules Nucleic acid molecules comprising polynucleotides that encode CSF1R ECDs or CSF1R ECD fusion molecules are provided. Nucleic acid molecules comprising polynucleotides that encode CSF1R ECD fusion molecules in which the CSF1R ECD and the fusion partner are translated as a single polypeptide are also provided. Such nucleic acid molecules may be constructed using recombinant DNA techniques conventional in the art.

In certain embodiments, a polynucleotide encoding a CSF1R ECD comprises a nucleotide sequence that encodes a signal peptide, which, when translated, will be fused to the N terminus of the CSF1R ECD. As discussed above, the signal peptide may be the native CSF1R signal peptide, or may be another heterologous signal peptide. In certain embodiments, the nucleic acid molecule comprising the polynucleotide encoding the gene of interest is an expression vector that is suitable for expression in a selected host cell.

CSF1R ECD and CSF1R ECD Fusion Molecule Expression and Production

Vectors

Vectors comprising polynucleotides that encode CSF1R ECDs are provided. Vectors comprising polynucleotides that encode CSF1R ECD fusion molecules are also provided.

Such vectors include, but are not limited to, DNA vectors, phage vectors, viral vectors, retroviral vectors, etc.

In certain embodiments, a vector is selected that is optimized for expression of polypeptides in CHO or CHO-derived cells. Exemplary such vectors are described, e.g., in Running Deer et al., *Biotechnol. Prog.* 20:880-889 (2004).

In certain embodiments, a vector is chosen for in vivo expression of CSF1R ECDs and/or CSF1R ECD fusion molecules in animals, including humans. In certain such embodiments, expression of the polypeptide is under the control of a promoter that functions in a tissue-specific manner. For example, liver-specific promoters are described, e.g., in PCT Publication No. WO 2006/076288.

Host Cells

In various embodiments, CSF1R ECDs or CSF1R ECD fusion molecules may be expressed in prokaryotic cells, such as bacterial cells; or in eukaryotic cells, such as fungal cells, plant cells, insect cells, and mammalian cells. Such expression may be carried out, for example, according to procedures known in the art. Certain exemplary eukaryotic cells that may be used to express polypeptides include, but are not limited to, COS cells, including COS 7 cells; 293 cells, including 293-6E cells; CHO cells, including CHO—S and DG44 cells; and NSO cells. In certain embodiments, a particular eukaryotic host cell is selected based on its ability to make certain desired post-translational modifications to the CSF1R ECDs or CSF1R ECD fusion molecules. For example, in certain embodiments, CHO cells produce CSF1R ECD fusion molecules that have a higher level of sialylation than the same polypeptide produced in 293 cells.

Introduction of a nucleic acid into a desired host cell may be accomplished by any method known in the art, including but not limited to, calcium phosphate transfection, DEAE-dextran mediated transfection, cationic lipid-mediated transfection, electroporation, transduction, infection, etc. Certain exemplary methods are described, e.g., in Sambrook et al., *Molecular Cloning, A Laboratory Manual,* 3rd ed. Cold Spring Harbor Laboratory Press (2001). Nucleic acids may be transiently or stably transfected in the desired host cells, according to methods known in the art.

In certain embodiments, a polypeptide may be produced in vivo in an animal that has been engineered or transfected with a nucleic acid molecule encoding the polypeptide, according to methods known in the art.

Purification of CSF1R ECD Polypeptides

CSF1R ECDs or CSF1R ECD fusion molecules may be purified by various methods known in the art. Such methods include, but are not limited to, the use of affinity matrices or hydrophobic interaction chromatography. Suitable affinity ligands include any ligands of the CSF1R ECD or of the fusion partner, or antibodies thereto. For example, a Protein A, Protein G, Protein A/G, or an antibody affinity column may be used to bind to an Fc fusion partner to purify a CSF1R ECD fusion molecule. Antibodies to CSF1R ECD may also be used to purify CSF1R ECD or CSF1R ECD fusion molecules. Hydrophobic interactive chromatography, for example, a butyl or phenyl column, may also suitable for purifying certain polypeptides. Many methods of purifying polypeptides are known in the art.

Therapeutic Compositions and Methods

Methods of Treating Diseases Using CSF1R ECD Fusion Molecules

The invention comprises methods of treating RA and MS to patients who have and/or have been diagnosed with MS or RA conditions. The invention also comprises methods for depleting peripheral blood monocytes in patients.

Certain embodiments of the invention, such as, for example, a CSF1R ECD fusion protein wherein the CSF1R ECD comprises SEQ ID NO:2 and excludes the last six C-terminal residues of the full length human ECD sequence of SEQ ID NO:1, a CSF1R ECD fusion protein wherein the CSF1R ECD consists of SEQ ID NO:2, or a fusion protein comprising or consisting of SEQ ID NO:6, may be useful in treating other inflammatory conditions, such as psoriasis, SLE (lupus), COPD, atopic dermatitis, and atherosclerosis, as well as macrophage activation syndrome and histiocytosis X.

Certain embodiments, such as, for example, a CSF1R ECD fusion protein wherein the CSF1R ECD comprises SEQ ID NO:2 but excludes the last six C-terminal residues of the full length human ECD sequence of SEQ ID NO:1, a CSF1R ECD fusion protein wherein the CSF1R ECD consists of SEQ ID NO:2, or a fusion protein comprising or consisting of SEQ ID NO:6, may also be useful in treating other inflammatory conditions including: proliferative vascular disease, acute respiratory distress syndrome, cytokine-mediated toxicity, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, bums, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type I diabetes, type 2 diabetes, Berger's disease, Retier's syndrome, and Hodgkins disease, or in treating inflammation associated with these conditions.

Routes of Administration and Carriers

In a particular embodiment, the CSF1R ECD fusion molecule is administered subcutaneously. In another particular embodiment, the CSF1R ECD fusion molecule is administered intravenously. In certain other embodiments, the CSF1R ECD fusion molecules may be administered in vivo by various routes, including, but not limited to, oral, intra-arterial, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding a CSF1R ECD and/or a CSF1R ECD fusion molecule may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising CSF1R ECDs or CSF1R ECD fusion molecules are provided in formulations with a wide variety of pharmaceutically acceptable carriers (see, e.g., Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems,* $7^{th}$ ed., Lippencott Williams and Wilkins (2004); Kibbe et al., *Handbook of Pharmaceutical Excipients,* $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

In various embodiments, compositions comprising CSF1R ECDs or CSF1R ECD fusion molecules may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of a CSF1R ECD and/or a CSF1R ECD fusion molecule are also provided. In certain embodiments, a unit dosage is provided wherein the unit dosage contains a predetermined amount of a composition comprising a CSF1R ECD and/or a CSF1R ECD fusion molecule, with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain embodiments, the composition comprises one or more substances that inhibit protein aggregation, including, but not limited to, sucrose and arginine. In certain embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, the CSF1R ECD fusion molecules of the invention may be administered in an amount in the range of about 10 ug/kg body weight to about 100 mg/kg body weight per dose. In certain embodiments, the CSF1R ECD fusion molecules of the invention may be administered in an amount in the range of about 50 ug/kg body weight to about 5 mg/kg body weight per dose. In certain other embodiments, the CSF1R ECD fusion molecules of the invention may be administered in an amount in the range of about 100 ug/kg body weight to about 10 mg/kg body weight per dose. Optionally, the CSF1R ECD fusion molecules of the invention may be administered in an amount in the range of about 100 ug/kg body weight to about 20 mg/kg body weight per dose. Further optionally, the CSF1R ECD fusion molecules of the invention may be administered in an amount in the range of about 0.5 mg/kg body weight to about 20 mg/kg body weight per dose.

The CSF1R ECDs or CSF1R ECD fusion molecule compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In certain embodiments, an effective dose of the CSF1R ECD or CSF1R ECD fusion molecule is administered to a subject one or more times. In various embodiments, an effective dose of the CSF1R ECD or CSF1R ECD fusion molecule is administered to the subject once a month, more than once a month, such as, for example, every two months or every three months. In other embodiments, an effective does of the CSF1R ECD or CSF1R ECD fusion molecule is administered less than once a month, such as, for example, every two weeks or every week. An effective dose of the CSF1R ECD or CSF1R ECD fusion molecule is administered to the subject at least once. In certain embodiments, the effective dose of the CSF1R ECD or CSF1R ECD fusion molecule may be administered multiple times, including for periods of at least a month, at least six months, or at least a year.

Combination Therapy

CSF1R ECD fusion molecules of the invention may be administered alone or with other modes of treatment. They may be provided before, substantially contemporaneous with, or after other modes of treatment, for example, surgery, chemotherapy, radiation therapy, or the administration of a biologic, such as a therapeutic antibody. For treatment of rheumatoid arthritis, CSF1R ECD fusion molecules may be administered with other therapeutic agents, for example, methotrexate, anti-TNF agents such as Remicade, Humira, Simponi, and Enbrel; glucocorticoids such as prednisone; Leflunomide; Azothioprine; JAK inhibitors such as CP 590690; SYK inhibitors such as R788; anti-IL-6 antibodies; anti-IL-6R antibodies; anti-CD-20 antibodies; anti-CD19 antibodies; anti-GM-CSF antibodies; and anti-GM-CSF-R antibodies. For treatment of multiple scelarosis, CSF1R ECD fusion molecules may be administered with other therapeutic agents, for example, interferon alpha; interferon beta; prednisone; anti-alpha4 integrin antibodies such as Tysabri; anti-CD20 antibodies such as Rituxan; FTY720 (Fingolimod); and Cladribine (Leustatin).

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Certain CSF1R-ECD-Fc Fusion Molecules

The cloning, expression, and purification of the CSF1R ECD fusion proteins are described. Clones of the CSF1R ECD fusion proteins were generated using PCR and conventional subcloning techniques. The GenBank accession numbers for the human CSF1R and mouse CSF1R genes and their encoded proteins are as follows: human CSF1R (NM_005221 and NP_005202) and mouse CSF1R (NM_001037859 and NP_001032948). For use in transient transfection of 293-6E cells, the hCSF1R.506, hCSF1R.512, mCSF1R.506, and mCSF1R.511 cDNAs are cloned into the EcoRI and BamHI sites of the multiple cloning site of the pTT5-J vector. The pTT5-J vector is a modified version of the pTT5 vector (provided by Yves Durocher, Biotechnology Research Institute, Montreal, Canada) that contains a cDNA encoding the Fc region of a human IgG1 protein (amino acid residues 233-464 of GenBank accession number AAH19337) in which the cysteine residue at position 237 is replaced with a serine residue (Fc C237S; SEQ ID NO.:19) inserted into the BamHI site of the multiple cloning site. This initial cloning step introduces a glycine-serine (GS) linker between the CSF1R and the Fc due to the nucleic acids introduced by the BamHI restriction enzyme site. The nucleotides encoding the GS linker may be subsequently removed using standard molecular biology techniques. The sequences of the resulting clones were verified, and the constructs (fused to the Fc alone (Fc) or to the GS linker followed by the Fc (GS-Fc)) were used for subcloning into other vectors.

For use in stable transfection of CHO cells, the hCSF1R.506-Fc and mCSF1R.506-Fc cDNAs were subcloned into the pDEF38 vector (ICOS Corporation, Bothell, Wash.). The hCSF1R.506-Fc/pTT5-J and mCSF1R.506-Fc/pTT5-J clones were used for subcloning into the pDEF38 vector using standard molecular biology techniques. The hCSF1R.506-Fc and mCSF1R.506 cDNAs were inserted into the XhoI and XbaI sites of the pDEF38 vector, and the sequences of the resulting clones were verified.

For experiments using minicircle DNA, the mCSF1R.506-GS-Fc and mCSF1R.511-GS-Fc cDNAs are subcloned into the p2xC31MasterSfi vector, which is a modified version of the pØC31.hFIX vector (Chen et al., *Human Gene Therapy* 16:126-131 (2005)) in which an SfiI site was introduced after the intron for the purpose of cloning. The mCSF1R.506-GS-Fc/pTT5-J and mCSF1R.511-GS-Fc/pTT5-J clones are used for subcloning into the p2xC31MasterSfi vector using standard molecular biology techniques. The mCSF1R.506-GS-Fc and mCSF1R.511-GS-Fc cDNAs are inserted into the SfiI site of the p2xC31MasterSfi vector, and the sequences of the resulting clones were verified.

The primary sequence and domain structure of the full-length human CSF1R extracellular domain, which consists of 512 amino acid residues, are shown in FIG. 1. The five IgG domains are denoted from N terminus to C terminus as IgG-1, IgG-2, IgG-3, IgG-4, and IgG-5. Two human CSF1R ECD clones were constructed and are fused to either an Fc alone or to a GS linker followed by an Fc at their C terminus: the full-length CSF1R ECD (hCSF1R.512-Fc or hCSF1R.512-GS-Fc, respectively) and a CSF1R ECD that excludes the last six C-terminal amino acid residues of the full-length human CSF1R ECD (referred to herein as hCSF1R.506-Fc or hCSF1R.506-GS-Fc). Two mouse CSF1R ECD clones were constructed and are fused to either an Fc alone or to a GS linker followed by an Fc at their C terminus: the full-length CSF1R ECD (mCSF1R.511-Fc or mCSF1R.511-GS-Fc) and a CSF1R ECD that excludes the last five C-terminal amino acid residues of the full-length mouse CSF1R ECD (referred to herein as mCSF1R.506-Fc or mCSF1R.506-GS-Fc). Table 1 lists the various CSF1R-ECD-Fc fusion proteins used in these examples with full protein names, SEQ ID NOs., brief descriptions, and short names.

TABLE 1

CSF1R-ECD-Fc Fusion Proteins

| Protein Name | SEQ ID NO. | Brief Description | Short name |
| --- | --- | --- | --- |
| hCSF1R-ECD.512-Fc | 5 | Full-length human CSF1R ECD fused to an Fc | hCSF1R.512-Fc or h512 |
| hCSF1R-ECD.506-Fc | 6 | Human CSF1R ECD lacking the six C-terminal residues fused to an Fc | hCSF1R.506-Fc or h506 |
| mCSF1R-ECD.511-Fc | 7 | Full-length mouse CSF1R ECD fused to an Fc | mCSF1R.511-Fc or m511 |
| mCSF1R-ECD.506-Fc | 8 | Mouse CSF1R ECD lacking the five C-terminal residues fused to an Fc | mCSF1R.506-Fc or m506 |
| hCSF1R-ECD.512-GS-Fc | 31 | Full-length human CSF1R ECD fused to GS-Fc | hCSF1R.512-GS-Fc |
| hCSF1R-ECD.506-GS-Fc | 32 | Human CSF1R ECD lacking the six C-terminal residues fused to GS-Fc | hCSF1R.506-GS-Fc |
| mCSF1R-ECD.511-GS-Fc | 33 | Full-length mouse CSF1R ECD fused to GS-Fc | mCSF1R.511-GS-Fc |
| mCSF1R-ECD.506-GS-Fc | 34 | Mouse CSF1R ECD lacking the five C-terminal residues fused to GS-Fc | mCSF1R.506-GS-Fc |

Example 2

Expression and Purification of CSF1R-ECD-Fc Fusion Proteins from 293-6E and CHO Host Cells In certain Examples herein, the fusion proteins were expressed in 293-6E or CHO cells. The hCSF1R.506-Fc/pTT5-J, hCSF1R.506-GS-Fc/pTT5-J, hCSF1R.512-Fc/pTT5-J, and hCSF1R.512-GS-Fc/pTT5-J plasmid constructs described in Example 1 were designed to provide transient expression in 293-6E host cells. The hCSF1R.506-Fc/pDEF38 and mCSF1R.506-Fc/pDEF38 plasmid constructs described in Example 1 were designed to provide stable expression in CHO cells (or its derivatives, such as DG44 cells (Invitrogen, Carlsbad, Calif.)).

Small scale production of CSF1R-ECD-Fc fusion proteins was achieved by transient transfection of 293-6E cells grown in polycarbonate Erlenmeyer flasks fitted with a vented screw cap, rotated on a table top shaker at 130 RPM, and grown in Freestyle medium (Invitrogen) at 37° C. in 5% $CO_2$ at cell densities ranging from $0.5 \times 10^6$ to $3 \times 10^6$ cells/ml. Typically, 50 ml of cell culture was grown in a 250 ml flask. One day before the transfection, the cells were diluted to $0.6 \times 10^6$ cells/ml in fresh Freestyle medium. On the day of transfection, the cells were in log phase ($0.8 \times 10^6$ to $1.5 \times 10^6$ cells/ml), and the cell density was adjusted to $1 \times 10^6$ cells/ml. The transfection mix was prepared by adding 2.5 ml sterile PBS to two 15 ml tubes; 50 ug of DNA was added to one tube, and 100 ul of PEI solution (sterile stock solution of 1 mg/ml polyethylenimine, linear, 25 kDa, pH 7.0 (Polysciences, Warrington, Wis.)) was added to the second tube; the contents of the two tubes were combined and allowed to incubate for 15 minutes at room temperature in order to form the transfection complex. The transfection complex was transferred to the 293-6E cell suspension culture, which was allowed to grow for 6-7 days at 37° C. in 5% $CO_2$. At 24 hours post-transfection, the supplement tryptone N1 (Catalog #19 553, OrganoTechnie S.A., (La Courneuve, France)) was added to 0.5% (v/v) to the cells to feed the cells and stimulate protein production. The tryptone N1 was made up as a 20% (w/v) stock solution in water, filter sterilized using a 0.2 um filter, and stored at 4° C. until use.

The 293-6E cultures expressing the CSF1R-ECD-Fc fusion proteins were harvested on either day 6 or 7 post-transfection when the cell viability was above 60%. The culture supernatant was clarified by centrifugation at 5,000×g at 4° C., and then loaded onto a 5 ml HiTrap Protein A HP column (GE Catalog #17-0403-01) that was equilibrated in Buffer A (0.5 M NaCl, 1×PBS). The column was washed using 10 column volumes of Buffer A, and the protein was eluted using a mix linear-step gradient over 15 column volumes of Buffer B (0.5 M NaCl, 0.1 M glycine, pH 2.7). The flow rate was 3 ml/min, and 1 ml fractions were collected into 100 ul of 1 M Tris buffer, pH 7.5, in a 96-well deep well block to neutralize the glycine. After purification, the fractions were pooled based on their purity (>95%) as determined by Coomassie staining of an SDS-PAGE gel, and their endotoxin level was determined (1-2 EU/mg). The CSF1R-ECD-Fc fusion protein was then dialyzed overnight in 1×PBS and filter sterilized.

Large scale production of CSF1R-ECD-Fc fusion proteins was achieved by stable transfection of CHO-derived DG44 cells, which are negative for dihydrofolate reductase (DHFR) expression. The expression vectors comprising hCSF1R.506-Fc/pDEF38 and mCSF1R.506-Fc/pDEF38 described in Example 1 were used for transfection of the DG44 cells for stable production of the hCSF1R.506-Fc and mCSF1R.506-Fc fusion proteins, respectively. In this process, untransfected DHFR-negative DG44 cells were cultured in CHO-CD serum-free medium (Irvine Scientific, Irvine, Calif.) supplemented with 8 mM L-Glutamine, 1× Hypoxanthine/Thymidine (HT; Invitrogen, Carlsbad, Calif.), and 18 ml/L of Pluronic-68 (Invitrogen, Carlsbad, Calif.). About 50 ug of plasmid DNA comprising hCSF1R.506-Fc/pDEF38 or mCSF1R.506-Fc/pDEF38 was first linearized by digestion with the PvuI restriction enzyme, ethanol precipitated, briefly air-dried, and subsequently resuspended in 400 ul of sterile, distilled water. Cultured DG44 host cells were seeded into a shaker flask at about $5 \times 10^5$ cells/ml the day before transfection, which reached about $1 \times 10^6$ cells/ml on the day of transfection. The cells were harvested, and about $1 \times 10^7$ cells per transfection were pelleted by centrifugation.

For transfection, each cell pellet was resuspended in 0.1 ml of Nucleofector V solution and transferred to an Amaxa Nucleofector cuvette (Amaxa, Cologne, Germany). About 5 ug of the resuspended linearized plasmid DNA was added and mixed with the suspended DG44 cells in the cuvette. The cells were then electroporated using an Amaxa Nucleofector Device II using program U-024. Electroporated cells were cultured in CHO-CD medium for two days and were then transferred into selective medium (CHO-CD serum free medium supplemented with 8 mM L-Glutamine, and 18 ml/L Pluronic-68). The selective medium was changed once every week. After about 12 days, 1 ug/ml R3 Long IGF-1 growth factor (Sigma, St. Louis, Mo.) was added to the medium and the culture was continued for another week until confluent. The supernatants from pools of stably transfected cell lines were assayed using a sandwich ELISA assay with an anti-Fc antibody to determine the protein titer. This transfection method generated an expression level of about 30 ug/ml of the hCSF1R.506-Fc and mCSF1R.506-Fc fusion proteins from the pools of stably transfected cells.

For stable cell line development, a total of one hundred 96-well plates and twenty-two 96-well plates, each seeded with a calculated density of three cells per well, were screened for hCSF1R.506-Fc and mCSF1R.506-Fc overexpression, respectively, using an anti-Fc antibody in an ELISA-based assay. Microscopic inspection of the top 500 hCSF1R.506-Fc-expressing wells showed that 250 of the wells had single colonies, which were expanded from 96-well plates to 6-well plates. Similarly, the top 24 mCSF1R.506-Fc-expressing wells were expanded from 96-well plates to 6-well plates. Titers were re-analyzed in a 6-well production model, and the top 48 hCSF1R.506-Fc clones and the top 12 mCSF1R.506-Fc clones were further expanded into T75 flasks in serum-free medium. Six of the hCSF1R.506-Fc clones were discarded due to a failure to grow during this process. Based on titer re-analysis, the top 25 hCSF1R.506-Fc clones and one mCSF1R.506-Fc clone were transferred into shaker flasks to begin the process of adapting the clones to suspension culture in CHO-CD medium. Titers were re-analyzed for the suspension cultures by seeding the cells at $0.5 \times 10^6$ cells/ml in 50 ml of culture medium in a 250 ml shaker flask. The cultures were fed on day 3 with 10% feeding medium (Irvine Scientific, Irvine, Calif.), and the culture temperature was shifted to 32° C. on the same day. On day 12, the spent medium was harvested, and the hCSF1R.506-Fc and mCSF1R.506-Fc protein levels were determined by ELISA. One of the hCSF1R.506-Fc clones and the mCSF1R.506-Fc clone were selected for process development based on high production levels and sialic acid content, and a research cell bank was prepared for each clone. The hCSF1R.506-Fc clone had a titer of 250 mg/l, and the mCSF1R.506-Fc clone had a titer of 100 mg/l when grown in shaker flasks.

Following expression and secretion of CSF1R-ECD-Fc fusion proteins from DG44 cells, Protein A affinity chromatography and SP cation exchange chromatography were used to purify the fusion proteins. The Protein A step served as an enrichment step, and the cation exchange step was both a secondary purification step and an endotoxin removal step. The cell supernatant was substantially purified by initial capture using mAbSelect Protein A Sepharose (GE Healthcare

17-5199), which is an affinity matrix used to bind to the Fc. Prior to loading, the column was equilibrated with five column volumes of sterile buffer A (10 mM potassium phosphate, pH 7.0, 500 mM NaCl). The cell supernatant was applied at a linear velocity of 152.9 cm/h on an XK50 column with a bed dimension of 5 cm×5 cm. Bound CSF1R-ECD-Fc was then washed with five column volumes of sterile buffer A. Elution was then carried out by applying a step gradient of sterile buffer B (100 mM glycine, pH 2.7, 20 mM NaCl) at a linear velocity of 305.7 cm/h for five column volumes. Two 250 ml fractions were collected into tubes containing 25 ml of 1 M Tris, pH 8.0 (Cellgro #46-031-CM) to neutralize the eluate. All bound CSF1R-ECD-Fc was completely eluted by 2.5 column volumes as judged by the A280 chromatographic trace and by SDS-PAGE.

The Protein A column eluate comprising the CSF1R-ECD-Fc was then diluted 10-fold with buffer C (50 mM MES, pH 5.5) and subjected to further purification by SP Sepharose High Performance (GE Healthcare #17-1087) cation exchange chromatography that was packed into an XK50 column with 200 ml of resin with a bed dimension of 5 cm×10 cm. The Protein A material was applied at a linear velocity of 79.1 cm/h. The bound protein was washed with 10 column volumes of buffer D (20 mM MES, pH 5.5, 20 mM NaCl). A 20 column volume linear gradient was applied from 0% to 100% buffer F (20 mM MES, pH 5.5, 300 mM NaCl), followed by five column volumes of buffer F. Elution fractions were analyzed by SDS-PAGE, and the CSF1R-ECD-Fc-containing fractions were pooled.

Following the purification, endotoxin levels were determined by the limulus amoebocyte lysate (LAL) using the Endosafe PTS assay system (Charles River Laboratories). Endotoxin levels were typically below 0.1 EU/mg at this step. The highly purified material from the cation exchange column was then concentrated to the desired concentration and dialyzed against a 10-fold volume of 1×PBS with one change of buffer of 10-fold volume after more than 3 hours at 4° C. The dialyzed material was collected after an additional 20 hours of dialysis. The purified samples were aliquotted and flash frozen by liquid nitrogen for long-term storage at −80° C.

Example 3

Figure 2:
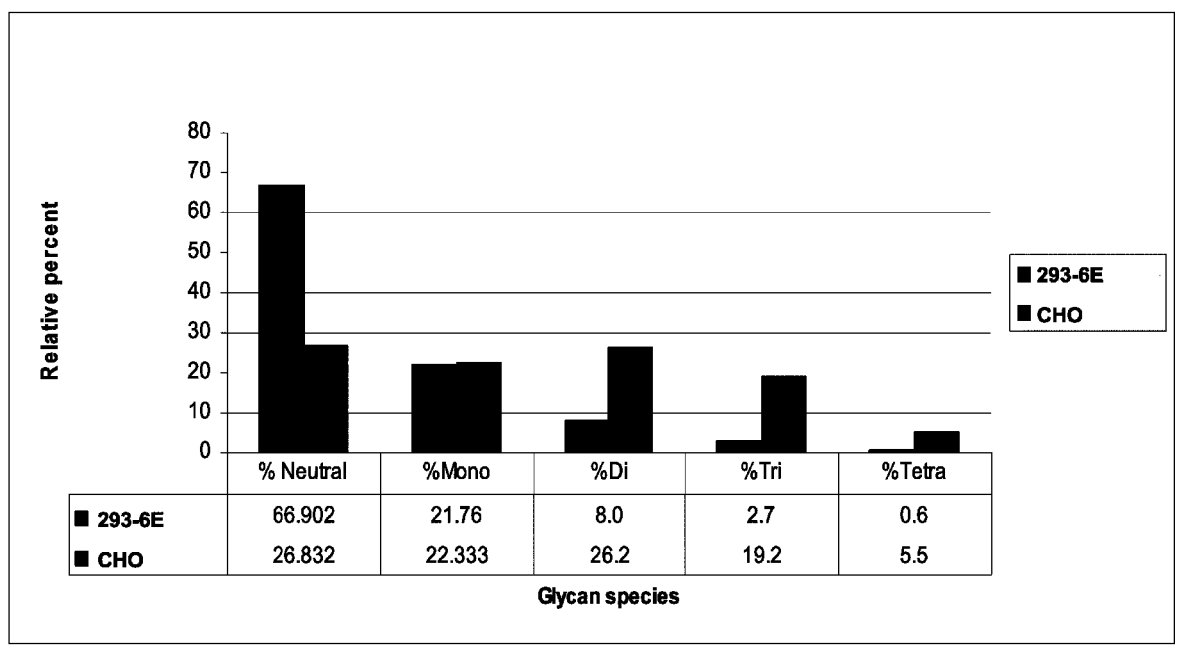
FIG. 2 shows the level of sialylation of the hCSF1R.506-Fc fusion protein produced in CHO host cells versus 293-6E host cells. Shown are the relative percentages of neutral, mono-, di-, tri-, and tetra-sialylation in CHO-and 293-6E-produced hCSF1R.506-Fc (corresponding values are shown in the table below the bar graph data).

Sialylation of the hCSF1R.506-Fc Fusion Protein in 293-63 Cells Versus CHO Cells Experiments were carried out to examine glycosylation and sialylation of the hCSF1R.506-Fc fusion protein expressed in 293-6E cells and in the CHO-derived DG44 cells. These experiments showed that the CHO-and 293-6E-produced CSF1R-ECD-Fc fusion proteins exhibited a similar overall level of glycosylation. However, the level of sialylation was higher in the CHO expression system relative to the 293-6E expression system. CHO-produced CSF1R-ECD-Fc fusion proteins exhibited a 10-fold higher level of tetra-sialylated glycans, a six-fold higher level of tri-sialylated glycans, a two-fold higher level of di-sialylated glycans, and a 2-fold reduction in the level of neutral glycans, which are involved in liver clearance. FIG. 2 shows the percentages of neutral, mono-, di-, tri-, and tetra-sialylation in CHO-and 293-6E-produced hCSF1R.506-Fc (corresponding values are shown below the graph).

Long-term storage of the purified CHO-produced fusion proteins at 4° C. (up to 5 weeks) showed little evidence of the laddering pattern observed with the 293-6E-produced fusion proteins. The CHO-produced CSF1R-ECD-Fc fusion protein has been concentrated to 90 mg/ml without any evidence of aggregation. Therefore, the increased level of sialylation associated with CHO-produced CSF1R-ECD-Fc fusion proteins leads to enhanced in vitro stability of the protein and also offers new routes of administration.

Example 4

CSF1R-ECD-Fc Fusion Proteins Bind to CSF1 and IL34

In order to determine whether the human CSF1R-ECD-Fc fusion proteins bind to the CSF1 and IL34 ligands, the hCSF1R.506-GS-Fc (SEQ ID NO.:32) and hCSF1R.512-GS-Fc (SEQ ID NO.:31) fusion proteins were expressed and purified from the culture media of 293-6E cells transiently transfected with the hCSF1R.506-GS-Fc/pTT5-J plasmid vector or the hCSF1R.512-GS-Fc/pTT5-J plasmid vector, respectively, as described in Example 2.

The CSF1 and IL34 ligand binding affinity and kinetics of the hCSF1R.506-GS-Fc and hCSF1R.512-GS-Fc fusion proteins were determined using Biacore® X surface plasmon resonance (SPR) technology (Uppsala, Sweden). CSF1 and IL34 are the only two ligands known to interact with the CSF1R ECD. The CSF1 and IL34 binding experiments were carried out using methodology similar to that described in Lin et al., *Science* 320:807-811, (2008).

The results of that experiment are shown in Tables 2 and 3.

TABLE 2

| IL34 Ligand Binding | | | |
|---|---|---|---|
| Protein Name | $k_a$ (1/Ms) | $k_d$ (1/s) | $K_D$ (M) |
| hCSF1R.512-GS-Fc | 1.19E+07 | 1.69E−05 | 1.42E−12 |
| hCSF1R.506-GS-Fc | 2.79E+07 | 1.90E−05 | 6.79E−13 |

TABLE 3

| CSF1 Ligand Binding | | | |
|---|---|---|---|
| Protein Name | $k_a$ (1/Ms) | $k_d$ (1/s) | $K_D$ (M) |
| hCSF1R.512-GS-Fc | 2.70E+07 | 1.30E−03 | 4.79E−11 |
| hCSF1R.506-GS-Fc | 4.62E+07 | 4.69E−04 | 1.02E−11 |

As shown in Tables 2 and 3, both the hCSF1R.512-GS-Fc and hCSF1R.506-GS-Fc fusion proteins bound to CSF1 and IL34, respectively, with high affinity. However, the hCSF1R.506-GS-Fc fusion protein had a 4-fold higher affinity for CSF1 and a 2-fold higher affinity for IL34 than the hCSF1R.512-GS-Fc fusion protein, as measured by the equilibrium dissociation constant ($K_D$). The results of these experiments are also summarized in FIG. 1.

These experiments demonstrated that the CSF1R ECD fusion proteins tested retained the ability to bind to both CSF1 and IL34. Surprisingly, the hCSF1R.506-GS-Fc fusion protein exhibited stronger binding than the hCSF1R.512-GS-Fc fusion protein to both CSF1 and IL34.

Example 5

CSF1R-ECD-Fc Fusion Proteins Inhibit Monocyte Viability

In order to determine whether the CSF1R-ECD-Fc fusion proteins are biologically active, their ability to inhibit human monocyte viability was examined. For these experiments, the hCSF1R.506-GS-Fc (SEQ ID NO.:32) and hCSF1R.512-GS-Fc (SEQ ID NO.:31) fusion proteins were expressed and purified from the culture media of 293-6E cells transiently transfected with the hCSF1R.506-GS-Fc/pTT5-J plasmid vector or the hCSF1R.512-GS-Fc/pTT5-J plasmid vector as described in Example 2.

Primary monocytes were isolated from human peripheral blood mononuclear cells (PBMC) through size sedimentation over Percoll columns as described (de Almeida et al., *Mem Inst Oswaldo Cruz* 95(2):221-223, (2000)). In this experiment, $1 \times 10^4$ freshly isolated human primary monocytes per well of a 96-well plate were incubated with the hCSF1R.506-GS-Fc or hCSF1R.512-GS-Fc fusion protein (0.01-120 nM) and the cells were incubated at 37° C. with 5% $CO_2$. After four days, ATP levels in the cells were determined using the CellTiter-Glo Luminescent Cell Viability Assay Kit (Promega, Cat. No. G7571), according to the manufacturer's instructions, as a measurement of cell viability.

Figure 3:
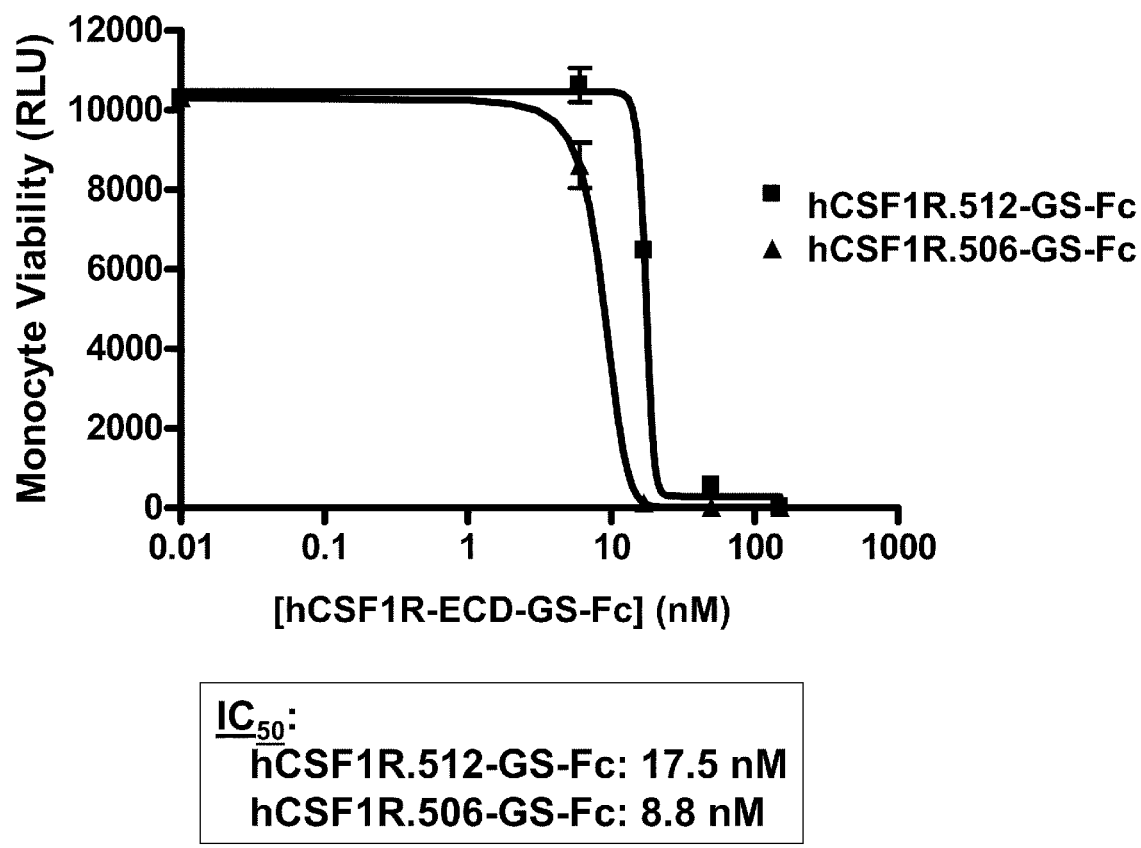
FIG. 3 shows the ability of the hCSF1R.512-GS-Fc and hCSF1R.506-GS-Fc fusion proteins to inhibit human monocyte viability and the corresponding $IC_{50}$ values.

As shown in FIG. 3, both the hCSF1R.512-GS-Fc and hCSF1R.506-GS-Fc fusion proteins inhibited human monocyte viability. The $IC_{50}$ value for hCSF1R.512-GS-Fc fusion protein was 17.5 nM, and the $IC_{50}$ value for the hCSF1R.506-GS-Fc fusion protein was 8.8 nM. These data demonstrated that the hCSF1R.506-GS-Fc fusion protein had a 2-fold higher inhibitory activity than the hCSF1R.512-GS-Fc fusion protein.

These experiments demonstrated that the CSF1R ECD fusion proteins retained the ability to inhibit human monocyte viability. Notably, the hCSF1R.506-GS-Fc fusion protein exhibited a stronger inhibitory activity than the hCSF1R.512-GS-Fc fusion protein.

Example 6

CSF1R-ECD-Fc Fusion Protein Inhibits CSF1- and IL34-Stimulated Monocyte Proliferation The hCSF1R.506 ECD fusion protein was further examined for its ability to inhibit CSF1- and IL34-stimulated human monocyte proliferation. For these experiments, the hCSF1R.506-Fc fusion protein (SEQ ID NO.:6) was expressed and purified from the culture media of CHO cells stably transfected with the hCSF1R.506-Fc/pDEF38 plasmid vector as described in Example 2.

Primary monocytes were isolated from human peripheral blood mononuclear cells (PBMC) through size sedimentation over Percoll columns as described in Example 5. The experiment to examine inhibition of CSF1- and IL34-stimulated monocyte proliferation was carried out using methodology similar to that described in Lin et al., *Science* 320:807-811, (2008).

Figure 4:
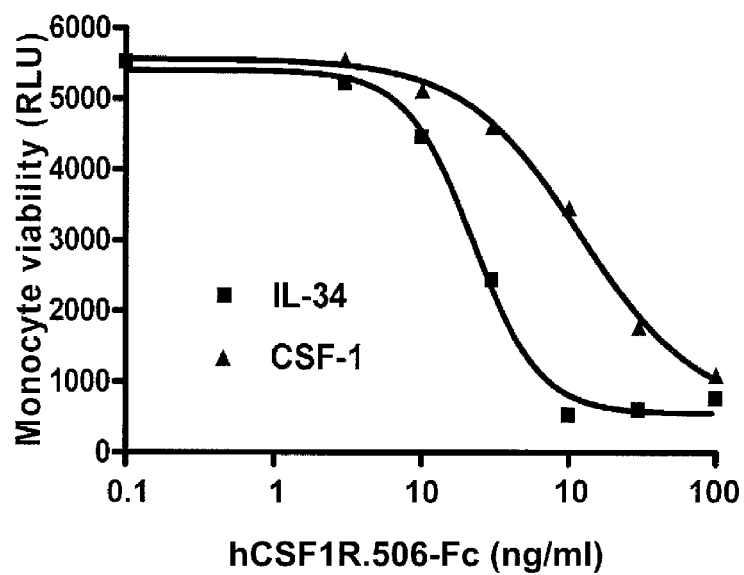
FIG. 4 shows the ability of the hCSF1R.506-Fc fusion protein to inhibit CSF1- and IL34-stimulated human monocyte proliferation.

The results of that experiment are shown in FIG. 4. As shown in FIG. 4, the hCSF1R.506-Fc fusion protein inhibited both CSF1- and IL34-stimulated proliferation of human monocytes. The $IC_{50}$ value for inhibition of IL34-induced monocyte proliferation was 0.27 nM, and the $IC_{50}$ value for inhibition of CSF1-induced monocyte proliferation was 1.5 nM. These experiments demonstrated that the hCSF1R.506-Fc fusion protein exhibited inhibitory activity against both CSF1- and IL34-stimulated human monocyte proliferation.

Example 7

CSF1R-ECD-Fc Fusion Protein Depletes Mouse Monocytes from Peripheral Blood

The mCSF1R.506-GS-Fc fusion protein (SEQ ID NO.:34) was expressed in vivo to determine whether it could deplete mouse monocytes from peripheral blood as a measure of in vivo biological activity. For these experiments, the minicircle DNA vector (mCSF1R.506-GS-Fc/p2xC31MasterSfi) containing the polynucleotides encoding mCSF1R.506-GS-Fc described in Example 1 was employed. For these experiments, 30 ug of CSF1R.506-GS-Fc-encoding minicircle DNA was injected into a C57BL/6 mouse tail vein by hydrodynamic tail vein transfection (TVT) as described (Ozaki et al., *J Immunol*, 173(9):5361-5371 (2004)). Saline was injected as a negative control. Approximately three weeks after the tail vein injection, peripheral blood cells were isolated and monocyte levels were determined using FACS analysis with anti-CD11b and anti-F4/80 antibodies according to the manufacturer's instruction (BD Biosciences) to detect monocyte marker-positive cells ($F4/80^+$, $CD11b^+$).

Figure 5:
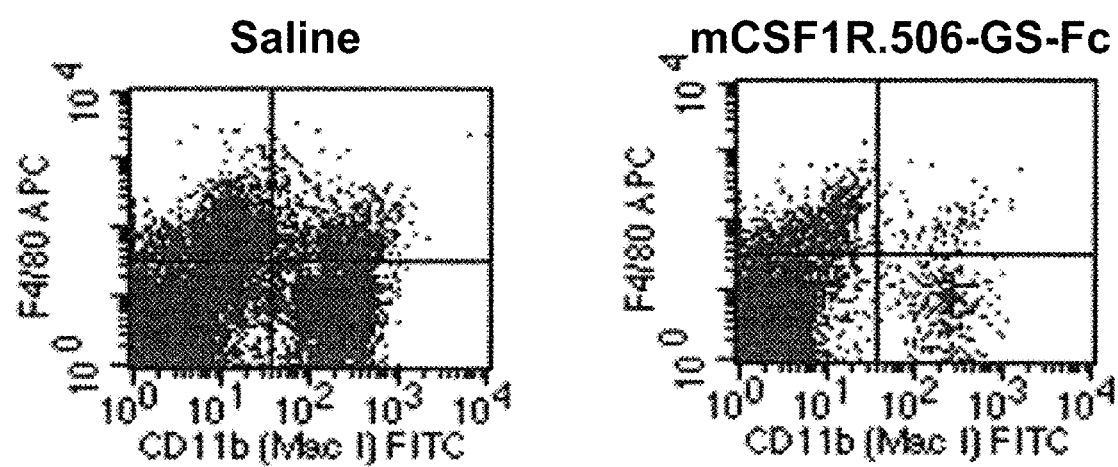
FIG. 5 shows the ability of the mCSF1R.506-GS-Fc fusion protein to deplete mouse monocytes from peripheral blood in vivo.

As shown in FIG. 5, in vivo expression of mCSF1R.506-GS-Fc led to a depletion of mouse monocytes from peripheral blood, as shown by a decrease in the number of monocyte marker-positive cells ($F4/80^+$, $CD11b^+$) in mice transfected with the mCSF1R.506-GS-Fc-encoding minicircle DNA. The results of this experiment demonstrated that the mCSF1R.506-GS-Fc fusion protein is biologically active in vivo.

Example 8

CSF1R-ECD-Fc Fusion Molecules Inhibit MS Disease Progression in the Mouse Experimental Autoimmune Encephalomyelitis (EAE) Model The CSF1R ECD fusion molecules were also tested for their ability to inhibit MS disease pathology in a mouse model of MS. These experiments used the mouse experimental autoimmune encephalomyelitis (EAE) model, which is widely used as a model of MS in humans. See, for example, Steinman and Zamvil, *TRENDS in Immunology*, 26(11):565-571 (2005). In the EAE model, disease progression and associated pathology may be measured according to the following EAE clinical score: no clinical disease (Score: 0); tail flaccidity (Score: 1); hind limb weakness (Score: 2); hind limb paralysis (Score: 3); forelimb paralysis or loss of ability to right from supine (stand up from a supine position) (Score: 4); and moribund (near death) or dead (Score: 5). EAE mice also exhibit a loss in body weight as the disease progresses. The mCSF1R.506-Fc fusion protein (m506) was tested to determine whether it could decrease the EAE clinical scores or body weight loss. The mCSF1R.506-Fc fusion protein (SEQ ID NO.:8) was expressed and purified from the culture media of CHO cells stably transfected with the mCSF1R.506-Fc/pDEF38 plasmid vector as described in Example 2.

For the EAE mouse model experiments, 60 female C57BL/6 mice, age 6-9 months, were divided into five groups:
  Group 1: Vehicle control (Vehicle) (phosphate buffered saline, PBS), 100 μl, i.p., 3 times a week for up to 7 weeks;
  Group 2: Methotrexate positive control (MTX), 10 mg/kg, i.v., q3d for up to 7 weeks;
  Group 3: mCSF1R.506-Fc, 1 mg/kg, i.p., 3 times a week for up to 7 weeks;
  Group 4: mCSF1R.506-Fc, 10 mg/kg, i.p., 3 times a week for up to 7 weeks;
  Group 5: mCSF1R.506-Fc, 20 mg/kg, i.p., 3 times a week for up to 7 weeks.

Each group consisted of 12 mice. EAE induction was performed according to the following protocol: 300 ug of myelin oligodendrocyte glycoprotein $(MOG)_{35-55}$ peptide was dissolved in 100 ul PBS and emulsified in an equal volume of complete Freund's adjuvant (CFA) containing 5 mg/ml *Mycobacterium tuberculosis* H37 RA. The emulsion (200 ul) was injected subcutaneously into the flank of the mice on days 0 and 7. Pertussis toxin (500 ng in 500 ul of PBS; List Biological Labs) was administered intravenously into each tail vein on days 0 and 2.

The MTX (10 mg/kg) was administered intravenously once every 3 days (q3d) for up to seven weeks starting on day 0; mCSF1R.506-Fc (1 mg/kg, 10 mg/kg, or 20 mg/kg), or vehicle (PBS) was administered intraperitoneally to the EAE mice in a 0.2 ml volume three times per week for 45 days, starting on day 0. The EAE clinical scores were measured prior to each dosing of PBS, MTX, or mCSF1R.506-Fc, using the above-mentioned scoring system. Body weights were recorded on day 0 before treatment was initiated, and were then measured at least twice per week including the day the study was terminated for seven weeks (on days 0, 2, 6, 8, 10, 13, 16, 17, 20, 22, 24, 27, 29, 31, 34, 36, 38, 41, 43, and 45).

Figure 6:
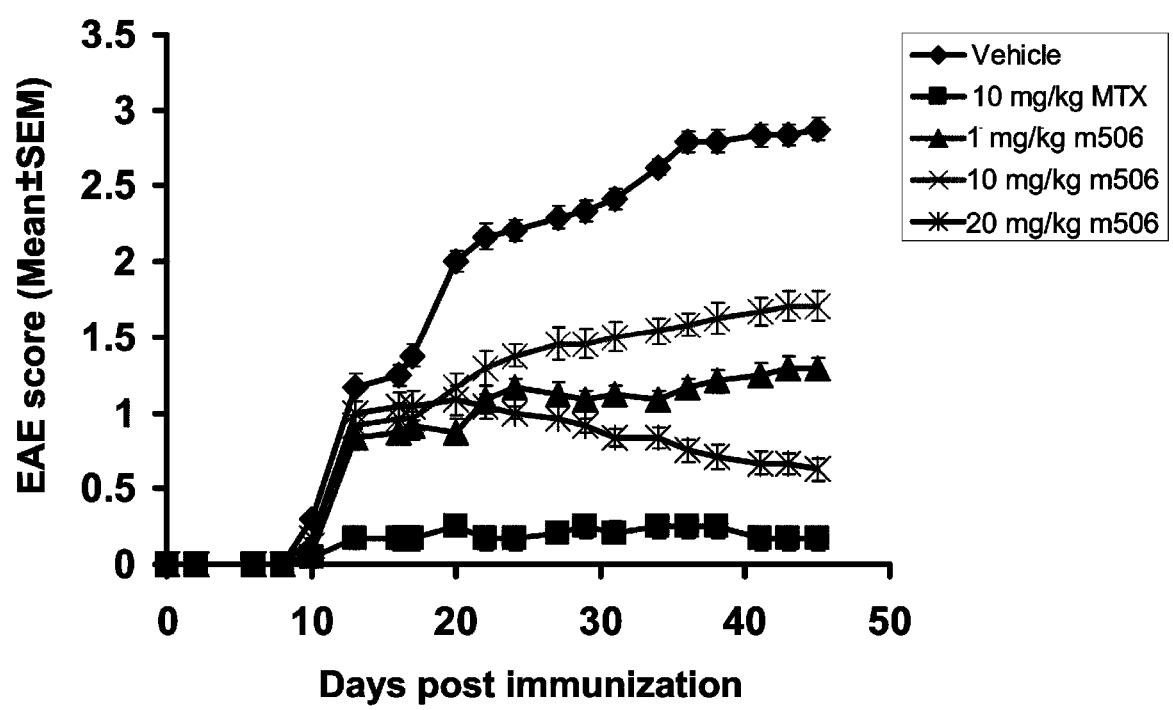
FIG. 6 shows the ability of the mCSF1R.506-Fc fusion protein (shown as m506) to inhibit MS disease progression in vivo in the experimental autoimmune encephalomyelitis (EAE) mouse model of MS.
Figure 7:
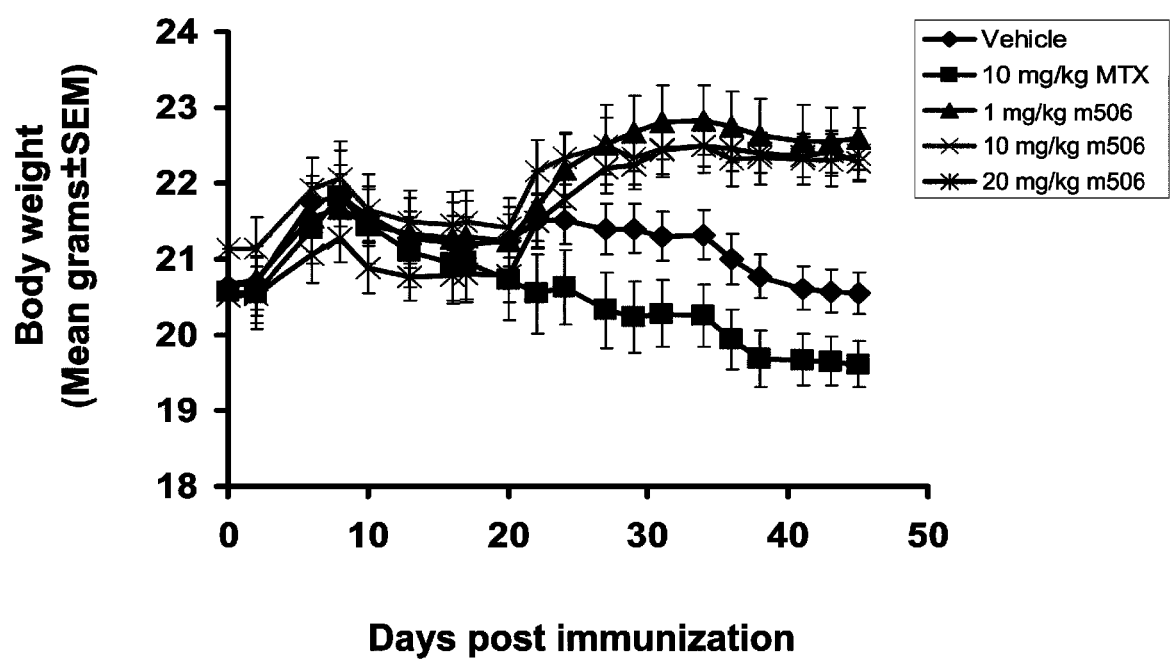
FIG. 7 shows the ability of the mCSF1R.506-Fc fusion protein (shown as m506) to protect against body weight loss in the EAE mouse model of MS.

The results are shown in FIGS. 6 and 7. As shown in FIG. 6, relative to the vehicle control, mCSF1R.506-Fc treatment reduced the EAE clinical score. The mCSF1R.506-Fc at 20 mg/kg was most effective with a 78% reduction in the EAE clinical score (Tukey test, $p<0.001$), and mCSF1R.506-Fc at 1 mg/kg and 10 mg/kg had intermediate effects with a 55% ($p<0.001$) and a 40% ($p<0.01$) reduction in the EAE score, respectively. The positive control, MTX, also inhibited the EAE clinical score with a 95% reduction in the EAE clinical score ($p<0.001$). In addition to the EAE clinical score, body weight loss is a non-subjective readout for disease progression and severity in the EAE model. As shown in FIG. 7, relative to the vehicle control, animals treated with the mCSF1R.506-Fc at three different doses had an average of 8% higher body weight (Tukey test, $p<0.01$~$0.001$). In contrast, MTX treatment, which is cytotoxic, led to a 4% ($p>0.05$) and 12% ($p<0.001$) decrease in body weight relative to the vehicle control and the mCSF1R.506-Fc treated animals, respectively.

These experiments demonstrated that mCSF1R.506-Fc treatment reduced the disease pathology characteristic of MS, including demyelination and body weight loss in the EAE mouse model of MS The results of these experiments also demonstrated that mCSF1R.506-Fc inhibited the progression of MS. Furthermore, mCSF1R.506-Fc treatment showed advantages over MTX, because mCSF1R.506-Fc treatment prevented body weight loss associated with the disease, whereas MTX treatment increased body weight loss. Thus, these experiments provide support that CSF1R ECD fusion molecules are effective treatments for MS.

Example 9

CSF1R-ECD-Fc Fusion Proteins Inhibit Disease Pathology in the Mouse Collagen-Induced Arthritis (CIA) Model The CSF1R ECD fusion proteins were also tested for their ability to inhibit disease pathology in a mouse model of RA. These experiments used the mouse collagen-induced arthritis (CIA) model, which is widely used as a model of RA in humans. See, for example, Hegen et al., *Ann Rheum Dis*, 67:1505-1515 (2008). In the CIA model, disease progression and associated pathology may be measured according to the following clinical arthritis scoring criteria for fore and hind paws: normal (Score: 0); one hind or fore paw joint affected, or minimal diffuse erythema and swelling (Score: 1); two hind or fore paw joints affected, or mild diffuse erythema and swelling (Score: 2); three hind or fore paw joints affected, or moderate diffuse erythema and swelling (Score: 3); marked diffuse erythema and swelling, or four digits affected (Score: 4); and severe diffuse erythema and severe swelling of entire paw, unable to flex digits (Score: 5). The mCSF1R.506-Fc fusion protein was tested to determine whether it could decrease the CIA-associated clinical arthritis score. The mCSF1R.506-Fc fusion protein (SEQ ID NO.:8) was expressed and purified from the culture media of CHO cells stably transfected with the mCSF1R.506-Fc/pDEF38 plasmid vector as described in Example 2.

For the CIA mouse model experiments, 59 male DBA/1 mice, which were at least 6 weeks old, were put into four different treatment groups:
  Group 1: Normal control;
  Group 2: Vehicle control (Vehicle) (phosphate buffered saline, PBS);
  Group 3: ENBREL® (10 mg/kg dose; provided by Bolder BioPath, Inc., as a 25 mg/ml stock solution purchased from Cornell Pharmacy and prepared as a 1 mg/ml solution in saline);
  Group 4: mCSF1R.506-Fc (m506) (20 mg/kg).
Group 1 (normal control) consisted of 4 mice, and Groups 2, 3, and 4 consisted of 15 mice each. Five mice were housed in each cage.

CIA mice (Groups 2-4) were anesthetized with isoflurane and given 150 ul of bovine type II collagen (Elastin Products) in Freund's complete adjuvant (with supplemental *Mycobacterium tuberculosis,* 4 mg/ml (Difco)) injections on day 0 and on day 21. Mice were randomized by body weight and put into treatment groups on study day 0. Vehicle and mCSF1R.506-Fc were administered intraperitoneally (i.p.) daily starting on day 0 and continued for 34 days. ENBREL® was delivered i.p. starting on study day 0 and continued twice weekly for 34 days. During the 34-day period, the clinical arthritis scores were determined for each of the paws (right front, left front, right rear, and left rear). In the CIA model, the onset of arthritis will occur on days 21-35. Mice were weighed on days 0, 7, 11, 14, 18, 20, 22, 24, 26, 28, 30, 32, and before tissue collection on day 34.

Figure 8:
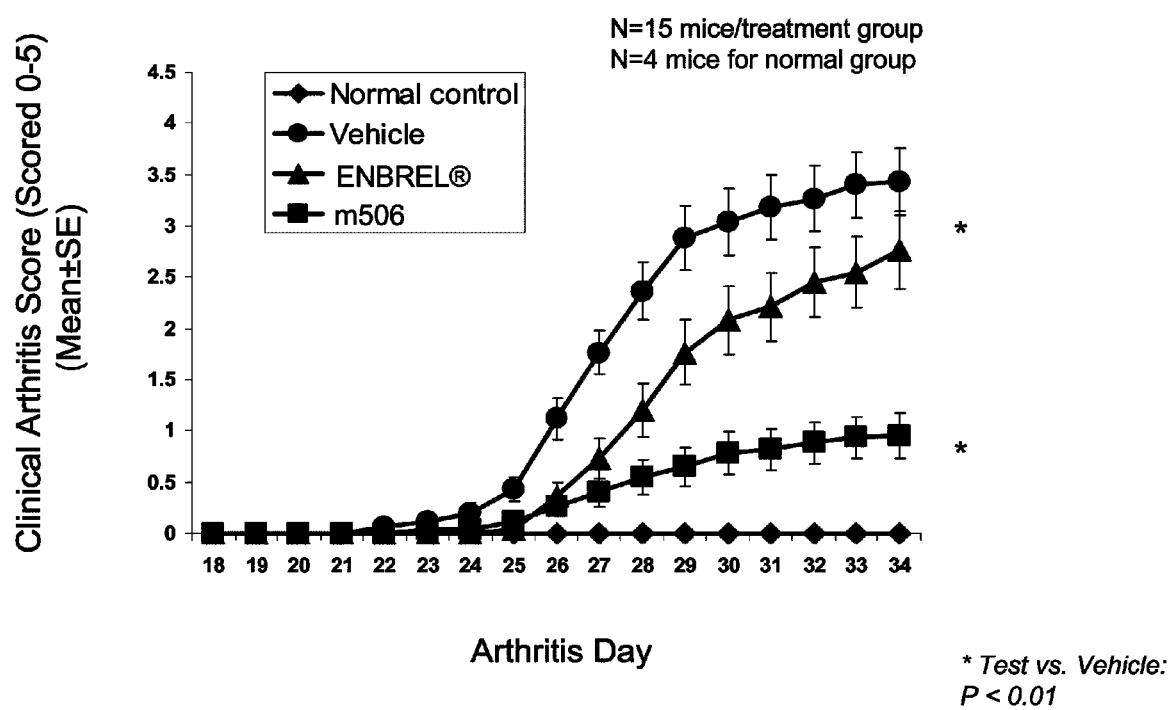
FIG. 8 shows the ability of the mCSF1R.506-Fc fusion protein (shown as m506) to inhibit arthritis symptoms in vivo in a mouse collagen-induced arthritis (CIA) model.

The results are shown in FIG. 8. As shown in FIG. 8, relative to the vehicle control, mCSF1R.506-Fc treatment significantly reduced the CIA arthritis score by about 75% (Tukey test, $p<0.01$). The positive control, ENBREL®, inhibited the CIA arthritis score by about 40% relative to the vehicle control (Tukey test, $p<0.01$).

These experiments demonstrated that mCSF1R.506-Fc treatment reduced the disease pathology, joint inflammation, and joint damage in the CIA mouse model. Thus, these experiments provide support that CSF1R ECD fusion molecules are an effective treatment for RA.

Example 10

Expression and Purification of Human hCSF1R.506 in CHO Host Cell Transient System Production of human CSF1R ECD amino acids 1-506 (hCSF1R.506; SEQ ID NO:2), was achieved by transient transfection of CHO-3E7 cells, which were grown in polycarbonate Erlenmeyer flasks fitted with a vented screw cap, rotated on a table top shaker at 130 RPM, and grown in Freestyle CHO (Invitrogen) at 37° C. in 5% $CO_2$ at cell densities ranging from $0.6 \times 10^6$ to $2 \times 10^6$ cells/ml. Typically, 600 ml of cell culture was grown in a 2 L flask with multiple flasks being prepared for one transfection. On the day of transfection, the cells were harvested by centrifugation, the media replaced with new media, and the cells resuspended at a cell density of 4×10⁶ cells/ml with 600 ml of cells per 2 L flask. DNA transfection complex was made by adding 900 ug of DNA into 22.5 ml of Freestyle CHO in one tube, and adding 4500 ug of PEI Max (sterile stock solution at 3 mg/ml polyethyleneinimine, 40 KD, pH7.0, (Polysciences Inc, 24765, Arrington, Wis.) in 22.5 ml of Freestyle CHO in a second tube. The contents of the two tubes were mixed and incubated for 8-10 minutes at room temperature in order to form the transfection complex. The transfection complex was transferred to the CHO-3E7 cell suspension culture, which was allowed to grow at 37° C. in 5% $CO_2$. At 24 hours post-transfection, the supplement tryptone N1 (Catalog #19 533, OrganoTechnie S.A., La Courneuve, France) was added at 1.0% (w/v) to the cells to feed the cells and stimulate protein production. Tryptone N1 was prepared as a 40% (w/v) stock solution in water, filter sterilized using a 0.2 um polyethersulfone filter, and stored at 4 C until use.

The CHO-3E7 cultures expressing the human CSF1R.506 protein were harvested on either day 6 or 7 post-transfection, before the cell viability dropped below 60%. The culture supernatant was centrifuged at 1400 rpm for 10 minutes and then 5,000×g for 10 minutes at 4° C. The supernatant was then dialyzed in 10 kD MWCO dialysis bags against Buffer A (10 mM Potassium Phosphate, pH 6.5, with 30 mM Sodium Chloride). The dialyzed material was loaded on a 5-ml SP Sepharose High Performance Cation Exchange column (GE Healthcare, 17-1152-01) ("SP column"). The SP column was washed with 5 column volumes of Buffer A. Bound protein was eluted from the column using a 25 column volume linear gradient elution from Buffer A to Buffer B (10 mM Potassium Phosphate, pH 6.5 with 0.5 M Sodium Chloride). Elution fractions were analyzed by SDS-PAGE and Western Blot using anti-human CSF1R antibody (R&D Systems, Inc.) to identify fractions containing human CSF1R.506.

Elution fractions from the SP column containing human CSF1R.506 were pooled and dialyzed in 10 KD MWCO dialysis bags against Buffer C (5 mM Potassium Phosphate, pH 6.5). The dialyzed material was loaded on a 7-ml hydroxyapatite (hydroxyapatite type I 20 um, BioRad 157-0020, Hercules, Calif.) column ("HA column"). The HA column was washed with 5 column volumes of Buffer C. Bound protein was eluted from the column using a 25 column volume linear gradient elution from Buffer C to Buffer D (400 mM Potassium Phosphate, pH 6.5 with 1 M Potassium Chloride). Elution fractions were analyzed by SDS-PAGE to identify fractions containing human CSF1R.506.

Elution fractions from the HA column containing human CSF1R.506 were pooled and the conductivity of the pool was determined. 2.4M ammonium sulfate was added to the CSF1R-ECD pool to match the conductivity of Buffer E (10 mM Tris, pH 8.0, with 1.2M Ammonium Sulfate). The adjusted protein pool was loaded on a 5-ml HiTrap Phenyl HP column (GE Healthcare, 17-5195-01). The column was washed with 5 column volumes Buffer E. Bound protein was eluted from the column using a 25 column volume linear gradient elution from Buffer E to Buffer F (10 mM Tris, pH 8.0). Elution fractions were analyzed by SDS-PAGE to identify fractions containing human CSF1R.506. Elusion fractions containing human CSF1R.506 were pooled, dialyzed against PBS, and then spin concentrated (10 kD MWCO, Amicon Ultra-15). The concentration of the Human CSF1R-ECD protein was determined by Bicinchoninic Acid assay (Pierce) using BSA as a protein standard.

Example 11

The hCSF1R.506 and hCSF1R.506-Fc Proteins Bind to CSF1

In order to compare the relative ligand binding affinity of hCSF1R.506 (SEQ ID NO:2) and hCSF1R.506-Fc (SEQ ID NO:6) proteins expressed in CHO cells to CSF1, a Biacore® assay was used. (See Example 4.) The results of the experiment are shown below.

TABLE 4

| Protein Name | $k_a$ (l/Ms) | $k_d$ (l/s) | $K_D$ (M) |
|---|---|---|---|
| hCSF1R.506-Fc | 1.35E+07 | 8.59E−04 | 6.38E−11 |
| hCSF1R.506 | 2.80E+04 | 8.09E−04 | 2.89E−08 |

Example 12

The hCSF1R.506-Fc Fusion Protein Inhibits CSF-1-Induced Monocyte Viability More Potently than hCSF1R.506

The abilities of hCSF1R.506-Fc fusion protein and hCSF1R.506, produced from CHO cells, to inhibit CSF-1-induced and IL-34-induced monocyte viability were compared. Primary monocytes were isolated from human peripheral blood mononuclear cells (PBMC) through size sedimentation over Percoll columns as described (de Almeida et al., *Mem inst Oswaldo Cruz* 95(2):221-223 (2000). In this experiment, 1×10 freshly isolated human primary monocytes per well in a 96-well plate were incubated with the hCSF1R.506-Fc fusion protein or hCSF-1R.506. After incubation for four days, ATP levels in the cells were determined using the CellTiter-Glo Luminescent Cell Viability Assay Kit (Promega, Cat. No. G7571), according to manufacturer's instructions, as a measurement of cell viability per manufacturer's instruction.

In the CSF-1-induced monocyte viability assay, the EC50 value for hCSF1R.506-Fc was 1.4 nM, and the EC50 value for hCSF1R.506 was greater than 100 nM. Similarly, hCSF1R.506-Fc inhibited IL-34-induced monocyte viability with an EC50 value of 0.65 nM while the EC50 value for hCSF1R.506 was greater than 50 nM. These data demonstrated that the hCSF1R.506-Fc fusion protein exhibited a greater potency than hCSF1R.506 in the inhibition of CSF-1-induced or IL-34-induced monocyte viability.

Example 13

The CSF1R-ECD.506-Fc Fusion Protein Inhibits Disease Pathology in the Mouse Collagen-Induced Arthritis Model The mCSF1R.506-Fc fusion proteins were further tested for their ability to inhibit disease pathology in the mouse CIA model of RA. The study used male DBA/1 mice, which were at least 7 weeks old at the start of the study. Animals were housed 5 per cage and put into different treatment groups.

Group 1: Naïve-Normal control;
Group 2: Vehicle control (Vehicle) (phosphate buffered saline, PBS);
Group 3: ENBREL® (10 mg/kg dose; purchased from Cornell Pharmacy and prepared as a 1 mg/ml solution in saline);

Group 4: mCSF1R.506-Fc (m506) (0.2 mg/kg, QD);
Group 5: mCSF1R.506-Fc (m506) (2 mg/kg, QD);
Group 6: mCSF1R.506-Fc (m506) (6 mg/kg, QD);
Group 7: mCSF1R.506-Fc (m506) (20 mg/kg, QD);
Group 8: mCSF1R.506-Fc (m506) (20 mg/kg, Q3D).

Group 1 (normal control) consisted of 4 mice, and Groups 2 to 8 consisted of 15 mice each. Five mice were housed in each cage.

CIA mice (Groups 2-8) were anesthetized with isoflurane and given 150 µl of bovine type II collagen (Elastin Products) in Freund's complete adjuvant (with supplemental *Mycobacterium tuberculosis*, 4 mg/ml (Difco)) injections on day 0 and on day 21. On study day 0, mice in groups 2 to 8 were randomized by body weight and put into treatment groups. For groups 2 to 7, vehicle or mCSF1R.506-Fc were administered intraperitoneally (i.p.) daily starting on day 0 and continued for 34 days. For group 8, mCSF1R.506-Fc was administered intraperitoneally (i.p.) every three days starting on day 0. ENBREL® was delivered i.p. daily starting on study day 0. During the 34-day period, the clinical arthritis scores were determined for each of the paws (right front, left front, right rear, and left rear). In the CIA model, the onset of arthritis will occur on days 21-35. Mice were weighed on days 0, 7, 11, 14, 18, 20, 22, 24, 26, 28, 30, 32, and before tissue collection on day 34.

In the CIA model, disease progression and associated pathology may be measured according to the following clinical arthritis scoring criteria for fore and hind paws: normal (Score: 0); one hind or fore paw joint affected, or minimal diffuse erythema and swelling (Score: 1); two hind or fore paw joints affected, or mild diffuse erythema and swelling (Score: 2); three hind or fore paw joints affected, or moderate diffuse erythema and swelling (Score: 3); marked diffuse erythema and swelling, or four digits affected (Score: 4); and severe diffuse erythema and severe swelling of entire paw, unable to flex digits (Score: 5).

Figure 9:
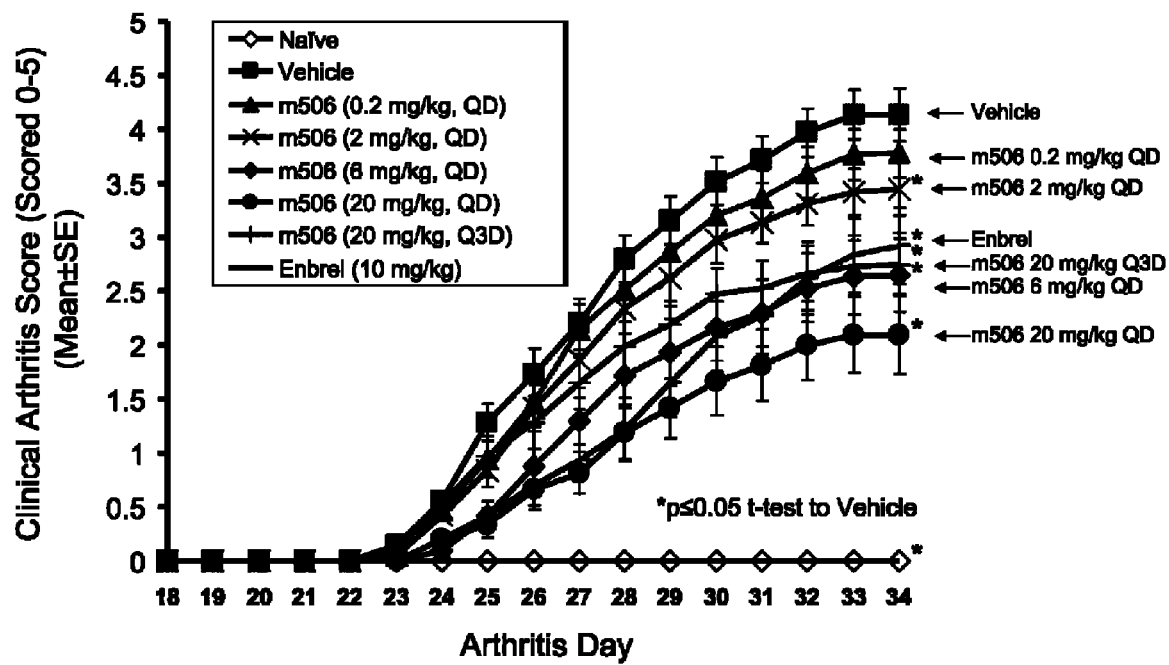
FIG. 9 shows the ability of the mCSF1R.506-Fc fusion protein (shown as m506) to ameliorate rheumatoid arthritis symptoms in vivo in a mouse collagen-induced arthritis (CIA) model.

The results of monitoring the clinical arthritis scoring criteria are shown in FIG. 9. As shown in FIG. 9, treatment with 2, 6, and 20 mg/kg mCSF1R.50-Fc fusion protein significantly reduced clinical arthritis scores, and the inhibition of clinical arthritis scores was dose-dependent. The positive control ENBREL® also inhibited clinical scores.

Joints were also processed to determine the effect of mCSF1R.50-Fc fusion protein treatment on inflammation, pannus formation, cartilage damage, and bone resorption. After joints were placed in fixative for 1-2 days and then in decalcifer for 4-5 days, the joints were processed, embedded, sectioned and stained with toluidine blue.

Figure 10:
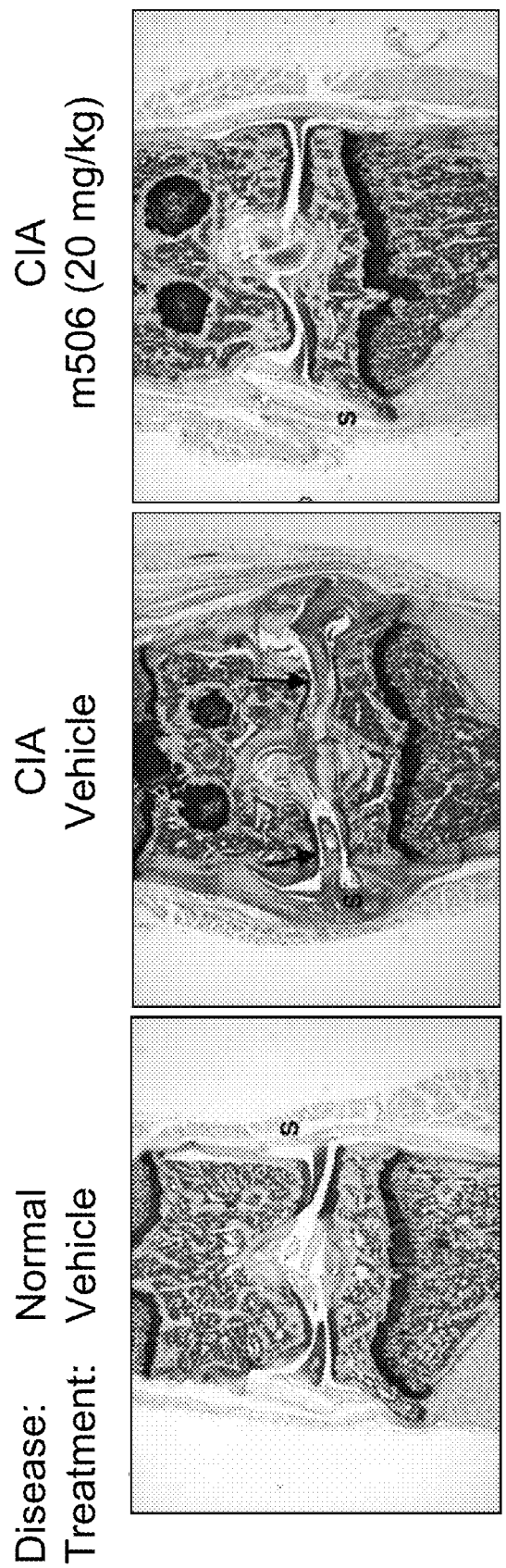
FIG. 10 shows the ability of mCSF1R.506-Fc fusion protein (shown as m506) to reduce pannus formation and joint destruction in a mouse CIA model.

FIG. 10 shows representative histologic sections from the joints of CIA mice. As shown in FIG. 10, treatment with mCSF1R.506-Fc fusion protein significantly decreased pannus formation, cartilage damage, and bone resorption in CIA mice.

The paws or ankles of mice were also scored to determine the effect of mCSF1R.50-Fc fusion protein treatment on inflammation, pannus formation, cartilage damage, and bone resorption. Scoring paws or ankles of mice with type II collagen arthritis lesions required consideration of the severity of changes to the joints and the number of individual joints affected. If only 1 to 3 joints of the paws or ankles were affected, an arbitrary assignment of a maximum score of 1, 2 or 3, depending on the severity of the changes to the joint, was given for each of the four parameters: inflammation, pannus formation, cartilage damage, and bone resorption. If more than 3 joints were involved, the following criteria were applied to the most severely affected/majority of joints.

Inflammation of the joints can be measured according to the following scoring criteria: normal (Score 0); minimal infiltration of inflammatory cells in synovium and periarticular tissue of affected joints (Score 1); mild infiltration of inflammatory cells, and if referring to paws, generally restricted to affected joints with 1-3 affected (Score 2); moderate infiltration with moderate edema, and if referring to paws, restricted to affected joints, generally 3-4 joints and wrist or ankle (Score 3); marked infiltration affecting most areas with marked edema, and 1 or 2 unaffected joints may be present (Score 4); and severe diffuse infiltration with severe edema affecting all joints and periarticular tissues (Score 5).

Pannus formation can be measured according to the following scoring criteria: normal (Score 0); minimal infiltration of pannus in cartilage and subchondral bone, marginal zones (Score 1); mild infiltration with marginal zone destruction of hard tissue in affected joints (Score 2); moderate infiltration with moderate hard tissue destruction in affected joints (Score 3); marked infiltration with marked destruction of joint architecture and affecting most joints (Score 4); and severe infiltration associated with total or near total destruction of joint architecture and affects all joints (Score 5).

Cartilage damage can be measured according to the following scoring criteria: normal (Score 0; normal); generally minimal to mild loss of toluidine blue staining with no obvious chondrocyte loss or collagen disruption in affected joints (Score 1; minimal); generally mild loss of toluidine blue staining with focal areas of chondrocyte loss and/or collagen disruption in some affected joints (Score 2; mild); generally moderate loss of toluidine blue staining with multifocal chondrocyte loss and/or collagen disruption in affected joints, some matrix remains on any affected surface with areas of severe matrix loss (Score 3; moderate); marked loss of toluidine blue staining with multifocal marked (depth to deep zone) chondrocyte loss and/or collagen disruption in most joints, if knee-one surface with total to near total cartilage loss (Score 4; marked); severe diffuse loss of toluidine blue staining with multifocal severe (depth to tide mark) chondrocyte loss and/or collagen disruption in all joints, if the knee is affected, 2 or more surfaces show total to near total cartilage loss (Score 5; severe).

Bone resorption can be measured according to the following scoring criteria: normal (Score 0); small areas of resorption, not readily apparent on low magnification, rare osteoclasts in affected joints, restricted to marginal zones (Score 1; minimal); more numerous areas of resorption, not readily apparent on low magnification, osteoclasts more numerous in affected joints, restricted to marginal zones (Score 2; mild); obvious resorption of medullary trabecular and cortical bone without full thickness defects in cortex, loss of some medullary trabeculae, lesion apparent on low magnification, osteoclasts more numerous in affected joints (Score 3; moderate); full thickness defects in cortical bone, often with distortion of profile of remaining cortical surface, marked loss of medullary bone, numerous osteoclasts, affects most joints (Score 4; marked); full thickness defects in cortical bone and destruction of joint architecture of all joints (Score 5; severe).

For each animal, inflammation, pannus formation, cartilage damage, and bone damage scores of 6 joints were determined. A sum total of the scores for all 6 joints (sum total animal score); a mean score for the six joints (six joint mean animal score) as well as sum and mean scores for each of the individual parameters were determined.

For statistical analyses, clinical data for paw scores (means for animal) were analyzed by determining the area under the dosing curve (AUC) for days 1-15. Clinical scoring criteria for fore and hind paws are as follows: normal (Score 0); 1 hind or fore paw joint affected or minimal diffuse erythema and swelling (Score 1); 2 hind or fore paw joints affected or mild diffuse erythema and swelling (Score 2); 3 hind or fore paw joints affected or moderate diffuse erythema and swelling (Score 3); marked diffuse erythema and swelling, or =4 digit joints affected (Score 4); severe diffuse erythema and severe swelling entire paw, unable to flex digits (Score 5). To calculate the AUC, the daily mean paw scores for each mouse were entered into Microsoft Excel and the area under the curve of daily mean paw scores from the onset of disease up to the termination day was computed. Means for each group were determined and the % inhibition from arthritis controls was calculated by comparing the values for treated and normal animals. Paw scores and histologic parameters (mean±SE) for each group were analyzed for differences using a Student's t test with significance set at $p \leq 0.05$.

Figure 11:
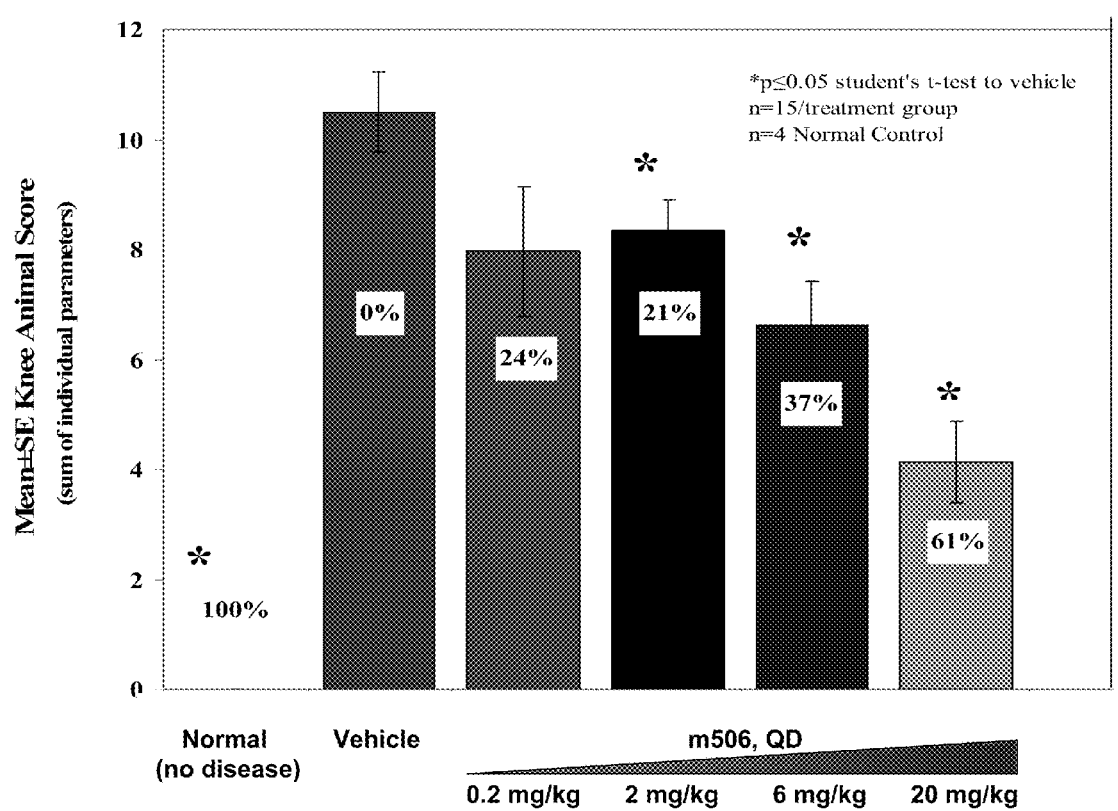
FIG. 11 shows the ability of mCSF1R.506-Fc fusion protein (shown as m506) to improve the inflammation, pannus, cartilage damage, and joint damage in the knee joint in a mouse CIA model.

The percent inhibition of histologic parameters and its associated AUC was calculated using the following formula: % Inhibition=A−B/A×100 where A=Mean Disease Control−Mean Normal and B=Mean Treated−Mean Normal FIG. 11 shows that treatment of with 2 mg/kg, 6 mg/kg, and 20 mg/kg of mCSF1R.506-Fc fusion protein significantly decreased inflammation, pannus formation, cartilage damage, and bone resorption compared to vehicle treated mice.

The ability of mCSF1R.506-Fc fusion protein to decrease serum pyridinoline (PYD) levels in CIA mice was also tested.

To assay PYD, mice were anesthetized and blood was collected by cardiac puncture. Serum samples were assayed to determine the levels of serum PYD, which is a degradation product of bone collagen and a biomarker for bone resorption. Serum PYD levels were assayed using the MicroVue Serum PYD ELISA kit (Quidel Corporation, San Diego, Calif., No. 8019) according to the manufacturer's instructions.

Figure 12:
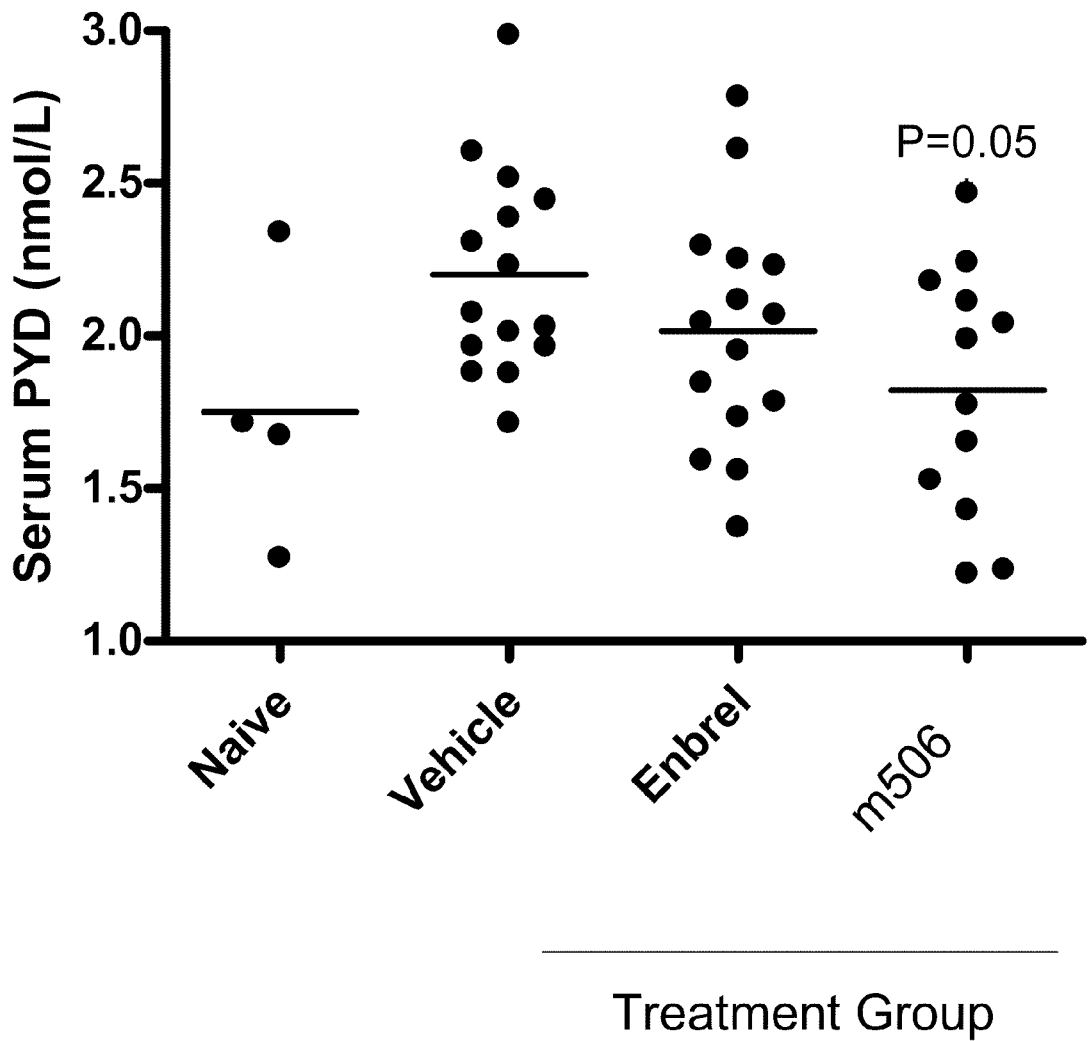
FIG. 12 shows the ability of mCSF1R.506-Fc fusion protein (shown as m506) to lower serum pyridinoline levels in a mouse CIA model.

The results are shown in FIG. 12. As shown in FIG. 12, the serum PYD levels in the CIA mice treated with mCSF1R.506-Fc fusion protein was significantly lower than in the CIA mice treated with vehicle control. These data show that mCSF1R.506-Fc fusion protein inhibited bone turnover as measured by serum PYD levels in a mouse CIA model. Reduction of PYD levels in the CIA mice treated with Enbrel was not significant statistically.

Example 14

Mouse CSF1R.506 Fusion Protein (mCSF1R.506-Fc) Depletes CD115$^+$ GR1$^-$ Monocytes from the Spleen Male DBA1 mice were administered i.p. 3 times per week with saline or mCSF1R.506-Fc protein (SEQ ID NO:34) at 20 mg/kg. After two weeks of treatment, spleens were harvested for analysis of monocytes by flow cytometry as described (Liu et al., *Science* 324: 392 (2009)). Cells were stained at 4° C. in PBS with 5% (vol/vol) FBS. An LSR II (Becton Dickinson) was used for multiparameter flow cytometry of stained cell suspensions, followed by analysis with FlowJo software (TreeStar).

Figure 13:
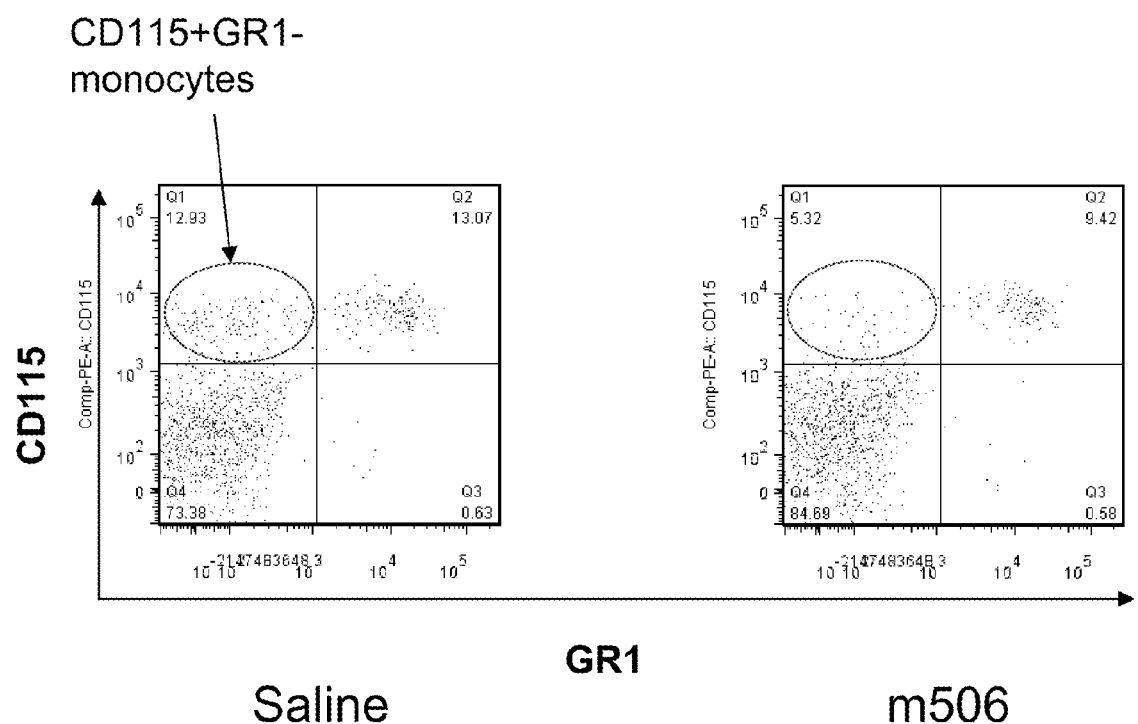
FIG. 13 shows the ability of mCSF1R.506-Fc fusion protein (shown as m506) to deplete CD115+ GR1− monocytes from spleen.
Figure 14:
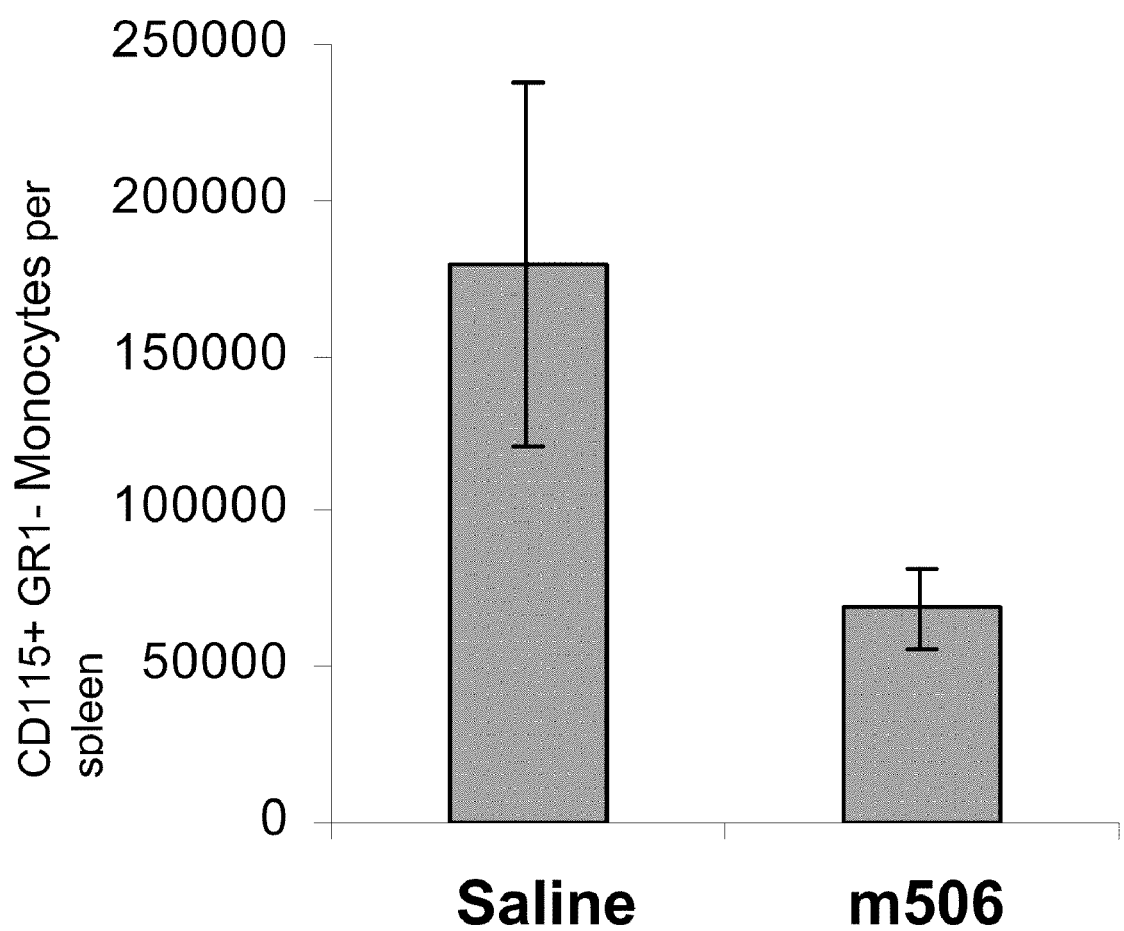
FIG. 14 shows that mCSF1R.506-Fc fusion protein (shown as m506) depletes CD115+ GR1− monocytes from spleen by more than 50%.

As shown in FIG. 13, treatment of DBA1 mice with mCSF1R.506-Fc resulted in a significant reduction of CD115$^+$GR1$^-$ monocytes in the spleen. The number of CD115$^+$GR1$^-$ cells per spleen decreased by more than 50% (FIG. 14). These data suggest that mCSF1R.506-Fc is effective in reducing the cell numbers of CD115$^+$GR1$^-$ monocytes.

TABLE OF SEQUENCES

Table 5 provides certain sequences discussed herein. All CSF1R sequences are shown without the signal peptide, unless otherwise indicated.

TABLE 5

Sequences and Descriptions

| SEQ. ID. NO. | Description | Sequence |
|---|---|---|
| 1 | hCSF1R-ECD.512 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD PQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDE |
| 2 | hCSF1R-ECD.506 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD PQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY |

TABLE 5-continued

Sequences and Descriptions

| SEQ. ID. NO. | Description | Sequence |
|---|---|---|
| | | SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAH |
| 3 | mCSF1R-ECD.511 | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQLPD ES |
| 4 | mCSF1R-ECD.506 | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWNPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQ |
| 5 | hCSF1R-ECD.512-Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LD4GGRKVMM SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 6 | hCSF1R-ECD.506.Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK |

TABLE 5-continued

Sequences and Descriptions

| SEQ. ID. NO. | Description | Sequence |
|---|---|---|
| | | VLTLNLDQVD FQHAGNYSCV ASNVQGKHST<br>SMFFRVVESA YLNLSSEQNL IQEVTVGEGL<br>NLKVMVEAYP GLQGFNWTYL GPFSDHQPEP<br>KLANATTKDT YRHTFTLSLP RLKPSEAGRY<br>SFLARNPGGW RALTFELTLR YPPEVSVIWT<br>FINGSGTLLC AASGYPGPNV TWLGCSGHTD<br>RCDEAQVLQV WDDPYPEVLS QEPFHKVTVQ<br>SLLTVETLEH NQTYECRAHN SVGSGSWAFI<br>PISAGAHEPK SSDKTHTCPP CPAPELLGGP<br>SVFLFPPKPK DTLMISRTPE VTCVVVDVSH<br>EDPEVKFNWY VDGVEVHNAK TKPREEQYNS<br>TYRVVSVLTV LHQDWLNGKE YKCKVSNKAL<br>PAPIEKTISK AKGQPREPQV YTLPPSRDEL<br>TKNQVSLTCL VKGFYPSDIA VEWESNGQPE<br>NNYKTTPPVL DSDGSFFLYS KLTVDKSRWQ<br>QGNVFSCSVM HEALHNHYTQ KSLSLSPGK |
| 7 | mCSF1R-ECD.511-Fc | APVIEPSGPE LVVEPGETVT LRCVSNGSVE<br>WDGPISPYWT LDPESPGSTL TTRNATFKNT<br>GTYRCTELED PMAGSTTTHL YVKDPAHSWN<br>LLAQEVTVVE GQEAVLPCLI TDPALKDSVS<br>LMREGGRQVL RKTVYFFSPW RGFIIRKAKV<br>LDSNTYVCKT MVNGRESTST GIWLKVNRVH<br>PEPPQIKLEP SKLVRIRGEA AQIVCSATNA<br>EVGFNVILKR GDTKLEIPLN SDFQDNYYKK<br>VRALSLNAVD FQDAGIYSCV ASNDVGTRTA<br>TMNFQVVESA YLNLTSEQSL LQEVSVGDSL<br>ILTVHADAYP SIQHYNWTYL GPFFEDQRKL<br>EFITQRAIYR YTFKLFLNRV KASEAGQYFL<br>MAQNKAGWNN LTFELTLRYP PEVSVTWMPV<br>NGSDVLFCDV SGYPQPSVTW MECRGHTDRC<br>DEAQALQVWN DTHPEVLSQK PFDKVIIQSQ<br>LPIGTLKHNM TYFCKTHNSV GNSSQYFRAV<br>SLGQSKQLPD ESEPKSSDKT HTCPPCPAPE<br>LLGGPSVFLF PPKPKDTLMI SRTPEVTCVV<br>VDVSHEDPEV KFNWYVDGVE VHNAKTKPRE<br>EQYNSTYRVV SVLTVLHQDW LNGKEYKCKV<br>SNKALPAPIE KTISKAKGQP REPQVYTLPP<br>SRDELTKNQV SLTCLVKGFY PSDIAVEWES<br>NGQPENNYKT TPPVLDSDGS FFLYSKLTVD<br>KSRWQQGNVF SCSVMHEALH NHYTQKSLSL<br>SPGK |
| 8 | mCSF1R-ECD.506-Fc | APVIEPSGPE LVVEPGETVT LRCVSNGSVE<br>WDGPISPYWT LDPESPGSTL TTRNATFKNT<br>GTYRCTELED PMAGSTTIHL YVKDPAHSWN<br>LLAQEVTVVE GQEAVLPCLI TDPALKDSVS<br>LMREGGRQVL RKTVYFFSPW RGFIIRKAKV<br>LDSNTYVCKT MVNGRESTST GIWLKVNRVH<br>PEPPQIKLEP SKLVRIRGEA AQIVCSATNA<br>EVGFNVILKR GDTKLEIPLN SDFQDNYYKK<br>VRALSLNAVD FQDAGTYSCV ASNDVGTRTA<br>TMNFQVVESA YLNLTSEQSL LQEVSVGDSL<br>ILTVHADAYP SIQHYNWTYL GPFFEDQRKL<br>EFITQRAIYR YTFKLFLNRV KASEAGQYFL<br>MAQNKAGWNN LTFELTLRYP PEVSVTWMPV<br>NGSDVLFCDV SGYPQPSVTW MECRGHTDRC<br>DEAQALQVWN DTHPEVLSQK PFDKVIIQSQ<br>LPIGTLKHNM TYFCKTHNSV GNSSQYFRAV<br>SLGQSKQEPK SSDKTHTCPP CPAPELLGGP<br>SVFLFPPKPK DTLMISRTPE VTCVVVDVSH<br>EDPEVKFNWY VDGVEVHNAK TKPREEQYNS<br>TYRVVSVLTV LHQDWLNGKE YKCKVSNKAL<br>PAPIEKTISK AKGQPREPQV YTLPPSRDEL<br>TKNQVSLTCL VKGFYPSDIA VEWESNGQPE<br>NNYKTTPPVL DSDGSFFLYS KLTVDKSRWQ<br>QGNVFSCSVD4 HEALHNHYTQ KSLSLSPGK |
| 9 | hCSF1R signal peptide | MGPGVLLLLL VATAWHGQG |
| 10 | mCSF1R signal peptide | MELGPPLVLL LATVWHGQG |
| 11 | hCSF1R-ECD.512 with signal peptide | MGPGVLLLLL VATAWHGQGI PVIEPSVPEL<br>VVKPGATVTL RCVGNGSVEW DGPPSPHWTL<br>YSDGSSSILS TNNATFQNTG TYRCTEPGDP<br>LGGSAAIHLY VKDPARPWNV LAQEVVVFED |

TABLE 5-continued

Sequences and Descriptions

| SEQ. ID. NO. | Description | Sequence |
|---|---|---|
| | | QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS NFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DE |
| 12 | hCSF1R-ECD.506 with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS NFFRVVESAY LNLSSEQNLI QEVTVGEGLN LKVMVEAYPG LQGFNWTYLG PFSDHQPEPK LAMATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAH |
| 13 | mCSF1R-ECD.511 with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL NREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTLKHNMT YFCKTHNSVG NSSQYFRAVS LGQSKQLPDE S |
| 14 | mCSF1R-ECD.506 with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWNPVN GSDVLFCDVS GYPQPSVTWM ECRGHTDRCD EAQALQVWND THPEVLSQKP FDKVIIQSQL PTGTLKHNMT YFCKTHNSVG NSSQYFRAVS LGQSKQ |
| 15 | hCSF1R-ECD.512-Fc with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWIM LAQEVVVFED QDALLPCLLT DPVLEAGVSL VRVRGRPLMR HTNYSFSPWH GFTIHRAKFI QSQDYQCSAL |

TABLE 5-continued

Sequences and Descriptions

| SEQ. ID. NO. | Description | Sequence |
|---|---|---|
| | | MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 16 | hCSF1R-ECD.506-Fc with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGGN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHEPKS SDKTHTCPPC PAPELLGGPS VFLFPPKPKD TLMTSRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 17 | mCSF1R-ECD.511-Fc with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQTKLEPS KLVRIRGEAA QIVCSATNAE VGFNVILKRG DTKLEIPLNS DFQDNYYKKV RALSLNAVDF QDAGIYSCVA SNDVGTRTAT MNFQVVESAY LNLTSEQSLL QEVSVGDSLT LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTLKHNNT YFCKTHNSVG NSSQYFRAVS LGQSKQLPDE SEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPTEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 18 | mCSF1R-ECD.506-Fc with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTTHLY VKDPAHSWNL LAQEVTVVEG |

TABLE 5-continued

Sequences and Descriptions

| SEQ. ID. NO. | Description | Sequence |
|---|---|---|
|  |  | QEAVLPCLIT DPALKDSVSL MREGGRQVLR<br>KTVYFFSPWR GFIIRKAKVL DSNTYVCKTM<br>VNGRESTSTG IWLKVNRVHP EPPQTKLEPS<br>KLVRIRGEAA QIVCSATNAE VGFNVILKRG<br>DTKLEIPLNS DFQDNYYKKV RALSLNAVDF<br>QDAGIYSCVA SNDVGTRTAT MNFQVVESAY<br>LNLTSEQSLL QEVSVGDSLI LTVHADAYPS<br>IQHYNWTYLG PFFEDQRKLE FITQRAIYRY<br>TFKLFLNRVK ASEAGQYFLM AQNKAGWNNL<br>TFELTLRYPP EVSVTWNPVT GSDVLFCDVS<br>GYPQPSVTWM ECRGHTDRCD EAQALQVWND<br>THPEVLSQKP FDKVIIQSQL PIGTLKHNMT<br>YFCKTHNSVG NSSQYFRAVS LGQSKQEPKS<br>SDKTHTCPPC PAPELLGGPS VFLFPPKPKD<br>TLMISRTPEV TCVVVDVSHE DPEVKFNWYV<br>DGVEVHNAKT KPREEQYNST YRVVSVLTVL<br>HQDWLNGKEY KCKVSNKALP APIEKTISKA<br>KGQPREPQVY TLPPSRDELT KNQVSLTCLV<br>KGFYPSDIAV EWESNGQPEN NYKTTPPVLD<br>SDGSFFLYSK LTVDKSRWQQ GNVFSCSVMH<br>EALHNHYTQK SLSLSPGK |
| 19 | Fc C237S | EPKSSDKTHT CPPCPAPELL GGPSVFLFPP<br>KPKDTLMISR TPEVTCVVVD VSHEDPEVKF<br>NWYVDGVEVH NAKTKPREEQ YNSTYRVVSV<br>LTVLHQDWLN GKEYKCKVSN KALPAPIEKT<br>ISKAKGQPRE PQVYTLPPSR DELTKNQVSL<br>TCLVKGFYPS DIAVEWESNG QPENNYKTTP<br>PVLDSDGSFF LYSKLTVDKS RWQQGNVFSC<br>SVMHEALHNH YTQKSLSLSP GK |
| 20 | Exemplary Fc #1 | ERKCCVECPP CPAPPVAGPS VFLFPPKPKD<br>TLMISRTPEV TCVVVDVSHE DPEVQFNWYV<br>DGVEVHNAKT KPREEQFNST FRVVSVLTVV<br>HQDWLNGKEY KCKVSNKGLP APIEKTISKT<br>KGQPREPQVY TLPPSREEMT KNQVSLTCLV<br>KGFYPSDIAV EWESNGQPEN NYKTTPPMLD<br>SDGSFFLYSK LTVDKSRWQQ GNVFSCSVMH<br>EALHNHYTQK SLSLSPGK |
| 21 | Exemplary Fc #2 | ESKYGPPCPS CPAPEFLGGP SVFLFPPKPK<br>DTLMISRTPE VTCVVVDVSQ EDPEVQFNWY<br>VDGVEVHNAK TKPREEQFNS TYRVVSVLTV<br>LHQDWLNGKE YKCKVSNKGL PSSIEKTISK<br>AKGQPREPQV YTLPPSQEEM TKNQVSLTCL<br>VKGFYPSDIA VEWESNGQPE NNYKTTPPVL<br>DSDGSFFLYS RLTVDKSRWQ EGNVFSCSVN<br>HEALHNHYTQ KSLSLSLGK |
| 22 | hCSF1R (full-length, no signal peptide) | IPVIEPSVPE LVVKPGATVT LRCVGNGSVE<br>WDGPPSPHWT LYSDGSSIL STNNATFQNT<br>GTYRCTEPGD PLGGSAAIHL YVKDPARPWN<br>VLAQEVVVFE DQDALLPCLL TDPVLEAGVS<br>LVRVRGRPLM RHTNYSFSPW HGFTIHRAKF<br>IQSQDYQCSA LMGGRKVMSI SIRLKVQKVI<br>PGPPALTLVP AELVRIRGEA AQIVCSASSV<br>DVNFDVFLQH NNTKLAIPQQ SDFHNNRYQK<br>VLTLNLDQVD FQHAGNYSCV ASNVQGKHST<br>SMFFRVVESA YLNLSSEQNL IQEVTVGEGL<br>NLKVMVEAYP GLQGFNWTYL GPFSDHQPEP<br>KLANATTKDT YRHTFTLSLP RLKPSEAGRY<br>SFLARNPGGW RALTFELTLR YPPEVSVIWT<br>FINGSGTLLC AASGYPQPNV TWLQCSGHTD<br>RCDEAQVLQV WDDPYPEVLS QEPFHKVTVQ<br>SLLTVETLEH NQTYECRAHN SVGSGSWAFI<br>PISAGAHTHP PDEFLFTPVV VACMSIMALL<br>LLLLLLLLYK YKQKPKYQVR WKIIESYEGN<br>SYTFIDPTQL PYNEKWEFPR NNLQFGKTLG<br>AGAFGKVVEA TAFGLGKEDA VLKVAVKMLK<br>STAHADEKEA LMSELKIMSH LGQHENIVNL<br>LGACTHGGPV LVITEYCCYG DLLNFLRRKA<br>EANLGPSLSP GQDPEGGVDY KNIHLEKKYV<br>RRDSGFSSQG VDTYVEMRPV STSSNDSFSE<br>QDLDKEDGRP LELRDLLHFS SQVAQGMAFL<br>ASKNCIHRDV AARNVLLTNG HVAKIGDFGL<br>ARDIMNDSNY IVKGNARLPV KWMAPESIFD |

| SEQ. ID. NO. | Description | Sequence |
|---|---|---|
| | | CVYTVQSDVW SYGILLWEIF SLGLNPYPGI LVNSKFYKLV KDGYQMAQPA FAPKNIYSIM QACWALEPTH RPTFQQICSF LQEQAQEDRR ERDYTNLPSS SRSGGSGSSS SELEEESSSE HLTCCEQGDI AQPLLQPNNY QEC |
| 23 | hCSF1F (full-length, + signal peptide) | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMP HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEFLFTPVVV ACMSIMALLL LLLLLLLYKY KQKPKYQVRW KIIESYEGNS YTFIDPTQLP YNEKWEFPRN NLQFGKTLGA GAFGKVVEAT AFGLGKEDAV LKVAVKMLKS TAHADEKEAL MSELKIMSHL GQHENIVNLL GACTHGGPVL VITEYCCYGD LLNFLRRKAE AMLGPSLSPG QDPEGGVDYK NIHLEKKYVR RDSGFSSQGV DTYVEMRPVS TSSNDSFSEQ DLDKEDGRPL ELRDLLHFSS QVAQGMAFLA SKNCIHRDVA ARNVLLTNGH VAKIGDFGLA RDIMNDSNYI VKGNARLPVK WNAPESIFDC VYTVQSDVWS YGILLWEIFS LGLNPYPGIL VNSKFYKLVK DGYQMAQPAF APKNIYSIMQ ACWALEPTHR PTFQQICSFL QEQAQEDRRE RDYTNLPSSS RSGGSGSSSS ELEEESSSEH LTCCEQGDIA QPLLQPNNYQ FC |
| 24 | mCSF1R (full-length, no signal peptide) | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWMM LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQLPD ESLFTPVVVA CMSVMSLLVL LLLLLLYKYK QKPKYQVRWK IIERYEGNSY TFIDPTQLPY NEKWEFPRNN LQFGKTLGAG AFGKVVEATA FGLGKEDAVL KVAVKMLKST AHADEKEALM SELKIMSHLG QHENIVNLLG ACTHGGPVLV ITEYCCYGDL LNFLRRKAEA MLGPSLSPGQ DSEGDSSYKN IHLEKKYVRR DSGFSSQGVD TYVEMRPVST SSSDSFFKQD LDKEASRPLE LWDLLHFSSQ VAQGMAFLAS KNCIHRDVAA RNVLLTSGHV AKIGDFGLAR DIMNDSNYVV KGNARLPVKW MAPESIFDCV YTVQSDVWSY GILLWEIFSL GLNPYPGILV NNKFYKLVKD GYQMAQPVFA PKNIYSIMQS CWDLEPTRRP TFQQICFLLQ EQARLERRDQ DYANLPSSGG SSGSDSGGGS SGGSSSEPEE ESSSEHLACC EPGDIAQPLL QPNNYQFC |

TABLE 5-continued

Sequences and Descriptions

| SEQ. ID. NO. | Description | Sequence |
|---|---|---|
| 25 | mSCF1R (full-length + signal peptide) | MELGPPLVLL LATVWHGQGA PVIEPSGPEL VVEPGETVTL RCVSNGSVEW DGPISPYWTL DPESPGSTLT TRNATFKNTG TYRCTELEDP MAGSTTIHLY VKDPAHSWNL LAQEVTVVEG QEAVLPCLIT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVILKRG DTKLEIPLNS DFQDNYYKKV RALSLNAVDF QDAGIYSCVA SNDVGTRTAT NNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWM ECRGHTDRCD EAQALQVWND THPEVLSQKP FDKVIIQSQL PIGTLKHNMT YFCKTHNSVG NSSQYFRAVS LGQSKQLPDE SLFTPVVVAC MSVMSLLVLL LLLLLYKYKQ KPKYQVRWKI IERYEGNSYT FIDPTQLPYN EKWEFPRNNL QFGKTLGAGA FGKVVEATAF GLGKEDAVLK VAVKMLKSTA HADEKEALMS ELKIMSHLGQ HENIVNLLGA CTHGGPVLVI TEYCCYGDLL NFLRRKAEAM LGPSLSPGQD SEGDSSYKNI HLEKKYVRRD SGFSSQGVDT YVEMRPVSTS SSDSFFKQDL DKEASRPLEL WDLLHFSSQV AQGMAFLASK NCIHRDVAAR NVLLTSGHVA KIGDFGLARD IMNDSNYVVK GNARLPVKWM APESIFDCVY TVQSDVWSYG ILLWEIFSLG LNPYPGILVN NKFYKLVKDG YQMAQPVFAP KNIYSIMQSC WDLEPTRRPT FQQICFLLQE QARLERRDQD YANLPSSGGS SGSDSGGGSS GGSSSEPEEE SSSEHLACCE PGDIAQPLLQ PNNYQFC |
| 26 | hCSF1R-ECD.511 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PD |
| 27 | hCSF1R-ECD.511 with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP D |
| 28 | hCSF1R-ECD.511.Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF |

TABLE 5-continued

Sequences and Descriptions

| SEQ. ID. NO. | Description | Sequence |
|---|---|---|
| | | IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 29 | hCSF1R-ECD.511-Fc with signal peptide | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVNSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVDVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTPPP DEPKSSDKTH TCPPCPAPEL LGGPSVFLFP PKPKDTLDMS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 30 | Fc C237S with N-terminal GS linker | GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV LTCLVKGFYP SDIAVEWESN GQPENNYKTT PPVLDSDGSF FLYSKLTVDK SRWQQGNVFS CSVMHEALHN HYTQKSLSLS PGK |
| 31 | hCSF1R-ECD.512-Fc with GS linker | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLD RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEGFEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK |

TABLE 5-continued

Sequences and Descriptions

| SEQ. ID. NO. | Description | Sequence |
|---|---|---|
| | | CKVSNKALPA PIEKTISKAK GQPREPQVYT LPPSRDELTK NQVSLTCLVK GFYPSDTAVE WESNGQPENN YKTTPPVLDS DGSFFLYSKL TVDKSRWQQG NVFSCSVMHE ALHNHYTQKS LSLSPGK |
| 32 | hCSF1R-ECD.506-Fc with GS linker | TPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLN RHTNYSFSPW HGFTIHRAKF IQSQDYQCSA LMGGRKVMSI SIRLKVQKVT PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVTWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHGFE PKSSDKTHTC PPCPAPELLG GPSVFLFPPK PKDTLNISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 33 | mCSF1R-ECD.511-Fc with GS linker | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQTKLEP SKLVRIRGEA AQIVCSATNA EVGFNVTLKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW NECRGHTDRC DEAQALQVWN DTHPEVLSQK PFDKVIIQSQ LPIGTLKHNM TYFCKTHNSV GNSSQYFRAV SLGQSKQLPD ESGFEPKSSD KTHTCPPCPA PELLGGPSVF LFPPKPKDTL NISRTPEVTC VVVDVSHEDP EVKFNWYVDG VEVHNAKTKP REEQYNSTYR VVSVLTVLHQ DWLNGKEYKC KVSNKALPAP IEKTTSKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 34 | mCSF1R-ECD.506-Fc with GS linker | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LNREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYMATYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQGFE PKSSDKTHTC PPCPAPELLG GPSVFLFPPK PKDTLMISRT PEVTCVVVDV |

TABLE 5-continued

Sequences and Descriptions

| SEQ. ID. NO. | Description | Sequence |
|---|---|---|
| | | SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 35 | hCSF1R-ECD.512-Fc with signal peptide and GS linker | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLNR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEGFEPKSSD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 36 | hCSF1R-ECD.506-Fc with signal peptide and GS linker | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVTP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVTWTF INGSGTLLCA ASGYPQPNVT WLQCSGHTDR CDEAQVLQVW DDPYPEVLSQ EPFHKVTVQS LLTVETLEHN QTYECRAHNS VGSGSWAFTP ISAGAHGFEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV NHEALHNHYT QKSLSLSPGK |
| 37 | mCSF1R-ECD.511-Fc with signal peptide | MELGPPLVLL LATVWHGQGA PVIEPSGPEL VVEPGETVTL RCVSNGSVEW DGPISPYWTL DPESPGSTLT TRNATFKNTG TYRCTELEDP NAGSTTIHLY VKDPAHSWNL LAQEVTVVEG QEAVLPCLTT DPALKDSVSL MREGGRQVLR KTVYFFSPWR GFIIRKAKVL DSNTYVCKTM VNGRESTSTG IWLKVNRVHP EPPQIKLEPS KLVRIRGEAA QIVCSATNAE VGFNVTLKRG DTKLEIPLNS DFQDNYYKKV RALSLNAVDF QDAGIYSCVA SNDVGTRTAT MNFQVVESAY LNLTSEQSLL QEVSVGDSLI LTVHADAYPS IQHYNWTYLG PFFEDQRKLE FITQRAIYRY TFKLFLNRVK ASEAGQYFLM AQNKAGWNNL TFELTLRYPP EVSVTWMPVN GSDVLFCDVS GYPQPSVTWN ECRGHTDRCD EAQALQVWND THPEVLSQKP FDKVIIQSQL PTGTLKHNNT |

TABLE 5-continued

Sequences and Descriptions

| SEQ. ID. NO. | Description | Sequence |
|---|---|---|
| | | YFCKTHNSVG NSSQYFRAVS LGQSKQLPDE<br>SGFEPKSSDK THTCPPCPAP ELLGGPSVFL<br>FPPKPKDTLM ISRTPEVTCV VVDVSHEDPE<br>VKFNWYVDGV EVHNAKTKPR EEQYNSTYRV<br>VSVLTVLHQD WLNGKEYKCK VSNKALPAPI<br>EKTISKAKGQ PREPQVYTLP PSRDELTKNQ<br>VSLTCLVKGF YPSDIAVEWE SNGQPENNYK<br>TTPPVLDSDG SFFLYSKLTV DKSRWQQGNV<br>FSCSVMHEAL HNHYTQKSLS LSPGK |
| 38 | mCSF1R-ECD.506-Fc with signal peptide and GS linker | MELGPPLVLL LATVWHGQGA PVIEPSGPEL<br>VVEPGETVTL RCVSNGSVEW DGPISPYWTL<br>DPESPGSTLT TRNATFKNTG TYRCTELEDP<br>MAGSTTIHLY VKDPAHSWNL LAQEVTVVEG<br>QEAVLPCLIT DPALKDSVSL MREGGRQVLR<br>KTVYFFSPWR GFIIRKAKVL DSNTYVCKTM<br>VNGRESTSTG IWLKVNRVHP EPPQIKLEPS<br>KLVRIRGEAA QIVCSATNAE VGFNVILKRG<br>DTKLEIPLNS DFQDNYYKKV RALSLNAVDF<br>QDAGIYSCVA SNDVGTRTAT MNFQVVESAY<br>LNLTSEQSLL QEVSVGDSLI LTVHADAYPS<br>IQHYNWTYLG PFFEDQRKLE FITQRAIYRY<br>TFKLFLNRVK ASEAGQYFLM AQNKAGWNNL<br>TFELTLRYPP EVSVTWMPVN GSDVLFCDVS<br>GYPQPSVTWM ECRGHTDRCD EAQALQVWND<br>THPEVLSQKP FDKVIIQSQL PIGTLKHNNT<br>YFCKTHNSVG NSSQYFPAVS LGQSKQGFEP<br>KSSDKTHTCP PCPAPELLGG PSVFLFPPKP<br>KDTLMISRTP EVTCVVVDVS HEDPEVKFNW<br>YVDGVEVHNA KTKPREEQYN STYRVVSVLT<br>VLHQDWLNGK EYKCKVSNKA LPAPIEKTIS<br>KAKGQPREPQ VYTLPPSRDE LTKNQVSLTC<br>LVKGFYPSDI AVEWESNGQP ENNYKTTPPV<br>LDSDGSFFLY SKLTVDKSRW QQGNVFSCSV<br>MHEALHNHYT QKSLSLSPGK |
| 39 | mCSF1R-ECD.506-Fc with signal sequence | ATGGGCCCAG GAGTTCTGCT GCTCCTGCTG<br>GTGGCCACAG CTTGGCATGG TCAGGGAATC<br>CCAGTGATAG AGCCCAGTGT CCCTGAGCTG<br>GTCGTGAAGC CAGGAGCAAC GGTGACCTTG<br>CGATGTGTGG GCAATGGCAG CGTGGAATGG<br>GATGGCCCCC CATCACCTCA CTGGACCCTG<br>TACTCTGATG GCTCCAGCAG CATCCTCAGC<br>ACCAACAACG CTACCTTCCA AAACACGGGG<br>ACCTATCGCT GCACTGAGCC TGGAGACCCC<br>CTGGGAGGCA GCGCCGCCAT CCACCTCTAT<br>GTCAAAGACC CTGCCCGGCC CTGGAACGTG<br>CTAGCACAGG AGGTGGTCGT GTTCGAGGAC<br>CAGGACGCAC TACTGCCCTG TCTGCTCACA<br>GACCCGGTGC TGGAAGCAGG CGTCTCGCTG<br>GTGCGTGTGC GTGGCCGGCC CCTCATGCGC<br>CACACCAACT ACTCCTTCTC GCCCTGGCAT<br>GGCTTCACCA TCCACAGGGC CAAGTTCATT<br>CAGAGCCAGG ACTATCAATG CAGTGCCCTG<br>ATGGGTGGCA GGAAGGTGAT GTCCATCAGC<br>ATCCGGCTGA AAGTGCAGAA AGTCATCCCA<br>GGGCCCCCAG CCTTGACACT GGTGCCTGCA<br>GAGCTGGTGC GGATTCGAGG GGAGGCTGCC<br>CAGATCGTGT GCTCAGCCAG CAGCGTTGAT<br>GTTAACTTTG ATGTCTTCCT CCAACACAAC<br>AACACCAAGC TCGCAATCCC TCAACAATCT<br>GACTTTCATA ATAACCGTTA CCAAAAAGTC<br>CTGACCCTCA ACCTCGATCA AGTAGATTTC<br>CAACATGCCG GCAACTACTC CTGCGTGGCC<br>AGCAACGTGC AGGGCAAGCA CTCCACCTCC<br>ATGTTCTTCC GGGTGGTAGA GAGTGCCTAC<br>TTGAACTTGA GCTCTGAGCA GAACCTCATC<br>CAGGAGGTGA CCGTGGGGGA GGGGCTCAAC<br>CTCAAAGTCA TGGTGGAGGC CTACCCAGGC<br>CTGCAAGGTT TTAACTGGAC CTACCTGGGA<br>CCCTTTTCTG ACCACCAGCC TGAGCCCAAG<br>CTTGCTAATG CTACCACCAA GGACACATAC<br>AGGCACACCT TCACCCTCTC TCTGCCCCGC<br>CTGAAGCCCT CTGAGGCTGG CCGCTACTCC<br>TTCCTGGCCA GAAACCCAGG AGGCTGGAGA<br>GCTCTGACGT TTGAGCTCAC CCTTCGATAC |

TABLE 5-continued

Sequences and Descriptions

| SEQ. ID. NO. | Description | Sequence |
|---|---|---|
| | | CCCCCAGAGG TAAGCGTCAT ATGGACATTC |
| | | ATCAACGGCT CTGGCACCCT TTTGTGTGCT |
| | | GCCTCTGGGT ACCCCCAGCC AACGTGACA |
| | | TGGCTGCAGT GCAGTGGCCA CACTGATAGG |
| | | TGTGATGAGG CCCAAGTGCT GCAGGTCTGG |
| | | GATGACCCAT ACCCTGAGGT CCTGAGCCAG |
| | | GAGCCCTTCC ACAAGGTGAC GGTGCAGAGC |
| | | CTGCTGACTG TTGAGACCTT AGAGCACAAC |
| | | CAAACCTACG AGTGCAGGGC CCACAACAGC |
| | | GTGGGGAGTG GCTCCTGGGC CTTCATACCC |
| | | ATCTCTGCAG GAGCCCACGA GCCCAAATCT |
| | | TCTGACAAAA CTCACACATG CCCACCGTGC |
| | | CCAGCACCTG AACTCCTGGG GGGACCGTCA |
| | | GTCTTCCTCT TCCCCCCAAA ACCCAAGGAC |
| | | ACCCTCATGA TCTCCCGGAC CCCTGAGGTC |
| | | ACATGCGTGG TGGTGGACGT GAGCCACGAA |
| | | GACCCTGAGG TCAAGTTCAA CTGGTACGTG |
| | | GACGGCGTGG AGGTGCATAA TGCCAAGACA |
| | | AAGCCGCGGG AGGAGCAGTA CAACAGCACG |
| | | TACCGTGTGG TCAGCGTCCT CACCGTCCTG |
| | | CACCAGGACT GGCTGAATGG CAAGGAGTAC |
| | | AAGTGCAAGG TCTCCAACAA AGCCCTCCCA |
| | | GCCCCCATCG AGAAAACCAT CTCCAAAGCC |
| | | AAAGGGCAGC CCCGAGAACC ACAGGTGTAC |
| | | ACCCTGCCCC CATCCCGGGA TGAGCTGACC |
| | | AAGAACCAGG TCAGCCTGAC CTGCCTGGTC |
| | | AAAGGCTTCT ATCCCAGCGA CATCGCCGTG |
| | | GAGTGGGAGA GCAATGGGCA GCCGGAGAAC |
| | | AACTACAAGA CCACGCCTCC CGTGCTGGAC |
| | | TCCGACGGCT CCTTCTTCCT CTACAGCAAG |
| | | CTCACCGTGG ACAAGAGCAG GTGGCAGCAG |
| | | GGGAACGTCT TCTCATGCTC CGTGATGCAT |
| | | GAGGCTCTGC ACAACCACTA CACGCAGAAG |
| | | AGCCTCTCCC TGTCTCCGGG TAAA |
| 40 | hCSF1R-ECD.506-Fc | ATCCCAGTGA TAGAGCCCAG TGTCCCTGAG |
| | | CTGGTCGTGA AGCCAGGAGC AACGGTGACC |
| | | TTGCGATGTG TGGGCAATGG CAGCGTGGAA |
| | | TGGGATGGCC CCCCATCACC TCACTGGACC |
| | | CTGTACTCTG ATGGCTCCAG CAGCATCCTC |
| | | AGCACCAACA ACGCTACCTT CCAAAACACG |
| | | GGGACCTATC GCTGCACTGA GCCTGGAGAC |
| | | CCCCTGGGAG GCAGCGCCGC CATCCACCTC |
| | | TATGTCAAAG ACCCTGCCCG GCCCTGGAAC |
| | | GTGCTAGCAC AGGAGGTGGT CGTGTTCGAG |
| | | GACCAGGACG CACTACTGCC CTGTCTGCTC |
| | | ACAGACCCGG TGCTGGAAGC AGGCGTCTCG |
| | | CTGGTGCGTG TGCGTGGCCG GCCCCTCATG |
| | | CGCCACACCA ACTACTCCTT CTCGCCCTGG |
| | | CATGGCTTCA CCATCCACAG GGCCAAGTTC |
| | | ATTCAGAGCC AGGACTATCA ATGCAGTGCC |
| | | CTGATGGGTG GCAGGAAGGT GATGTCCATC |
| | | AGCATCCGGC TGAAAGTGCA GAAAGTCATC |
| | | CCAGGGCCCC CAGCCTTGAC ACTGGTGCCT |
| | | GCAGAGCTGG TGCGGATTCG AGGGGAGGCT |
| | | GCCCAGATCG TGTGCTCAGC CAGCAGCGTT |
| | | GATGTTAACT TTGATGTCTT CCTCCAACAC |
| | | AACAACACCA AGCTCGCAAT CCCTCAACAA |
| | | TCTGACTTTC ATAATAACCG TTACCAAAAA |
| | | GTCCTGACCC TCAACCTCGA TCAAGTAGAT |
| | | TTCCAACATG CCGGCAACTA CTCCTGCGTG |
| | | GCCAGCAACG TGCAGGGCAA GCACTCCACC |
| | | TCCATGTTCT TCCGGGTGGT AGAGAGTGCC |
| | | TACTTGAACT TGAGCTCTGA GCAGAACCTC |
| | | ATCCAGGAGG TGACCGTGGG GGAGGGGCTC |
| | | AACCTCAAAG TCATGGTGGA GGCCTACCCA |
| | | GGCCTGCAAG GTTTTAACTG GACCTACCTG |
| | | GGACCCTTTT CTGACCACCA GCCTGAGCCC |
| | | AAGCTTGCTA ATGCTACCAC CAAGGACACA |
| | | TACAGGCACA CCTTCACCCT CTCTCTGCCC |
| | | CGCCTGAAGC CCTCTGAGGC TGGCCGCTAC |
| | | TCCTTCCTGG CCAGAAACCC AGGAGGCTGG |
| | | AGAGCTCTGA CGTTTGAGCT CACCCTTCGA |
| | | TACCCCCCAG AGGTAAGCGT CATATGGACA |
| | | TTCATCAACG GCTCTGGCAC CCTTTTGTGT |
| | | GCTGCCTCTG GGTACCCCCA GCCCAACGTG |

TABLE 5-continued

Sequences and Descriptions

| SEQ. ID. NO. | Description | Sequence |
|---|---|---|
| | | ACATGGCTGC AGTGCAGTGG CCACACTGAT |
| | | AGGTGTGATG AGGCCCAAGT GCTGCAGGTC |
| | | TGGGATGACC CATACCCTGA GGTCCTGAGC |
| | | CAGGAGCCCT TCCACAAGGT GACGGTGCAG |
| | | AGCCTGCTGA CTGTTGAGAC CTTAGAGCAC |
| | | AACCAAACCT ACGAGTGCAG GGCCCACAAC |
| | | AGCGTGGGGA GTGGCTCCTG GGCCTTCATA |
| | | CCCATCTCTG CAGGAGCCCA CGAGCCCAAA |
| | | TCTTCTGACA AAACTCACAC ATGCCCACCG |
| | | TGCCCAGCAC CTGAACTCCT GGGGGGACCG |
| | | TCAGTCTTCC TCTTCCCCCC GGGGGGACCG |
| | | GACACCCTCA TGATCTCCCG GACCCCTGAG |
| | | GTCACATGCG TGGTGGTGGA CGTGAGCCAC |
| | | GAAGACCCTG AGGTCAAGTT CAACTGGTAC |
| | | GTGGACGGCG TGGAGGTGCA TAATGCCAAG |
| | | ACAAAGCCGC GGGAGGAGCA GTACAACAGC |
| | | ACGTACCGTG TGGTCAGCGT CCTCACCGTC |
| | | CTGCACCAGG ACTGGCTGAA TGGCAAGGAG |
| | | TACAAGTGCA AGGTCTCCAA CAAAGCCCTC |
| | | CCAGCCCCCA TCGAGAAAAC CATCTCCAAA |
| | | GCCAAAGGGC AGCCCCGAGA ACCACAGGTG |
| | | TACACCCTGC CCCCATCCCG GGATGAGCTG |
| | | ACCAAGAACC AGGTCAGCCT GACCTGCCTG |
| | | GTCAAAGGCT TCTATCCCAG CGACATCGCC |
| | | GTGGAGTGGG AGAGCAATGG GCAGCCGGAG |
| | | AACAACTACA AGACCACGCC TCCCGTGCTG |
| | | GACTCCGACG GCTCCTTCTT CCTCTACAGC |
| | | AAGCTCACCG TGGACAAGAG CAGGTGGCAG |
| | | CAGGGGAACG TCTTCTCATG CTCCGTGATG |
| | | CATGAGGCTC TGCACAACCA CTACACGCAG |
| | | AAGAGCCTCT CCCTGTCTCC GGGTAAA |

We claim:

1. A colony stimulating factor 1 receptor (CSF1R) extracellular domain (ECD) fusion molecule comprising a CSF1R ECD and one or more fusion partners, wherein the amino acid sequence of the CSF1R ECD fusion molecule comprises SEQ ID NO.:2 and excludes the last six C-terminal amino acid residues of SEQ ID NO.:1.

2. The CSF1R ECD fusion molecule of claim 1, wherein the one or more fusion partners is selected from an Fc, albumin, and polyethylene glycol.

3. The CSF1R ECD fusion molecule of claim 2, wherein the one or more fusion partners is an Fc.

4. The CSF1R ECD fusion molecule of claim 2, wherein the one or more fusion partners is an Fc and polyethylene glycol.

5. The CSF1R ECD fusion molecule of claim 2, wherein the one or more fusion partners is polyethylene glycol.

6. The CSF1R ECD fusion molecule of claim 1, wherein the CSF1R ECD comprises a signal peptide.

7. The CSF1R ECD fusion molecule of claim 1, wherein the CSF1R ECD amino acid sequence consists of SEQ ID NO:2.

8. The CSF1R ECD fusion molecule of claim 1, wherein the fusion molecule comprises a linker between the CSF1R ECD and one or more fusion partners.

9. The CSF1R ECD fusion molecule of claim 1, wherein the amino acid sequence of the fusion molecule is expressed in Chinese hamster ovary (CHO) cells.

10. A CSF1R ECD fusion molecule comprising a CSF1R ECD and an Fc, wherein the amino acid sequence of the CSF1R ECD fusion molecule comprises SEQ ID NO.:6.

11. The CSF1R ECD fusion molecule of claim 10, wherein the fusion molecule is expressed in Chinese hamster ovary (CHO) cells.

12. The CSF1R ECD fusion molecule of claim 10, wherein the CSF1R ECD comprises a signal peptide.

13. The CSF1R ECD fusion molecule of claim 10, wherein the amino acid sequence of the CSF1R ECD fusion molecule consists of SEQ ID NO.:6.

14. The CSF1R ECD fusion molecule of claim 13, wherein the fusion molecule is expressed in CHO cells.

15. A CSF1R ECD fusion molecule comprising a CSF1R ECD, an Fc, and polyethylene glycol, wherein the amino acid sequence of the CSF1R ECD fusion molecule comprises SEQ ID NO.:6.

16. The CSF1R ECD fusion molecule of claim 15, wherein the CSF1R ECD comprises a signal peptide.

17. The CSF1R ECD fusion molecule of claim 15, wherein the amino acid sequence of the fusion molecule is expressed in Chinese hamster ovary (CHO) cells.

18. The CSF1R ECD fusion molecule of claim 15, wherein the amino acid sequence of the CSF1R ECD fusion molecule consists of SEQ ID NO.:6.

19. The CSF1R ECD fusion molecule of claim 18, wherein the amino acid sequence of the fusion molecule is expressed in CHO cells.

20. A polynucleotide comprising a nucleic acid sequence that encodes the CSF1R ECD fusion molecule of claim 1.

21. A polynucleotide comprising a nucleic acid sequence that encodes the CSF1R ECD fusion molecule of claim 13.

22. The polynucleotide of claim 21, wherein the nucleic acid sequence encodes the CSF1R ECD fusion molecule of SEQ ID NO:16.

23. The polynucleotide of claim 21, wherein the nucleic acid sequence comprises SEQ ID NO:39.

24. The polynucleotide of claim 21, wherein the nucleic acid sequence comprises SEQ ID NO:40.

* * * * *

UNITED STATES PATENT AND TRADEMARK OFFICE
CERTIFICATE OF CORRECTION

PATENT NO. : 8,080,246 B2
APPLICATION NO. : 12/626598
DATED : December 20, 2011
INVENTOR(S) : Haishan Lin and Li Long Page 1 of 1

It is certified that error appears in the above-identified patent and that said Letters Patent is hereby corrected as shown below:

On the cover page, "Other Publications" section, please add the following:
--SIGMA, Product Information for Macrophage Colony Stimulating Factor Receptor/Fc Chimera (M-CSF R, CD115) Human, Recombinant, Expressed in mouse NSO cells, Product Number M 7559, 2 pages. NO DATE AVAILABLE.--

In Claim 15, col. 188, line 10, "sequence of the CSF1 R ECD" should read --sequence of the CSF1R ECD--.

Signed and Sealed this
Sixth Day of March, 2012

David J. Kappos
*Director of the United States Patent and Trademark Office*